US008785365B2

(12) United States Patent
Bessler et al.

(10) Patent No.: US 8,785,365 B2
(45) Date of Patent: Jul. 22, 2014

(54) ALPHA-AMYLASE VARIANTS STABILIZED AGAINST DIMERIZATION AND/OR MULTIMERIZATION, METHOD FOR THE PRODUCTION THEREOF, AND DETERGENTS AND CLEANSERS CONTAINING THESE ALPHA-AMYLASE VARIANTS

(75) Inventors: Cornelius Bessler, Dusseldorf (DE); Susanne Wieland, Dormagen-Zons (DE); Karl-Heinz Maurer, Erkrath (DE)

(73) Assignee: BASF SE, Ludwigshafen (DE)

( * ) Notice: Subject to any disclaimer, the term of this patent is extended or adjusted under 35 U.S.C. 154(b) by 947 days.

(21) Appl. No.: 11/692,691

(22) Filed: Mar. 28, 2007

(65) Prior Publication Data

US 2007/0212768 A1 Sep. 13, 2007

Related U.S. Application Data

(63) Continuation of application No. PCT/EP2005/010259, filed on Sep. 22, 2005.

(30) Foreign Application Priority Data

Oct. 1, 2004 (DE) .................. 10 2004 047 776

(51) Int. Cl.
C12N 9/28 (2006.01)
C11D 3/386 (2006.01)
C12S 11/00 (2006.01)
C12S 9/00 (2006.01)

(52) U.S. Cl.
USPC ............ 510/392; 435/202; 435/263; 435/264

(58) Field of Classification Search
None
See application file for complete search history.

(56) References Cited

U.S. PATENT DOCUMENTS

| 5,382,377 | A | 1/1995 | Raehse et al. | |
|---|---|---|---|---|
| 5,616,550 | A | 4/1997 | Kruse et al. | |
| 6,075,001 | A | 6/2000 | Wilde | |
| 6,417,151 | B1 | 7/2002 | Grothus et al. | |
| 6,541,233 | B1 | 4/2003 | Hillen et al. | |
| 7,153,818 | B2 * | 12/2006 | Breves et al. ................. | 510/226 |
| 2004/0005695 | A1 | 1/2004 | Miksch et al. | |
| 2004/0102349 | A1 | 5/2004 | Breves et al. | |
| 2004/0235125 | A1 | 11/2004 | Kottwitz et al. | |
| 2004/0259222 | A1 | 12/2004 | Breves et al. | |
| 2005/0003419 | A1 | 1/2005 | Breves et al. | |
| 2005/0003504 | A1 | 1/2005 | Weber et al. | |
| 2005/0003985 | A1 | 1/2005 | Kottwitz et al. | |
| 2005/0009167 | A1 | 1/2005 | Weber et al. | |
| 2005/0026269 | A1 | 2/2005 | Kottwitz et al. | |
| 2005/0043198 | A1 | 2/2005 | Kottwitz et al. | |
| 2005/0049165 | A1 | 3/2005 | Kottwitz et al. | |
| 2005/0113273 | A1 | 5/2005 | Weber et al. | |
| 2005/0266542 | A1 | 12/2005 | Baur et al. | |
| 2005/0281773 | A1 | 12/2005 | Wieland et al. | |
| 2005/0282261 | A1 | 12/2005 | Sauter et al. | |
| 2007/0128129 | A1 | 6/2007 | Stehr et al. | |

FOREIGN PATENT DOCUMENTS

| DE | 19616693 | 11/1997 |
|---|---|---|
| DE | 19616767 | 11/1997 |
| DE | 10138753 | 3/2003 |
| DE | 102004021384 | 11/2004 |
| DE | 102004029475 | 1/2006 |
| DE | 102004020430 | 5/2009 |
| EP | 0486592 | 5/1992 |
| EP | 0525239 | 2/1993 |
| EP | 0642576 | 3/1995 |
| EP | 985731 | 3/2000 |
| EP | 1022334 | 7/2000 |
| EP | 1199356 | 4/2002 |
| WO | WO9102792 | 3/1991 |
| WO | WO9221760 | 12/1992 |
| WO | WO9418314 | 8/1994 |
| WO | WO9523221 | 8/1995 |
| WO | WO9623873 | 8/1996 |
| WO | WO9623874 | 8/1996 |
| WO | WO9629397 | 9/1996 |
| WO | WO9634092 | 10/1996 |
| WO | WO9718287 | 5/1997 |
| WO | WO9741213 | 11/1997 |
| WO | WO9812307 | 3/1998 |

(Continued)

OTHER PUBLICATIONS

Guex, von N. and Peitsch M.C. "An Environment for Comparative Protein Modeling" Electrophoresis, vol. 18, pp. 2714-2723, 1997.
Connolly, M.L., "Solvent-Acessible Surfaces of Proteins and Nucleic Acids", Science, 1983, vol. 221, No. 4612, pp. 709-713.
Mehler et al., Electrostatic Effects in Proteins: Comparison of Dielectric and Charges Models, Protein Engineering, vol. 4, No. 8, pp. 903-010, 1991.
Jakalian, et al. "Fast, Efficient Generation of High-Quality Atomic charges, AM1-BCC Model: II. Parameterization and Validation", Journal of Computational Chemistry, vol. 23, No. 16, pp. 1623-1641, 2002.

(Continued)

*Primary Examiner* — Rebecca Prouty
(74) *Attorney, Agent, or Firm* — Brinks, Gilson & Lione

(57) ABSTRACT

The present invention relates to α-amylase variants that are stabilized to dimerization and/or multimerization, in particular at elevated temperatures or high pH, by point mutagenesis of positively polarized or charged or neutral surface amino acids to give more negatively polarized or charged amino acids. The invention further relates to methods of increasing the stability of an α-amylase to dimerization and/or multimerization brought about by electrostatic interactions whereby at least one amino acid residue on the surface of the starting molecule, which makes a neutral or positively polar or charged contribution to the electrostatic potential of said molecule, is replaced with a more negatively polar or negatively charged amino acid residue. The α-amylase variants obtained thereby exhibit better stability to influences of the solvent, increased processivity, and are suited for numerous industrial areas of use, in particular as active ingredients in detergents and cleansers.

9 Claims, 4 Drawing Sheets

(56) References Cited

FOREIGN PATENT DOCUMENTS

| WO | WO9845398 | 10/1998 |
|---|---|---|
| WO | WO9906573 | 2/1999 |
| WO | WO9963035 | 12/1999 |
| WO | WO9963036 | 12/1999 |
| WO | WO9963037 | 12/1999 |
| WO | WO0060059 | 10/2000 |
| WO | WO0060060 | 10/2000 |
| WO | WO0166712 | 9/2001 |
| WO | WO0181597 | 11/2001 |
| WO | WO0206508 | 1/2002 |
| WO | WO0210356 | 2/2002 |
| WO | WO0022103 | 4/2002 |
| WO | WO0244350 | 6/2002 |
| WO | 02/092797 | * 11/2002 |
| WO | WO02088340 | 11/2002 |
| WO | WO03002711 | 1/2003 |
| WO | WO03014358 | 2/2003 |
| WO | WO03038082 | 5/2003 |
| WO | WO03054177 | 7/2003 |
| WO | WO03054184 | 7/2003 |
| WO | WO03054185 | 7/2003 |
| WO | WO03055974 | 7/2003 |
| WO | WO03056017 | 7/2003 |
| WO | WO2004058955 | 7/2004 |
| WO | WO2004058961 | 7/2004 |
| WO | WO2004067557 | 8/2004 |
| WO | WO2005056782 | 6/2005 |

OTHER PUBLICATIONS

Long-Lui et al., "Production and Property of a Raw-Starch-Degrading Amylase from the Thermophillic and Alakliphilic *Bacillus* sp. TS-23" 1998 Biotechnol. Appl., Biochem., vol. 28, pp. 61-68.

Gornall et al, Determination of Serum Proteins by Means of the Biuret Reaction, 1948, J. Biol. Hem., vol. 177, pp. 751-766.

Hassan et al., "A Critical Analysis of Continuum Electrostatics: The Screened Coulomb Potential-Implicit Solvent Model and the Study of the Alanine Dipeptide and Discrimination of Misfolded Structures of Proteins", in Proteins: Structure, Function and Genetics 47, 2002, Wiley-Liss, Inc., pp. 45-61.

Tsukamoto et al., "Nucleotide Sequence of the Maltohexaose-Producing Amylase Gene From an Alkalophilic *Bascillus* sp. 707 and Structural Similarity to Liquefying Type α-Amylases" Biochem. Biophys. Res., Comm., vol. 151, pp. 25-31, 1988.

* cited by examiner

FIG. 2A

```
                 1                                                  50
A 7-7    (1)   -HHNGTNGTMMQYFEWYLPNDGNHWNRLRSDASNLKDKGITAVWIPPAWK
S707     (1)   -HHNGTNGTMMQYFEWYLPNDGNHWNRLNSDASNLKSKGITAVWIPPAWK
LAMY     (1)   -HHNGTNGTMMQYFEWHLPNDGNHWNRLRDDAANLKSKGITAVWIPPAWK
BAA      (1)   -----VNGTLMQYFEWYTPNDGQHWKRLQNDAEHLSDIGITAVWIPPAYK
BLA      (1)   ---ANLNGTLMQYFEWYMPNDGQHWKRLQNDSAYLAEHGITAVWIPPAYK
BStA     (1)   --AAPFNGTMMQYFEWYLPDDGTLWTKVANEANNLSSLGITALWLPPAYK
MK716    (1)   --AAPFNGTMMQYFEWYLPDDGTLWTKVANEANNLSSLGITALWLPPAYK
TS-23    (1)   ANTAPINETMMQYFEWDLPNDGTLWTKVKNEAANLSSLGITALWLPPAYK
K38      (1)   --ADGLNGTMMQYYEWHLENDGQHWNRLHDDAAALSDAGITAIWIPPAYK 51                                                 100
A 7-7   (50)   GASQNDVGYGAYDLYDLGEFNQKGTVRTKYGTRNQLQAAVTALKSNGIQV
S707    (50)   GASQNDVGYGAYDLYDLGEFNQKGTVRTKYGTRSQLQAAVTSLKNNGIQV
LAMY    (50)   GTSQNDVGYGAYDLYDLGEFNQKGTVRTKYGTRSQLQGAVTSLKNNGIQV
BAA     (46)   GLSQSDNGYGPYDLYDLGEFQQKGTVRTKYGTKSELQDAIGSLHSRNVQV
BLA     (48)   GTSQADVGYGAYDLYDLGEFHQKGTVRTKYGTKGELQSAIKSLHSRDINV
BStA    (49)   GTSRSDVGYGVYDLYDLGEFNQKGAVRTKYGTKAQYLQAIQAAHAAGMQV
MK716   (49)   GTSRSDVGYGVYDLYDLGEFNQKGAVRTKYGTKAQYLQAIQAAHAAGMQV
TS-23   (51)   GTSQSDVGYGVYDLYDLGEFNQKGTIRTKYGTKTQYIQAIQAAKAAGMQV
K38     (49)   GNSQADVGYGAYDLYDLGEFNQKGTVRTKYGTKAQLERAIGSLKSNDINV 101                                                150
A 7-7  (100)   YGDVVMNHKGGADATEWVRAVEVNPSNRNQEVSGDYTIEAWTKFDFPGRG
S707   (100)   YGDVVMNHKGGADATEMVRAVEVNPNNRNQEVTGEYTIEAWTRFDFPGRG
LAMY   (100)   YGDVVMNHKGGADGTEMVNAVEVNRSNRNQEISGEYTIEAWTKFDFPGRG
BAA     (96)   YGDVVLNHKAGADATEDVTAVEVNPANRNQETSEEYQIKAWTDFRFPGRG
BLA     (98)   YGDVVINHKGGADATEDVTAVEVDPADRNRVISGEHRIKAWTHFHFPGRG
BStA    (99)   YADVVFDHKGGADGTEWVDAVEVNPSDRNQEISGTYQIQAWTKFDFPGRG
MK716   (99)   YADVVFDHKGGADGTEWVDAVEVNPSDRNQEISGTYQIQAWTKFDFPGRG
TS-23  (101)   YADVVFNHKAGADGTEFVDAVEVDPSNRNQETSGTYQIQAWTKFDFPGRG
K38     (99)   YGDVVMNHKMGADFTEAVQAVQVNPTNRWQDISGAYTIDAWTGFDFSGRN 151                                                200
A 7-7  (150)   NTHSNFKWRWYHFDGVDWDQSRQLQNRIYKFRGDGKGWDWEVDTENGNYD
S707   (150)   NTHSSFKWRWYHFDGVDWDQSRRLNNRIYKFRGHGKAWDWEVDTENGNYD
LAMY   (150)   NTHSNFKWRWYHFDGTDWDQSRQLQNKIYKFRGTGKAWDWEVDIENGNYD
BAA    (146)   NTYSDFKWHWYHFDGADWDESRK-ISRIFKFRGEGKAWDWEVSSENGNYD
BLA    (148)   STYSDFKWHWYHFDGTDWDESRK-LNRIYKFQG--KAWDWEVSNENGNYD
BStA   (149)   NTYSSFKWRWYHFDGVDWDESRK-LSRIYKFRGIGKAWDWEVDTENGNYD
MK716  (149)   NTYSSFKWRWYHFDGVDWDESRK-LSRIYKFRGIGKAWDWEVDTENGNYD
TS-23  (151)   NTYSSFKWRWYHFDGTDWDESRK-LNRIYKFRSTGKAWDWEVDTENGNYD
K38    (149)   NAYSDFKWRWFHFNGVDWDQRYQ-ENHIFRFAN--TNWNWRVDERNGNYD
```

FIG. 2B

```
              201                                                      250
A 7-7  (200)  YLMYADIDMDHPEVVNELRNWGVWYTNTLGLDGFRIDAVKHIKYSFTRDW
 S707  (200)  YLMYADIDMDHPEVVNELRNWGVWYTNTLGLDGFRIDAVKHIKYSFTRDW
 LAMY  (200)  YLMYADIDMDHPEVINELRNWGVWYTNTLNLDGFRIDAVKHIKYSYTRDW
  BAA  (195)  YLMYADVDYDHPDVVAETKKWGIWYANELSLDGFRIDAAKHIKFSFLRDW
  BLA  (195)  YLMYADIDYDHPDVAAEIKRWGTWYANELQLDGFRLDAVKHIKFSFLRDW
 BStA  (198)  YLMYADLDMDHPEVVTELKSWGKWYVNTTNIDGFRLDAVKHIKFSFFPDW
MK716  (198)  YLMYADLDMDHPEVVTELKNWGKWYVNTTNIDGFRLDAVKHIKFSFFPDW
TS-23  (200)  YLMFADLDMDHPEVVTELKNWGTWYVNTTNIDGFRLDAVKHIKYSFPPDW
  K38  (196)  YLLGSNIDFSHPEVQDELKDWGSWFTDELDLDGYRLDAIKHIPFWYTSDW 251                                                      300
A 7-7  (250)  LTHVRNTTGKNMFAVAEFWKNDIGAIENYLSKTNWNHSVFDVPLHYNLYN
 S707  (250)  INHVRSATGKNMFAVAEFWKNDLGAIENYLQKTNWNHSVFDVPLHYNLYN
 LAMY  (250)  LTHVRNTTGKPMFAVAEFWKNDLAAIENYLNKTSWNHSVFDVPLHYNLYN
  BAA  (245)  VQAVRQATGKEMFTVAEYWQNNAGKLENYLNKTSFNQSVFDVPLHFNLQA
  BLA  (245)  VNHVREKTGKEMFTVAEYWQNDLGALENYLNKTNFNHSVFDVPLHYQFHA
 BStA  (248)  LSDVRSQTGKPLFTVGEYWSYDINKLHNYIMKTNGTMSLFDAPLHNKFYT
MK716  (248)  LSYVRSQTGKPLFTVGEYWSYDINKLHNYITKTNGTMSLFDAPLHNKFYT
TS-23  (250)  LTYVRNQTGKNLFAVGEFWSYDVNKLHNYITKTNGSMSLFDAPLHNNFYT
  K38  (246)  VRHQRNEADQDLFVVGEYWKDDVGALEFYLDEMNWEMSLFDVPLNYNFYR 301                                                      350
A 7-7  (300)  ASRSGGNYDMRQIFNGTVVQRHPTHAVTFVDNHDSQPEEALESFVEEWFK
 S707  (300)  ASKSGGNYDMRNIFNGTVVQRHPSHAVTFVDNHDSQPEEALESFVEEWFK
 LAMY  (300)  ASNSGGYFDMRNILNGSVVQKHPIHAVTFVDNHDSQPGEALESFVQSWFK
  BAA  (295)  ASSQGGGYDMRRLLDGTVVSRHPEKAVTFVENHDTQPGQSLESTVQTWFK
  BLA  (295)  ASTQGGGYDMRKLLNSTVVSKHPLKAVTFVDNHDTQPGQSLESTVQTWFK
 BStA  (298)  ASKSGGTFDMRTLMTNTLMKDQPTLAVTFVDNHDTEPGQALQSWVDPWFK
MK716  (298)  ASKSGGAFDMRTLMTNTLMKDQPTLAVTFVDNHDTEPGQALQSWVDPWFK
TS-23  (300)  ASKSSGYFDMRYLLNNTLMKDQPSLAVTLVDNHDTQPGQSLQSWVEPWFK
  K38  (296)  ASQQGGSYDMRNILRGSLVEAHPMHAVTFVDNHDTQPGESLESWVADWFK 351                                                      400
A 7-7  (350)  PLAYALTLTRDQGYPSVFYGDYYGIPTHG---VPAMKSKIDPILEARQKY
 S707  (350)  PLAYALTLTREQGYPSVFYGDYYGIPTHG---VPAMRSKIDPILEARQKY
 LAMY  (350)  PLAYALILTREQGYPSVFYGDYYGIPTHG---VPSMKSKIDPLLQARQTY
  BAA  (345)  PLAYAFILTRESGYPQVFYGDMYGTKGTSPKEIPSLKDNIEPILKARKEY
  BLA  (345)  PLAYAFILTRESGYPQVFYGDMYGTKGDSQREIPALKHKIEPILKARKQY
 BStA  (348)  PLAYAFILTRQEGYPCVFYGDYYGIPQYN---IPSLKSKIDPLLIARRDY
MK716  (348)  PLAYAFILTRQEGYPCVFYGDYYGIPQYN---IPSLKSKIDPLLIARRDY
TS-23  (350)  PLAYAFILTRQEGYPCVFYGDYYGIPKYN---IPGLKSKIDPLLIARRDY
  K38  (346)  PLAYATILTREGGYPNVFYGDYYGIPNDN---ISAKKDMIDELLDARQNY
```

FIG. 2C

```
             401                                                450
A 7-7  (397) AYGKQNDYLDHHNMIGWTREGNTAHPNSGLATIMSDGPGGNKWMYVGRNK
 S707  (397) AYGKQNDYLDHHNIIGWTREGNTAHPNSGLATIMSDGAGGSKWMFVGRNK
 LAMY  (397) AYGTQHDYFDHHDIIGWTREGDSSHPNSGLATIMSDGPGGNKWMYVGKHK
  BAA  (395) AYGPQHDYIDHPDVIGWTREGDSSAAKSGLAALITDGPGGSKRMYAGLKN
  BLA  (395) AYGAQHDYFDHHDIVGWTREGDSSVANSGLAALITDGPGGAKRMYVGRQN
 BStA  (395) AYGTQHDYLDHSDIIGWTREGVTEKPGSGLAALITDGPGGSKWMYVGKQH
MK716  (395) AYGTQHDYLDHSDIIGWTREGVTEKPGSGLAALITDGPGGSKWMYVGKQH
 TS-23 (397) AYGTQRDYIDHQDIIGWTREGIDTKPNSGLAALITDGPGGSKWMYVGKKH
  K38  (393) AYGTQHDYFDHWDVVGWTREGSSSRPNSGLATIMSNGPGGSKWMYVGRQN 451                                                500
A 7-7  (447) AGQVWRDITGNRSGTVTINADGWGNFSVNGGSVSIWVNN-----------
 S707  (447) AGQVWSDITGNRTGTVTINADGWGNFSVNGGSVSIWVNK-----------
 LAMY  (447) AGQVWRDITGNRSGTVTINADGWGNFTVNGGAVSVWVKQ-----------
  BAA  (445) AGETWYDITGNRSDTVKIGSDGWGEFHVNDGSVSIYVQK-----------
  BLA  (445) AGETWHDITGNRSEPVVINSEGWGEFHVNGGSVSIYVQR-----------
 BStA  (445) AGKVFYDLTGNRSDTVTINSDGWGEFKVNGGSVSVWVPRKTTVSTIAWSI
MK716  (445) AGKVFYDLTGNRSDTVTINSDGWGEFKVNGGSVSVWVPRRPVN-------
 TS-23 (447) AGKVFYDLTGNRSDTVTINADGWGEFKVNGGSVSIWVAKTSNVTFTVNNA
  K38  (443) AGQTWTDLTGNNGASVTINGDGWGEFFTNGGSVSVYVNQ-----------

501                                                550
A 7-7  (486) --------------------------------------------------
 S707  (486) --------------------------------------------------
 LAMY  (486) --------------------------------------------------
  BAA  (484) --------------------------------------------------
  BLA  (484) --------------------------------------------------
 BStA  (495) TTRPWTDEFVRWTEPRLVAWP-----------------------------
MK716  (488) --------------------------------------------------
 TS-23 (497) TTTSGQNVYVVANIPELGNWNTANAIKMNPSSYPTWKATIALPQGKAIEF
  K38  (482) --------------------------------------------------

551                        588
A 7-7  (486) --------------------------------------
 S707  (486) --------------------------------------
 LAMY  (486) --------------------------------------
  BAA  (484) --------------------------------------
  BLA  (484) --------------------------------------
 BStA  (516) --------------------------------------
MK716  (488) --------------------------------------
 TS-23 (547) KFIKKDQAGNVIWESTSNRTYTVPFSSTGSYTASWNVP
  K38  (482) --------------------------------------
```

ALPHA-AMYLASE VARIANTS STABILIZED AGAINST DIMERIZATION AND/OR MULTIMERIZATION, METHOD FOR THE PRODUCTION THEREOF, AND DETERGENTS AND CLEANSERS CONTAINING THESE ALPHA-AMYLASE VARIANTS

CROSS-REFERENCE TO RELATED APPLICATIONS

This is a §365 continuation application of PCT/EP2005/010259 filed Sep. 22, 2005, which claims the priority of German patent application DE 10 2004 047 776.0, filed Oct. 1, 2004. Each of the foregoing applications is incorporated herein by reference.

FIELD OF THE INVENTION

The present invention relates to α-amylase variants which have been stabilized to a di- and/or multimerization brought about by electrostatic interactions, by means of point mutagenesis of surface amino acids, to methods of preparation thereof via mutagenesis of amino acid residues with a contribution to the electrostatic potential of the molecule and to detergents and cleansers containing these α-amylase variants.

BACKGROUND OF THE INVENTION

α-Amylases (E.C. 3.2.1.1) hydrolyze internal α-1,4-glycosidic bonds of starch and starch-like polymers with the formation of dextrins and β-1,6-branched oligosaccharides. They are very much among the industrially most important enzymes. Thus, for example, α-amylases are employed in the production of glucose syrup, for the treatment of raw materials in the manufacture of textiles, for the production of adhesives or for the production of sugar-containing food or food ingredients. Another important field of use is the use as an active component in detergents and cleansers.

Since detergents and cleansers have mainly alkaline pH values, particular use is made here of α-amylases that are active in alkaline medium. These types of α-amylases are produced and secreted by microorganisms, i.e. fungi or bacteria, especially those of the genera *Aspergillus* and *Bacillus*. Starting from these natural enzymes, there is now quite a vast abundance of variants available which have been derived via mutagenesis and have specific advantages depending on the field of use.

Examples thereof are the α-amylases of *Bacillus licheniformis, B. amyloliquefaciens* and *B. stearothermophilus* and their improved developments for the use in detergents and cleansers. The *B. licheniformis* enzyme is available from Novozymes under the name Termamyl® and from Genencor under the name Purastar® ST. Products of further development of this α-amylase can be obtained from Novozymes under the trade names Duramyl® and Termamyl® ultra, from Genencor under the name Purastar® OxAm and from Daiwa Seiko Inc., Tokyo, Japan, as Keistase®. The *B. amyloliquefaciens* α-amylase is sold by Novozymes under the name BAN®, and variants derived from the *B. stearothermophilus* α-amylase are sold under the names BSG® and Novamyl®, likewise by Novozymes.

Examples of α-amylases from other organisms are further developments of the *Aspergillus niger* and *A. oryzae* α-amylases, obtainable under the trade name Fungamyl® from Novozymes. Another commercial product is Amylase-LT®, for example.

Mention may further be made of the *Bacillus* sp. A 7-7 (DSM 12368) α-amylase disclosed in the application WO 02/10356 A2 and of the *B. agaradherens* (DSM 9948) cyclodextrin glucanotransferase (CGTase) described in the application WO 02/44350 A2. In addition, for example, the applications WO 03/002711 A2 and WO 03/054177 A2 define sequence spaces of α-amylases, all of which could be suitable in principle for corresponding applications.

The application DE 10309803.8, which has not been pre-published, for example, describes point mutations for improving the activity of said enzymes in alkaline medium. According to this application, amino acid substitutions suitable here are those in positions 13, 32, 194, 203, 230, 297, 356, 406, 414 and/or 474, according to the numbering of the unprocessed *B. amyloliquefaciens* α-amylase.—These positions are according to the numbering of the unprocessed *Bacillus* sp. A 7-7 (DSM 12368) α-amylase (WO 02/10356 A2) L13, T36, W198, S201, I208, A235, D302, D361, H408, K416 and N476, respectively, with the following, particularly effective substitutions: 13P, 32A, 194R, 197P, 203L, 230V, 297D, 356D, 406R, 414S and 474Q.

Another example of point mutagenesis on α-amylases is the application WO 00/22103 A1 which discloses polypeptides, inter alia also α-amylase variants, containing mutagenized surface amino acids. The purpose of this mutagenesis was to reduce the immunogenicity and/or allergenicity caused by these molecules.

Fusion products of α-amylases for the use in detergents and cleansers have also been described. Thus, for example, the application WO 96/23874 A1 discloses hybrids of the α-amylases of *Bacillus licheniformis, B. amyloliquefaciens* and *B. stearothermophilus*. According to the teaching of this application, such hybrid amylases may be prepared for determining the three-dimensional structure of said amylases, in order to use said structure for detecting important positions for enzymic activity. Further developments in this respect are the applications WO 97/41213 A1 and WO 00/60059 A2, which report numerous α-amylase variants whose respective performances have been improved. The application WO 03/014358 A2 discloses special hybrid amylases of *B. licheniformis* and *B. amyloliquefaciens*.

The three applications WO 96/23873 A1, WO 00/60060 A2 and WO 01/66712 A2, which are the basis of the commercial product Stainzyme® from Novozymes, constitute another important prior art. All the variants obtainable by point mutagenesis which are specified in each of these applications have altered enzymic properties and are therefore claimed or described for the use in detergents and cleansers. WO 96/23873 A1 makes mention of, in some cases two or more, point mutations in more than 30 different positions in four different wild type amylases. They apparently have altered enzymic properties with regard to thermal stability, oxidation stability and calcium dependence. They include point mutations in the following positions, each of which is stated with respect to the *Bacillus* sp. NCIB 12512 α-amylase: substitution of oxidizable amino acids in positions M9, M10, M105, M202, M208, M261, M309, M382, M430 or M440, preferably M91L; M10L; M105L; M202L,T,F,I,V; M208L; M261L; M309L; M382L; M430L and M440L; deletions of F180, R181, G182, T183, G184 and/or K185; and additionally the substitutions K269R; P260E; R124P; M105F,I,L,V; M208F,W,Y; L217I; V206I,L,F; Y243F; K108R; K179R; K239R; K242R; K269R; D163N; D188N; D192N; D199N; D205N; D207N; D209N; E190Q; E194Q or N106D.

The application WO 00/60060 A2 likewise specifies a multiplicity of possible amino acid substitutions in 10 different positions, on the basis of two very similar α-amylases from two different microorganisms, with the same numbering α-amylases AA349 and AA4560). These are the following sequence variations: R181*, G182*, D183*, G184*; N195A, R,D,C,E,Q,G,H,I,L,K,M,F,P,S,T,W,Y,V; 1206A,R,D,N,C,E, Q,G,H,L,K,M,F,P,S,T,W,Y,V; E212A,R,D,N,C,Q,G,H,I,L, K,M,F,P,S,T,W,Y,V; E216A,R,D,N,C,Q,G,H,I,L,K,M,F,P,S, T,W,Y,V; K269A,R,D,N,C,E,Q,G,H,I,L,M,F,P,S,T,W,Y,V; and/or R181A,N,D,C,E,Q,G,H,I,L,K,M,F,P,S,T,W,Y,V. This development too is against the background of improving performance via mutations.

WO 01/66712 A2, finally, refers to 31 different amino acid positions which are partially identical to the ones mentioned above and which have been mutated in either of the two α-amylases specified in the application WO 00/60060 A2 and which are said to improve aspects of both performance and stability. These are point mutations in the following positions: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471 and N484, again as defined via α-amylase AA560, i.e. also according to the numbering of the letter. Among these, the following variants are said to be particularly advantageous: Delta G184; Delta (R181-G182); Delta (D183-G184); R28N,K; S94K; R118K; N125A,R,K; N174D; R181Q,E,K; G186R; W189R,K; N195F; M202L,T; Y298H,F; N299A; K302R, S303Q, N306G,D,R,K; R310A, K,Q,E,H,D,N; N314D; R320K; H324K; E345R,D,K,N; Y396F; R400T,K; W439R; R444K; N445K,Q; K446N; Q449E; R458K; N471E and N484Q.

This latter application further describes polypeptide crystals, in particular those of enzymes, that might be improved with respect to their resolution capacity in that, in the molecules located next to the actual molecules of interest in the crystal in question and interacting therewith, those amino acids which are located within a distance of 6.0 Å to the polypeptide of interest could be mutated. This would apply in particular to Termamyl-like enzymes located next to other or identical Termamyl-like enzymes in a crystal; here in particular to a distance of less than 3.5 Å. This would concern positions 19, 20, 21, 22, 25, 28, 29, 53, 76, 84, 87, 90, 93, 94, 124, 125, 126, 128, 142, 144, 156, 157, 158, 159, 160, 161, 170, 171, 172, 173, 174, 175, 183, 184, 185, 186, 187, 188, 189, 190, 193, 195, 196, 197, 209, 212, 226, 229, 256, 257, 258, 259, 280, 281, 298, 299, 300, 302, 303, 304, 305, 306, 310, 311, 314, 319, 320, 321, 322, 341, 345, 405, 406, 408, 444, 447, 448, 449, 463, 464, 465, 466 and 467; and positions 22, 25, 28, 76, 94, 125, 128, 158, 160, 171, 173, 174, 184, 189, 209, 226, 229, 298, 299, 302, 306, 310, 314, 320, 345, 405, 447 and 466 for the shorter distance.

All of these applications regarding point mutagenesis share the fact that the point of stability is also evaluated under the aspect of a good performance in the corresponding field of use. This is because the stability maintained during storage and usage of α-amylases, for example within the context of detergent formulations, results in a high performance or in a performance as constantly high as possible with corresponding usage. An increase in stability, in particular to aggregate formation, above all in the course of workup, is not described.

The purpose of increasing stability is pursued by numerous applications describing special enzyme stabilizers. These additional ingredients cause a protein and/or enzyme present in corresponding agents to be protected from damage such as, for example, inactivation, denaturation or decay, particularly during storage. Thus, reversible protease inhibitors form a group of stabilizers. Others, for example polyols, stabilize to physical influences such as freezing, for example. Other polymeric compounds such as acrylic polymers and/or polyamides stabilize the enzyme preparation inter alia to pH fluctuations. Reducing agents and antioxidants increase stability of the enzymes to oxidative decay.

Compounds of these kind are added to the enzymes both during application and in the course of their work-up, which is particularly important, if a previously present stabilizer has been removed together with the other contaminations in a component step of said workup, for example a precipitation.

The prior art regarding the improvement in stability of α-amylases can be summarized as follows: a multiplicity of α-amylase variants have been developed via point mutagenesis, with the aim of these developments having mainly been that of improving the performance of said α-amylase variants. This category also includes those variants which have been stabilized with regard to denaturing agents such as bleaches or surfactants, since in these cases, the desired performance of the enzyme is optimized. In other cases, additional compounds which are overall referred to as stabilizers are mainly used for increasing stability or maintaining the physicochemical conformation.

A previously less regarded aspect in enzyme development is that of stabilizing the molecules per se in such a way that they have increased stability over the wild type molecule even during their workup. An additional advantageous effect thereof would be that this increased stability should also benefit the intended later usage of the enzyme in question.

The necessity for this is particularly evident in the case of α-amylases. At least some of these tend, especially during production and workup, to form multimers, specifically in the form of amorphous aggregates, which precipitate irreversibly. As a result, the activities in question are lost even during workup. The work-up process includes all steps of industrial production, starting from isolating the enzyme in question, in particular the fermentation media common in biotechnological production, via the following washing and separation steps (for example by precipitation) and concentration up to formulation, for example granulation. In particular, those substeps in which the enzyme is present in solutions with comparatively high concentrations are critical here, because, seen statistically, more frequent contacts occur here between the molecules than at lower concentrations. However, the aggregate formation may also occur during storage of α-amylase-containing agents or during application, for example when used as active ingredient in washing or cleaning processes.

This problem can go as far as individual α-amylases, although they can be produced and studied on a laboratory scale, refusing to be produced on an industrial scale with the aid of generally common methods. This is then also referred to as said enzymes having low process stability, meaning a large variety of possible processings and uses. For example, *Bacillus* sp. A 7-7 (DSM 12368) α-amylase exhibits a greater tendency toward multimerization than the native *B. licheniformis* α-amylase. Approaches to eliminate this type of instability, that is to say to reduce the tendency toward multimerization, would only enable such enzymes in the first place to be accessible to production on an industrial scale and thus to the large variety of fields of use in industrially relevant quantities.

SUMMARY OF THE INVENTION

It was therefore the object to stabilize α-amylases, in particular that of *Bacillus* sp. A 7-7 (DSM 12368), per se in such a way that they have, compared to the starting molecule, increased stability to aggregate formation.

In one partial aspect of said object, first a possible cause of their tendency toward aggregate formation, which is based on the structure of the enzymes in question, had to be determined. Subsequently, said cause was to be answered by suitable structural modifications.

Said structural modifications would firstly have an advantageous effect on the workup, i.e. industrial production, of said enzymes. Secondly, they should also be advantageous for the use of α-amylases, for example in detergents and cleansers, because this should additionally be accompanied by a constantly high activity during said use.

Particularly advantageous solutions to this object would therefore be considered to be those α-amylases which, besides said stability to aggregate formation, exhibit further positive properties with regard to their intended use, in particular with regard to their use in detergents and cleansers.

This applied especially to *Bacillus* sp. A 7-7 (DSM 12368) α-amylase. Preference is nonetheless given to those solutions which can be transferred to other α-amylases.

On the way to solve said object, the presence of areas with different electrostatic potential on the surface of α-amylases in their native, correctly folded globular structure was contemplated as a reason for the phenomenon of aggregate formation, which phenomenon is observed in particular with α-amylases, in particular with certain α-amylases. Thus, for example, large surface areas of *Bacillus* sp. A 7-7 (DSM 12368) α-amylase are negatively charged, while other, sometimes large areas have a positive or neutral electrostatic potential. Thus it is possible for a plurality of molecules, due to electrostatic interactions between the differently polarized or charged areas thereof, to assemble and thereby result in dimerization up to the formation of multimers. This interaction can be removed by the addition of denaturing agents presumably only with impairment of the globular structure, i.e. with the risk of irreversible inactivation. Secondly, said interaction per se may result in irreversibly inactive aggregates, in particular if the mutual attractor forces are strong enough in order to influence the molecular structure, even without intervention from the outside.

A molecular-biological approach is pursued in order to solve the object in question. The reason is that this influences the enzymic properties mediated by the mere amino acid sequence. In this connection, it was surprisingly found that modifications, i.e. point mutations which make the charge pattern on the surface of these molecules more similar to one another, counteract aggregate formation.

The amino acid residues present "on the surface of these molecules" can be defined by the 3D structure of the globular enzyme protein, the "Conolly surface" or the "accessibility" value, i.e. solvent accessibility (see below). The observed positive, negative or neutral contribution to the electrostatic potential of the molecule results from the chemical properties of the particular amino acid residues under the influence of the in each case next amino acid residues, in particular those below the surface, and may be calculated as illustrated below. The observed aggregation appears to occur in particular if a plurality of the residues immediately adjacent on the surface have the same plurality or charge.

Without wishing to be bound to this theory, it can be assumed that the formation of α-amylase aggregates, at least a significant part thereof, may be attributed to a di- and/or multimerization via differently polar and/or different charged surface areas of these protein molecules. As a result thereof, said molecules tend to align themselves in a regular orientation, similar to magnets. Breaking the two-dimensionality of the positively polarized or charged areas in favor of the predominant negative charge thus stabilizes the α-amylases to aggregate formation based on multimerization. This is beneficial both to isolation (for example in a precipitation step) and storage (for example in hydrophobic solvents, which promote an aggregation via polar regions) and to the usage.

This assumption is supported in that *B. licheniformis* α-amylase, in having a comparatively low tendency to multimerization, has a substantially negative charge potential on its surface.

Another advantageous effect, in addition to avoiding di- and/or multimerization, is the fact that, from a statistical point of view, the enzymes are mainly in their native conformation and are not deformed by said electrostatic interactions which result otherwise in target areas for said denaturing agents. This effect overall increases their stability, for example to organic solvents and surfactants which attach to and try to solubilize the hydrophobic areas which are usually less accessible to the solvent, or to proteases attacking the internal acid amide bonds of the backbone. Said effect also gives superior protection to internal oxidizable amino acid residues, for example against oxygen or bleaches.

The object in question is consequently solved by α-amylase variants having at least one amino acid substitution over the starting molecule, whereby at least one amino acid residue of the starting molecule, which is located on the surface of said molecule and makes a neutral or positively polar or charged contribution to the electrostatic potential of said molecule, has been replaced with a more negatively polar or negatively charged amino acid residue, with the following amino acid substitutions being possible:

```
Starting
amino
acid      to give

Arg (R)   K, Y, C, H, G, A, V, L, I, M, F, W, P, S, T, N, Q, E or D

Lys (K)   Y, C, H, G, A, V, L, I, M, F, W, P, S, T, N, Q, E or D

Tyr (Y)   C, H, G, A, V, L, I, M, F, W, P, S, T, N, Q, E or D

Cys (C)   H, G, A, V, L, I, M, F, W, P, S, T, N, Q, E or D

His (H)   G, A, V, L, I, M, F, W, P, S, T, N, Q, E or D

Gly (G)   A, V, L, I, M, F, W, P, S, T, N, Q, E or D

Ala (A)   V, L, I, M, F, W, P, S, T, N, Q, E or D
```

-continued

| Starting amino acid | to give |
|---|---|
| Val (V) | L, I, M, F, W, P, S, T, N, Q, E or D |
| Leu (L) | I, M, F, W, P, S, T, N, Q, E or D |
| Ile (I) | M, F, W, P, S, T, N, Q, E or D |
| Met (M) | F, W, P, S, T, N, Q, E or D |
| Phe (F) | W, P, S, T, N, Q, E or D |
| Trp (W) | P, S, T, N, Q, E or D |
| Pro (P) | S, T, N, Q, E or D |
| Ser (S) | T, N, Q, E or D |
| Thr (T) | N, Q, E or D |
| Asn (N) | Q, E or D |
| Gln (Q) | E or D |
| Glu (E) | D |

BRIEF DESCRIPTION OF THE FIGURES

FIG. 2: Alignment of *Bacillus* sp. A 7-7 (DSM 12368) α-amylase (SEQ ID NO. 2) with the most important other α-amylases of the prior art, in each case across the region of the mature protein, i.e., positions 32 to 516 according to SEQ ID NO. 2. Individual numbering can be carried out on the basis of the positional number indicated after the particular name of the first amino acid depicted in each case. These other listed α-amylases are S707 (*Bacillus* sp. #707 (SEQ ID NO. 3)), LAMY (*Bacillus* sp. KSM-AP1378 (SEQ ID NO. 4)), BAA (*Bacillus amyloliquefaciens* (SEQ ID NO. 5)), BLA (*Bacillus licheniformis* (SEQ ID NO. 6)), BStA (*Bacillus stearothermophilus* (SEQ ID NO. 7)), MK716 (*Bacillus* sp. MK716 (SEQ ID NO. 8)), TS-23 (*Bacillus* sp. TS-23 (SEQ ID NO. 9)) AND K38 (*Bacillus* sp. KSM-K38 (SEQ ID NO. 10)).

DETAILED DESCRIPTION

Figure 1:
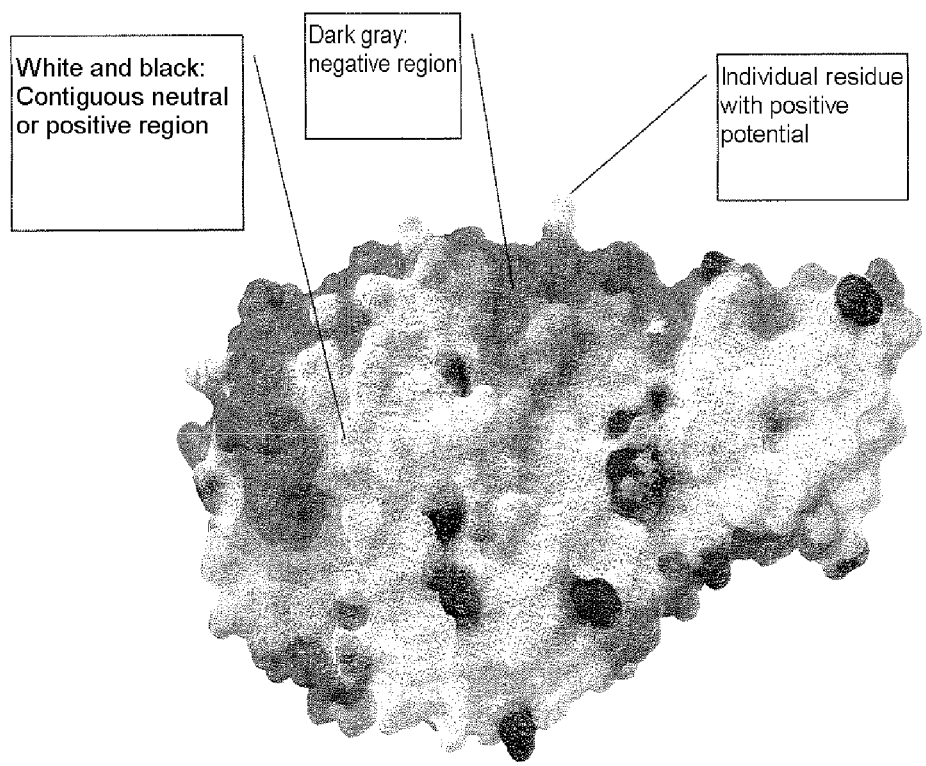
FIG. 1: Representation of the charge and polarity distribution on the Conolly surface of *Bacillus* sp. A 7-7 (DSM 12368) α-amylase (SEQ ID NO. 2). The image was generated with the aid of the Swiss-Pdb viewer (Swiss Institute of Bioinfomatics).
  Color Coding:
  gray: negative charge or polarization
  white: neutral charge or polarization
  black: positive charge or polarization
  The surface at the back of the molecule, which is not visible in this image and which also contains the active site, has a continuous negative charge pattern.

α-Amylases mean in accordance with the present application, as illustrated at the outset, the enzymes of class E.C. 3.2.1.1, which hydrolyze internal α-1,4-glycosidic bonds of starch and starch-like polymers with the formation of dextrins and β-1,6-branched oligosaccharides. The invention can in principle be applied to any known and still-to-be-found α-amylases, as long as they can be homologized with the α-amylase of *Bacillus* sp. A 7-7 (DSM 12368; SEQ ID NO. 2 of the present application). Such a homologization is depicted in FIG. 2 for the industrially most important α-amylases and allows or facilitates detecting the amino acid positions according to the invention in the other amylases. The invention is preferably applied to those α-amylases which are already employed successfully in industrial fields. Examples of α-amylase established in the prior art are given in the introduction.

α-Amylase variants are those α-amylases which have been derived from a precursor molecule by genetic modifications known per se. "Variant" is the term at the protein level, which corresponds to "mutant" at the nucleic acid level. The precursor or starting molecules may be wild type enzymes, i.e. those which are obtainable from natural sources. These have been introduced by way of example at the outset. They may also be enzymes which are already variants per se, i.e. which have already been modified compared to the wild type molecules. They mean, for example, point mutants, those with changes in the amino acid sequence, over several positions or longer contiguous regions, or else hybrid molecules which are composed of sections of various wild type α-amylases, which complement each other. Wild type enzymes as well as mutants and hybrid enzymes have been introduced by way of example at the outset. It is possible, according to the invention, to further develop in principle any α-amylases. If the nucleic acids encoding them are known, this is carried out by way of established methods of mutagenesis on the nucleic acids in question; if said nucleic acids are not known, it is possible to derive, on the basis of the amino acid sequence, nucleic acid sequences coding therefor and to modify the latter accordingly.

Amino acid substitutions mean substitutions of one amino acid by another amino acid. According to the invention, such substitutions are indicated with reference to the positions in which the substitution takes place, where appropriate in combination with the amino acids in question in the internationally customary one-letter code. "Substitution in position 83" means, for example, that a variant has a different amino acid in the position which has position 83 in the sequence of a reference protein. Such substitutions are usually carried out at the DNA level by way of mutations of individual base pairs (see above). "N83D" means, for example, that the reference enzyme has the amino acid asparagine at position 83, while the observed variant has the amino acid aspartic acid at the position homologizable therewith. "83D" means that any, i.e. usually a naturally predetermined, amino acid has been replaced with aspartic acid at a position corresponding to position 83; and "N83X" means that the amino acid asparagine in position 83 has been replaced with principally any other amino acid.

In principle, the amino acid substitutions according to the invention and specified by the present application are not limited to the fact that they are the only substitutions in which the variant in question differs from the wild type molecule. It is known in the prior art that the advantageous properties of individual point mutations can complement each other. An α-amylase optimized with respect to particular properties such as, for example, calcium binding or stability to surfactants may be developed according to the invention additionally by the substitutions presented herein. Therefore, embodiments of the present invention comprise any variants which have, in addition to other substitutions, also the substitutions according to the invention, compared to the wild type molecule.

A reference enzyme with respect to numbering of the positions, which may be considered according to the invention, is *Bacillus* sp. A 7-7 (DSM 12368) α-amylase whose nucleotide sequence is indicated in SEQ ID NO. 1, followed by the corresponding amino acid sequence in SEQ ID NO. 2. As illustrated in Example 1 of the present application, this sequence information has been corrected in comparison with the description in WO 02/10356 A2 in two positions, and in this form corresponds, according to the current knowledge, exactly to the sequence data obtainable from the deposited strain DSM 12368 described in WO 02/10356.

Said correct amino acid sequence is also revealed in the first lines of the alignment depicted in FIG. 1, which has been established only for the mature parts of the particular enzymes. This is justified by the fact that in vivo only the mature portion (i.e. that with the positive numbering in SEQ ID NO. 2) is active as α-amylase. or some enzymes such as, for example, AA349 and AA560, the patent literature (WO 00/60060 A2) indicates anyway merely the mature sequence parts.

The surface of the enzyme comprises all those amino acids of the natively folded enzyme which face the solvent. In *Bacillus* sp. A 7-7 (DSM 12368) α-amylase, for example, these are the 407 amino acids listed in detail in Example 2.

The surface amino acids of other α-amylases may in principle be obtained by using the alignment of FIG. 2. This is true only approximately, however. Highly conserved and structurally secured regions such as .alpha.-helices or .beta.-sheets usually produce good agreement; in more flexible regions, in particular loops, the comparison based on the alignment, i.e. the primary structure, is uncertain. In all cases (if known), the secure X-ray structure, as it is actually deposited meanwhile for most commercially important .alpha.-amylases in generally accessible databases, is decisive. Said databases are, for example, Gel Bank (National Center for Biotechnology Information NCBI, National Institutes of health, Bethesda, Md., USA) and Swiss-Prot (Geneva Bioinformatics (GeneBio) S.A., Geneva, Switzerland).

If the 3D (or tertiary) structure has not yet been determined for a molecule of interest, the former may be obtained via homology modeling. This method of predicting the structure of proteins whose crystal structures have not yet been resolved assumes that proteins having a similar primary structure also have similar secondary and tertiary structures. The similarity of two protein sequences can be determined via a suitable algorithm, for example BLAST, FASTA or CLUSTAL. Such algorithms are likewise available via generally accessible protein databases; thus, for example, GenBank and Swiss-Prot have corresponding links. The RSCB protein database (accessible via Max-Delbruck-Zentrum in Berlin, Germany) enables the user to find for a particular sequence crystal structures of related proteins by way of a FASTA search.

The possible calculations based thereupon, for example with the aid of the "Swiss-Pdb Viewer", are described in the publication "SWISS-Model and the Swiss-PdbViewer: An environment for comparative protein modeling" (1997) by N. Guex and M. C. Peitsch in Electrophoresis, Vol. 18, pp. 2714 to 2723. Said viewer and its corresponding manual is accessible free of charge from the organization Swiss Institute of Bioinformatics (Central Administration, Batiment Ecole de Pharmacie—room 3041, Universite de Lausanne, 1015 Lausanne, Switzerland). Superimposition of said structures can establish a leader structure onto which the protein sequence of the α-amylase of interest is then modeled. The individual steps for this can be found in said user manual.

All of the depictions of the surface of an enzyme discussed herein, i.e. the special listing of the surface amino acids of *Bacillus* sp. A 7-7 (DSM 12368) α-amylase (cf. FIG. 1) as well as the modeling approaches illustrated, are based on a calculation. This involves rolling by way of calculation a probe of 1.4 Å in size over the surface of said protein. All positions contacted thereby are included in the area of contact with said probe and thus in the surface; relatively narrow clefts which are theoretically open toward the outside are not regarded here as part of the surface but are classed as belonging to the interior of the molecule. Using this approach produces the "Connolly surface" which was first described by M. L. Connolly in the article "Solvent-Accessible Surfaces of Proteins and Nucleic Acids" (1983) in *Science*, volume 221, 709-713. This acknowledged method is familiar to the skilled worker and is used according to the invention for defining the surface of α-amylases.

In this way, the mentioned 407 surface amino acids were produced for *Bacillus* sp. A 7-7 (DSM 12368) α-amylase, which are listed in detail in Example 2.

The amino acid residues relevant to the invention, which are located on the surface of the α-amylases contemplated, are those making a neutral or positively polar or charged contribution to the electrostatic potential of the molecule at pH 7. Such a contribution to the electrostatic potential of the molecule is defined as the proportion of the individual amino acid having charges greater than or equal to zero.

The electrostatic potential at a particular point on the surface is defined, using the abovementioned Connolly surface, as the potential which acts on the designated probe. This electrostatic potential which theoretically is present at any site of the surface may be calculated by suitable algorithms, and for this purpose the following considerations are made according to the invention:

The electric field can be considered in principle as the sum of the electric subfields generated by the individual charges. For a useful calculation, the individual charges are considered point charges in a first approximation. The electric field $E_i$ of a point charge $Q_i$ can be determined in vacuo at the site $r_i$ via the following equation (1), where $\in_0$ is the dielectric constant:

$$\overline{E}_i = \frac{1}{4\pi\varepsilon_0} \frac{Q_i}{r_i^2} \hat{r}_i \quad (1)$$

A group of N charges thus results in the following electric field E:

$$\overline{E} = \sum_{i=1}^{N} \frac{1}{4\pi\varepsilon_0} \frac{Q_i}{r_i^2} \hat{r}_i \quad (2)$$

The Coulomb potential $V_c(P_1)$ generated therefrom at point $P_1$ in the electric field E is then defined as follows, where L is the coordinate space:

$$V_c(P_1) = \int_{\infty}^{P_1} \overline{E} \cdot d\overline{L} \quad (3)$$

This equation can be interpreted in words approximately as follows: the electrostatic potential at point $P_1$ is defined as the difference in potentials of a point at infinity and point $P_1$. L is a position vector which in practice represents the integration variable of space. Point $P_1$, and consequently also any other relevant point introduced to this calculation in the same manner, is on the protein surface. This formula enables computers to determine the particular local electrostatic potential for each point on the protein surface, using suitable computer programs. As a result, a corresponding charge or polarity can be assigned to each amino acid residue, and this can be illustrated by way of a visual representation as in FIG. 1, for example.

The calculation using this equation (3) produces an approximation of the electrostatic potential, which is not accurate but sufficient according to the invention. In a first approximation, the dielectric constant $\varepsilon_0$ must be replaced with the actual dielectric constant $\varepsilon = \varepsilon_0 * \varepsilon_r$ as the dielectric constant of the medium. This approach is referred to as "Screened Coulomb Potential" and is described by S. A. Hassa et al. (2002) in the article "A Critical Analysis of Continuum Electrostatics: The Screened Coulomb Potential-implicit Solvent Model and the Study of the Alanine Dipeptide and Discrimination of Misfolded Structures of Proteins", in *Proteins*, volume 45, page 47. Several examples of further, more accurate algorithms can be found in the literature, such as E. L. Mehler et al. (1991), "Electrostatic effects in proteins: comparison of dielectric and charge models", Protein Eng., volume 8, pages 903-910, and A. Jakalian et al. (2002), "Fast, efficient generation of high-quality atomic charges. AM1-BCC model: II. Parameterization and validation" in *J. Comput. Chem.*, volume 16, pages 1623-1641. These, however, are not required for the application described herein, since ultimately a semiquantitative statement (positive, neutral, negative) allows the problem to be solved.

The amino acids in question may be calculated, for example, by a computer algorithm which is available as a further module of the Swiss PDB viewer mentioned above. This enables the surface charge distribution of the molecule studied to be calculated by way of the items "tools", "compute molecular surface" and "electrostatic potential", with the partial charges of the atoms of each amino acid, except hydrogen atoms, being taken into account under standard parameters.

As a result of this, 118 residues making a positive or neutral contribution to the electrostatic potential of the surface were determined as a subset of the previously determined 407 surface amino acid residues of *Bacillus* sp. A 7-7 (DSM 12368) α-amylase, as illustrated in example 2.

In order to indicate the substitutions allowed in each case, the polarity values or charges which the various amino acid side chains possess per se are contemplated. This results in the following order: R, as the most basic and normally positively charged amino acid side chain, followed by K, Y, C, H, G, A, V, L, I, M, F, W, P, S, T, N, Q, E and D, with D being the most acidic amino acid side chain which carries a negative charge at neutral pH. This explains the grades indicated above, and the structure of the molecule and other charge effects can be assumed according to the invention to play virtually no part in the substitution of individual surface amino acids. Thus, if one of said amino acid side chains were to carry a slightly more negative or slightly more positive partial charge than expected from the well-known values for the free amino acid, then it can be assumed according to the invention that an amino acid side chain listed further down said order carries a correspondingly slightly more negative or slightly more positive partial charge in the same molecular environment, and the order stated here of the amino acids allowed for substitution is not altered overall.

The illustration in FIG. 1 depicts the pattern, calculated according to example 2, of different polarities and charges on a surface of *Bacillus* sp. A 7-7 (DSM 12368) α-amylase. The back of the molecule which is not visible there and which also comprises the active site, has a negative charge pattern throughout. This explains the relative ease with which dimers can form in which a molecule having a positively polarized or charged surface, as depicted in FIG. 1, attaches to the negatively charged/polarized surface located at the back of another molecule and thereby blocks the latter's active site. It should be possible to recognize such dimers by a molecular weight twice as high and/or an amylase activity half as high in relation to the total protein concentration, in each case in comparison with a corresponding solution containing monomers. With increasing attachment of further molecules in the same orientation, the activity of corresponding solutions should decrease further, until a proportion of the enzymes which has aggregated enough finally precipitates as an amorphous precipitate and has finally been denatured and rendered useless.

From a statistical point of view, α-amylase variants of the invention should undergo this process less frequently, according to the number and location of the substitutions carried out according to the invention.

In a preferred embodiment, α-amylase variants of the invention are those in which said amino acid residue has an accessibility of at least 10%, preferably at least 20%, particularly preferably at least 30%, prior to amino acid substitution, wherein said accessibility of the amino acid residue in question is calculated on a scale from 0% (not accessible to the solvent) to 100% (present in a hypothetical pentapeptide, GGXGG).

Accessibility of an amino acid residue means according to the invention, how well said residue is accessible to the surrounding solvent (usually water), with the molecule being in its natural conformation. Determination of this physicochemical property is based on a scale from 0 to 100%, with a value of 0% accessibility meaning that the residue in question is not accessible to the solvent, and 100% being the accessibility possible in a hypothetical pentapeptide GGXGG.

According to the invention, this molecular property is reflected in that an exposed amino acid residue which stands out from the surface contacts other molecules more readily than one which is less accessible to the solvent. Such residues are therefore preferred targets for the conversion according to the present invention.

Using the abovementioned SwissPDB Viewer enables these values also to be calculated for each surface amino acid of a globular protein. Accessibility of the amino acids is calculated there via the menu item "Select→Accessible aa", followed by entering the accessibility in percent. Subsequently, the corresponding amino acids are selected and can be displayed by pressing the "Return" key. In addition, it is possible here to automate said calculation via a self-build program, and this is particularly recommended, if more amino acids are to be included in said calculation.

As illustrated in Example 2, the following 97 amino acid residues of *Bacillus* sp. A 7-7 (DSM 12368) α-amylase were determined, which make a contribution to the electrostatic potential of the surface and at the same time have a value for accessibility of at least 10%, the values for solvent accessibility being indicated in % in brackets following the positions listed:

T5 (39), N6 (12), G7 (13), N19 (28), N22 (28), N25 (16), R26 (27), R28 (39), S29 (38), S32 (28), N33 (28), K35 (37), K37 (18), Q53 (12), K72 (27), V75 (30), R76 (24), T81 (16), R82 (22), N83 (44), Q84 (24), Q86 (18), A87 (18), T90 (30), A91 (11), K93 (32), S94 (50), N95 (19), G96 (25), Q98 (29), R118 (41), T136 (22), K142 (30), G149 (14), N150 (39), T151 (22), H152 (27), N154 (41), K156 (30), R158 (33), Y160 (20), R171 (32), Q172 (53), R176 (41), R181 (34), R218 (18), T227 (19), G229 (14), K242 (15), R247 (20), T251 (23), R254 (15), K259 (26), N260 (49), K281 (33), N283 (40), R302 (50), R310 (31), R320 (52), T323 (49), R359 (13), Y368 (12), Y372 (37), T376 (56), K383 (19), K385 (37), Q394 (20), K395 (38), G399 (16), K400 (44), Y404 (11), G417 (11), N418 (25), T419 (59), A420 (37), H421 (16), P422 (46), G435 (25), G436 (17), W439 (47), R444 (49), N445 (41), Q449 (31), V450 (24), R452 (33), R458 (24), S459 (52), G460 (32), T461 (35), T463 (40), N465 (22), A466 (37), N471 (20), S473 (10), N475 (25), G476 (31), N484 (12).

The further preferred embodiments of this molecule with respect to accessibility can be selected on the basis of the specified percentage accessibility.

An application to other α-amylases is possible by way of approximation via an alignment such as in FIG. 2. However, as illustrated previously, the actual three dimensional structure is decisive, on the basis of which the appropriate calculations of actual charge distribution and solvent accessibility can be carried out, as demonstrated for *Bacillus* sp. A 7-7 (DSM 12368) α-amylase in the example.

In a further preferred embodiment, α-amylase variants of the invention are those α-amylase variants, wherein said amino acid residue is located in a neutral or positively polarized or charged region consisting of at least two directly adjacent amino acid residues on the surface.

This thus involves carrying out the calculation illustrated above and selecting for the mutagenesis of the invention an amino acid of the kind that, in addition to the abovementioned properties, is immediately adjacent to just such a residue on the surface, i.e. it is not surrounded exclusively by those amino acid residues which cannot also undergo a substitution according to the invention.

Thus, an amino acid of the kind that is not on its own but part of a neutral or positively polar or charged surface of the molecule is hereby subjected to a mutation according to the invention. This breaks the two-dimensional arrangement which, as explained above, may in particular be regarded as the cause for α-amylases to aggregate via electrostatic interactions and form multimers. From a statistical point of view, an isolated positive charge or polarity should make a smaller contribution to multimerization, since it should have a smaller effect on other molecules due to increasingly more negatively charged adjacent amino acids. Therefore preference is given to carrying out substitutions in contiguous regions which appear neutral or positive. These are depicted in black or white for the example of *Bacillus* sp. A 7-7 (DSM 12368) α-amylase in FIG. 1.

In a further preferred embodiment, α-amylase variants of the invention are those α-amylase variants, wherein the amino acid residue to be mutated according to the invention is located in a position belonging to either of the following two groups:

(A) 5, 6, 7, 19, 22, 25, 26, 28, 29, 32, 33, 35, 37, 53, 72, 75, 76, 81, 82, 83, 84, 86, 87, 90, 91, 93, 94, 95, 96, 98, 118, 136, 142, 149, 150, 151, 152, 154, 156, 158, 160, 171, 172, 181, 227, 229, 247, 251, 254, 259, 260, 281, 283, 394, 395, 399, 400, 417, 418, 419, 420, 421 and 422; or (B) 435, 436, 439, 444, 445, 449, 450, 452, 458, 459, 460, 461, 463, 465, 466, 471, 473, 475, 476 and 484, in each case indicated in the numbering of the mature protein according to SEQ ID NO. 2.

As described in example 3, it was possible to accurately model the surface charge distribution of *Bacillus* sp. A 7-7 (DSM 12368) α-amylase. It turned out that it is possible to classify the 97 amino acid residues located on the surface of the molecule and making a neutral or positively polar or charged contribution to the electrostatic potential of said molecule and additionally having an accessibility of more than 10% into three groups depending on their location. In this connection, the residues of groups A and B are in each case contiguous regions of neutral or positive polarity or charge.

Group A refers to the following 63 amino acid positions, wherein in each case the amino acid present there in *Bacillus* sp. A 7-7 (DSM 12368) α-amylase is indicated:

T5, N6, G7, N19, N22, N25, R26, R28, S29, S32, N33, K35, K37, Q53, K72, V75, R76, T81, R82, N83, Q84, Q86, A87, T90, A91, K93, S94, N95, G96, Q98, R118, T136, K142, G149, N150, T151, H152, N154, K156, R158, Y160, R171, Q172, R181, T227, G229, R247, T251, R254, K259, N260, K281, N283, Q394, K395, G399, K400, G417, N418, T419, A420, H421, P422.

Group B includes the following 20 positions:
G435, G436, W439, R444, N445, Q449, V450, R452, R458, S459, G460, T461, T463, N465, A466, N471, S473, N475, G476, N484.

The remaining 14 amino acid residues which form group C may be considered neutral or positive islands within otherwise negative polarized or charged regions:
R176 (41), R218 (18), K242 (15), R302 (50), R310 (31), R320 (52), T323 (49), R359 (13), Y368 (12), Y372 (37), T376 (56), K383 (19), K385 (37), Y404 (11).

The last-mentioned amino acid residues can be assumed to make a rather small contribution to the aggregation tendency of the whole molecule. The contiguous regions A and B should cause multimerization all the more because they should exert a stronger electrostatic effect which causes the arrangement of a plurality of molecules and which, as assumed according to the invention, results in the observed tendency to aggregate. Therefore preference is given to carrying out the amino acid substitutions of the invention in said contiguous regions A and/or B.

The same considerations and calculations as in the example of *Bacillus* sp. A 7-7 (DSM 12368) α-amylase may be carried out in principle for any other α-amylase established in the prior art. Mention should be made, in particular in the case of these specific positions, of the more simple comparison of the corresponding amino acid sequences via an alignment. In order to implement the aspect of the invention described herein, the particular α-amylases can be homologized with *Bacillus* sp. A 7-7 (DSM 12368) α-amylase. Such an alignment is indicated, for example, in FIG. 2 for the most important α-amylases established in the prior art; the numbering of the mature protein according to SEQ ID NO. 2 corresponds to line 1 in FIG. 2. The positions listed here, which are preferred for the substitutions of the invention, can be derived by way of such an alignment for the enzyme of interest in each case and can be modified according to the invention with at least approximately the same success as for the enzyme looked at herein. As explained above, however, the specific situation in the enzyme in question is ultimately decisive in each case.

In a further preferred embodiment, the α-amylase variants of the invention are those α-amylase variants, wherein a plurality of said amino acid substitutions have been carried out, preferably at least 2, 3, 4, 5, 6, 7, 8, 9, 10, 11, 12, 13, 14, 15, 16, 17, 18, 19, 20, 21, 22, 23, 24, 25, 26, 27, 28, 29 or 30, particularly preferably between 10 and 30, and very particularly preferably between 15 and 25.

This is because the solution to the present object is based on the observation that some α-amylases form amorphous aggregates, and the existence of relatively large, differently charged or polarized two-dimensional regions was considered a possible explanation for this. At the same time, α-amylases having mainly negative surface charges are known in the prior art. It is therefore advantageous to convert according to the invention even more than only one residue to a more negatively polar or negatively charged amino acid residue.

Due to the nature of the enzymes, this procedure also has an individual upper limit which must be determined experimentally, where appropriate. Thus, a molecule that is covered with too many negative charges is likely to be repelled too much by the substrate and thereby lose activity. Moreover, too many charges may also be disadvantageous for the folding so that, from a critical value upward, too many misfolded, and therefore non-active, molecules would be formed.

At least for *Bacillus* sp. A 7-7 (DSM12368) α-amylase, it has therefore proved to be advantageous to limit the number of substitutions according to the invention to less than 30, of which more than 10 can be regarded as really advantageous. A similar result can be expected for the α-amylases homologizable therewith, for example those of FIG. 2 and in particular those which likewise bear neutral or positively charged or polarized amino acids in the homologous positions.

In a further preferred embodiment, α-amylase variants of the invention are those α-amylase variants in which in from at least one to no more than exactly as many other positions one or more other amino acid residues on the surface of the starting molecule have been replaced with less negatively polar or negatively charged amino acid residues, with in each case the following amino acid substitutions being possible:

| Starting amino acid | to give |
|---|---|
| K, Y, C, H, G, A, V, L, I, M, F, W, P, S, T, N, Q, E or D | Arg (R) |
| Y, C, H, G, A, V, L, I, M, F, W, P, S, T, N, Q, E or D | Lys (K) |
| C, H, G, A, V, L, I, M, F, W, P, S, T, N, Q, E or D | Tyr (Y) |
| H, G, A, V, L, I, M, F, W, P, S, T, N, Q, E or D | Cys (C) |
| G, A, V, L, I, M, F, W, P, S, T, N, Q, E or D | His (H) |
| A, V, L, I, M, F, W, P, S, T, N, Q, E or D | Gly (G) |
| V, L, I, M, F, W, P, S, T, N, Q, E or D | Ala (A) |
| L, I, M, F, W, P, S, T, N, Q, E or D | Val (V) |
| I, M, F, W, P, S, T, N, Q, E or D | Leu (L) |
| M, F, W, P, S, T, N, Q, E or D | Ile (I) |
| F, W, P, S, T, N, Q, E or D | Met (M) |
| W, P, S, T, N, Q, E or D | Phe (F) |
| P, S, T, N, Q, E or D | Trp (W) |
| S, T, N, Q, E or D | Pro (P) |
| T, N, Q, E or D | Ser (S) |
| N, Q, E or D | Thr (T) |
| Q, E or D | Asn (N) |
| E or D | Gln (Q) |
| D | Glu (E) |

This mutation which runs counter to the actual invention attenuates again the charge effect introduced according to the invention. This pursues two aims: firstly, as mentioned above, it is possible, in particular if a plurality of mutations of the invention are carried out (up to 30 are considered particularly sensible according to the invention), for the α-amylase molecule to receive a negative charge which is too high overall and which therefore could impair stability and reactivity. In this respect, in particular if a plurality of mutations are carried out, it may be reasonable for the overall charge effect to be attenuated again.

Secondly, this breaks the two-dimensionality of the charge distribution on the surface of the enzyme. As illustrated above, said two-dimensionality was considered an essential reason for multimerization. If the charge pattern is altered to give a looser pattern with overall the same or only slightly changed total charge, the tendency to aggregate can likewise be assumed to decrease because the molecules do no longer align themselves automatically in a regular orientation, like magnets.

The substitutions allowed in each case are designated by falling back to the reflection illustrated above on the polarity values or charges which the various amino acid side chains possess per se. This results in the exactly reverse order because R, as the most basic and normally positively charged amino acid side chain, cannot be replaced with any other to cause a more positive polarity or charge, but can itself replace any other side chain. This applies, in a corresponding grading, to K, Y, C, H, G, A, V, L, I, M, F, W, P, S, T, N, Q, E and D, with D being the most acidic amino acid side chain which normally carries a negative charge at neutral pH and which can be replaced with any other side chain, including E, under this aspect of the invention.

In a further preferred embodiment, the α-amylase variants of the invention are those α-amylase variants, wherein the substitution(s) carried out in order to reduce the change in the overall charge have been carried out at amino acid position(s) which does/do not belong to the following:

(A) 5, 6, 7, 19, 22, 25, 26, 28, 29, 32, 33, 35, 37, 53, 72, 75, 76, 81, 82, 83, 84, 86, 87, 90, 91, 93, 94, 95, 96, 98, 118, 136, 142, 149, 150, 151, 152, 154, 156, 158, 160, 171, 172, 181, 227, 229, 247, 251, 254, 259, 260, 281, 283, 394, 395, 399, 400, 417, 418, 419, 420, 421 and 422 or (B) 435, 436, 439, 444, 445, 449, 450, 452, 458, 459, 460, 461, 463, 465, 466, 471, 473, 475, 476 and 484 or (C) 176, 218, 242, 302, 310, 320, 323, 359, 368, 372, 376, 383, 385 and 404, in each case indicated in the numbering of the mature protein according to SEQ ID NO. 2.

This preferred embodiment makes use of the finding for *Bacillus* sp. A 7-7 (DSM 12368) α-amylase (SEQ ID NO. 2), according to which these amino acid residues which can be assigned to regions A and B form large areas of neutral or positively polarized or charged regions, and the residues listed under (C) form neutral or positively polarized or charged islands within a mainly negative environment. Since, as illustrated above, the aspect of the invention contemplated here intends to break especially the two-dimensionality of charge distribution, it is particularly useful to select positions other than the ones designated herein for the charge-leveling back mutation. This is because this would again enlarge the neutrally or positively polarized or charged regions specified.

In a further preferred embodiment, α-amylase variants of the invention are those α-amylase variants wherein the starting molecule is any of the following α-amylases: α-amylase from *Bacillus* sp. A 7-7 (DSM 12368) (SEQ ID NO. 2), α-amylase from *Bacillus* sp. #707 (SEQ ID NO. 3), α-amylase from *Bacillus* sp. KSM-AP1378 (SEQ ID NO. 4), α-amylase from *Bacillus* sp. KSM-K38 (SEQ ID NO. 10), α-amylase from *B. amyloliquefaciens* (SEQ ID NO. 5), α-amylase from *B. licheniformis* (SEQ ID NO. 6), α-amylase from *Bacillus* sp. MK716 (SEQ ID NO. 8), α-amylase from *Bacillus* sp. TS-23 (SEQ ID NO. 9), α-amylase from *B. stearothermophilus* (SEQ ID NO. 7), α-amylase from *B. agaradherens*, a cyclodestrin glucanotransferase (CGTase) from *B. agaradherens*, in particular, from *B. agaradherens* (DSM 9948), or a hybrid amylase therefrom and/or an α-amylase derived therefrom by mutagenesis of single or multiple amino acids.

As illustrated at the outset, numerous α-amylases are established in the prior art for the use for various industrial purposes. These include, for example, fungal and bacterial enzymes. The present invention may in principle be applied to all of these α-amylases.

Those α-amylases of Gram-positive bacteria, in particular of the genus *Bacillus*, which are adapted to an alkaline environment, are particularly common for industrial purposes. This is because they have favorable properties for these fields of use from the outset. Accordingly, the present invention is directed in particular to the α-amylases which can be obtained naturally from said species. These include in particular the following:

*Bacillus* sp. A 7-7 (DSM 12368) α-amylase, disclosed in WO 02/10356 A2 and the present application (SEQ ID NO. 2);

*Bacillus* sp. #707 α-amylase (SEQ ID NO. 3), disclosed in the publication "Nucleotide sequence of the maltohexaose-producing amylase gene from an alkalophilic *Bacillus* sp. #707 and structural similarity to liquefying type α-amylases" (1988) by Tsukamoto et al., *Biochem. Biophys. Res. Comm.*, Vol. 151(1), pp. 25-31;

*Bacillus* sp. KSM-AP1378 α-amylase (SEQ ID NO. 4), whose amino acid sequence (together with point mutants) has been disclosed in EP 985731 A1;

*Bacillus* sp. KSM-K38 α-amylase (SEQ ID NO. 10), disclosed in EP 1022334 A2;

*B. amyloliquefaciens* α-amylase (SEQ ID NO. 5) (commercial product BAN® from Novozymes);

*B. licheniformis* α-amylase (SEQ ID NO. 6) (commercial product Termamyl® from Novozymes);

*Bacillus* sp. MK716 α-amylase (SEQ ID NO. 8), whose sequence has been deposited under number AAB18785 in the database of the National Center for Biotechnology Information, National Library of Medicine, Building 38A, Bethesda, Md. 20894, USA (GenBank);

*Bacillus* sp. TS-23 α-amylase (SEQ ID NO. 9), disclosed in the publication: "Production and property of raw-starch-degrading Amylase from the thermophilic and alkaliphilic *Bacillus* sp. TS-23" (1998) by Lin et al. in *Biotechnol. Appl. Biochem.*, Vol. 28(1), pp. 61 to 68; and

*B. stearothermophilus* α-amylase (SEQ ID NO. 7) (commercial product Novamyl® from Novozymes).

The amino acid sequences comprising the, in each case, mature regions of these enzymes are compiled in FIG. 2.

The present invention further relates to *B. agaradherens* α-amylase and two *B. agaradherens* cyclodextrin glucanotransferases (CGTases), which are described in two international applications: WO 02/06508 A2 and WO 02/44350 A2, the latter being formed by the deposited microorganism *B. agaradherens* (DSM 9948) described in the application in question and being preferred. The part of the CGTase molecule, which can be homologized with the previously described α-amylases, is in each case modified according to the invention.

The starting enzyme to be introduced to the invention may also be a hybrid amylase of the α-amylases just mentioned. These are revealed, as already mentioned at the outset, by the applications WO 96/23784 A1 (hybrids of the α-amylases of *Bacillus licheniformis* (SEQ ID NO. 6), *B. amyloliquefaciens* (SEQ ID NO. 5) and *B. stearothermophilus* (SEQ ID NO. 7))

and WO 03/014358 A2 (special hybrid amylases of *Bacillus licheniformis* (SEQ ID NO. 6) and *B. amyloliquefaciens* (SEQ ID NO. 5). The latter will be discussed in more detail hereinbelow.

In addition, the prior art describes numerous α-amylase variants derived by mutagenesis of single or multiple amino acids of said α-amylases. The present invention may likewise be applied to all of these, and the respective effects can be assumed in principle to be additive. Thus it should be possible, by carrying out a mutation of the invention, to improve an α-amylase variant which is particularly powerful in a special field of application, owing to a particular amino acid substitution, also in its tendency to aggregate, in addition to the former aspect of its performance. These are thus preferably amino acid variations for which a corresponding advantage has been described previously.

In this connection, it does not matter in principle, in which order the substitutions in question have been carried out, i.e. whether a corresponding point mutant is further developed according to the invention or initially a variant of the invention is generated, for example, from a wild type molecule and is then further developed according to other teachings which can be found in the prior art. It is also possible to carry out a plurality of substitutions, for example those according to the invention and others together, in a single mutagenesis mix simultaneously. This situation is given, for example, if an α-amylase is further developed using randomly acting mutagenesis processes, for example by means of mutagenizing agents or shuffling. This applies to any type of modification of the enzymes in question, in particular to point mutations which in principle act independently of one another.

Particularly powerful α-amylases obtainable by point mutations are revealed, for example, by the application WO 00/60060 A2 which describes, on the basis of the AA560 amylase (the same numbering as the mature protein in SEQ ID NO. 2), numerous mutations in positions 181, 182, 183, 184, 195, 206, 212, 216, and 269. This application can be considered a development of WO 96/23873 A1 which had previously described the possibility of point mutagenesis in positions 180, 181, 182, 183, 184 and 185 in order to improve performance. The application WO 00/60059 A2 specifies further improvements of enzymes referred to therein as Termamyl-like amylases; according to this, positions 13, 48, 49, 50, 51, 52, 53, 54, 57, 107, 108, 111, 168 and 197 (according to the numbering of *B. licheniformis* α-amylase) are said to be suitable starting points for this. All of these α-amylases which are improved with respect to their activity and/or performance via these positions and in particular according to said applications, are, for the purposes of the present application, starting molecules particularly preferred according to the invention.

In particularly preferred embodiments, the starting molecule is any of the following α-amylases: α-amylase from *Bacillus* sp. A 7-7 (DSM 12368) (SEQ ID NO. 2), cyclodextrin glucanotransferase from *B. agaradherens* (DSM 9948) or a hybrid amylase of the α-amylases from *B. amyloliquefaciens* (SEQ ID NO. 5) and from *B. licheniformis* (SEQ ID NO. 6), preferably a hybrid amylase AL34, AL76, AL112, AL256, ALA34-84, LAL19-153 or LAL19-433.

Thus the invention described herein is illustrated in the examples of the present application in particular on the basis of *Bacillus* sp. A 7-7 (DSM 12368) α-amylase (SEQ ID NO. 2), whose most likely correct DNA and amino acid sequences are indicated in the sequence listing of the present application. This wild type enzyme has the advantages illustrated in the application WO 02/10356 A2 with regard to a use in detergents and cleansers over other established α-amylases.

Another particularly preferred starting molecule, namely *B. agaradherens* (DSM 9948) cyclodextrin glucanotransferase, has already been mentioned above and likewise makes particular contributions to the overall performance of detergents and cleansers over other enzymes, as described in the application WO 02/44350 A2.

The application WO 03/014358 describes hybrid amylases of the α-amylases *B. amyloliquefaciens* and *B. licheniformis*. Of these, the molecules referred to by the acronyms AL34, AL76, AL112, AL256, ALA34-84, LAL19-153 or LAL19-433 have exhibited particularly advantageous performances when used in detergents and cleansers and are therefore particularly preferably also introduced to the present invention, i.e. are mutated according to the invention. The particular names refer to the elements of which they are composed in each case, as seen from the N terminus, wherein A is the *B. amyloliquefaciens* α-amylase and L is the *B. licheniformis* α-amylase and the subsequent number indicates the junction between the first and second amino acid sequences. Further details on this can be found in said application.

In a further preferred embodiment, α-amylase variants of the invention are those α-amylase variants, wherein the starting molecule is an α-amylase whose amino acid sequence is at least 96% identical, preferably 98%, particularly preferably 100%, identical to the amino acid sequence indicated in SEQ ID NO. 2 in positions +1 to 484.

This *Bacillus* sp. A 7-7 (DSM 12368) α-amylase is described in detail in the international application WO 02/10356 A2 which has already been mentioned several times. It should be noted in this context that the nucleotide sequence and the amino acid sequence derived therefrom of the α-amylase obtainable from said strain have most likely the sequences indicated in SEQ ID NO. 1 and 2, respectively, of the present application. This represents a correction of the sequence indicated in the application WO 02/10356 A2. The experiments described in that application have also been carried out using the native α-amylase obtainable from said strain.

The nucleotide sequence according to SEQ ID NO. 1 enables the skilled worker immediately to carry out mutations according to the invention. An α-amylase-encoding DNA which has been prepared according to the sequence listing of WO 02/10356 A2 rather than by using the deposited microorganism, may be converted with the aid of simple point mutagenesis methods, as they are also mentioned in the examples of the present application, to a nucleotide sequence according to SEQ ID NO. 1 of the present application.

The possibilities of culturing the corresponding microorganism, purification and enzymic characterization of the wild type α-amylase have likewise been disclosed in that application and are summarized again in Example 1 of the present application. Variants according to the invention of this enzyme can in principle be produced and purified in the same way, with the differences introduced according to the invention, for example in view of the isoelectric point (IEP), having to be taken into account. For example, the IEP could be shifted into the acidic range somewhat.

Further preference is given to those α-amylase variants according to the invention, wherein the starting molecule is an α-amylase variant containing, with increasing preference, 1, 2, 3, 4, 5, 6, 7, 8, 9, 10 or 11 additional point mutations.

The sequences indicated in SEQ ID NO. 1 and 2 differ in each case in two positions from the information in WO 02/10356 A2, as illustrated in Example 1. According to current knowledge, they represent the best descriptions of *Bacillus* sp. A 7-7 (DSM 12368) α-amylase and are therefore particularly preferred starting points for introducing amino acid substitutions of the invention.

According to the above, it may further be assumed that in principle any α-amylase can be improved by individual point mutations, i.e. deletions, insertions or substitutions of individual amino acids, with respect to other aspects. Thus, as already illustrated at the outset, the applications WO 00/22103 A1, WO 96/23873 A1, WO 00/60060 A2 and WO 01/66712 A2 reveal α-amylase variants which have been mutagenized in individual positions and which have been improved in each case with respect to special aspects. Since some of said variants have high homology to said amylase depicted in SEQ ID NO. 2, i.e. they can be referred to as highly related, the substitutions specified therein can be expected to be applicable also to these molecules and, analogously, also to other α-amylases, with the same advantageous effects. Further possible modifications can be found in the prior art as summarized, for example, at the outset of the present application.

Furthermore preferred embodiments of the present invention are α-amylase variants according to the invention, having the additional point mutations in one or more of the following positions: 5, 167, 170, 177, 202, 204, 271, 330, 377, 385 and 445, according to the numbering of the mature protein according to SEQ ID NO. 2.

Thus, the German application DE 10309803.8 which has not been prepublished reveals that point mutations may be carried out in positions −19, 5, 167, 170, 177, 204, 271, 330, 377, 385 and/or 445 (or 13, 32, 194, 197, 203, 230, 297, 356, 406, 414 and 474 according to the numbering of the unprocessed B. amyloliquefaciens α-amylase), in order to improve the alkali activity of α-amylases. Preference is therefore given to applying the present invention to these already improved molecules.

The application WO 94/18314 A1 reveals α-amylase variants stabilized to oxidation, including especially in position 197 (according to the numbering of B. licheniformis α-amylase) corresponding to position 202 of the α-amylase according to SEQ ID NO. 2. Variants according to the invention may be stabilized additionally to oxidation by the substitutions mentioned therein, especially in position 202. Said substitution is of particular interest also because M202 in Bacillus sp. A 7-7 (DSM 12368) α-amylase is the only methionine residue which is more than 10% accessible to the solvent, having an accessibility value of 30% (cf. Example 2). This explains its particular sensitivity to oxidation and the connection with the present invention.

Preferred embodiments thereof are those α-amylase variants, wherein the point mutations in the starting enzymes are as follows: 5A, 167R, 170P, 177L, 202L, 204V, 271D, 330D, 377R, 385S and/or 445Q.

Thus, the mentioned application DE 10309803.8 describes the sequence variations −19P, 5A, 167R, 170P, 177L, 204V, 271D, 330D, 377R, 385S and/or 445Q (or, according to the numbering of the unprocessed B. licheniformis α-amylase, the substitutions to give 13P, 32A, 194R, 197P, 203L, 230V, 297D, 356D, 406R, 414S and 474Q) as preferred substitutions.

WO 94/18314 A1 illustrates in particular the oxidation-stabilizing action of the substitution M197L corresponding to the amino acid substitution M202L according to SEQ ID NO. 2. Variants according to the invention may therefore be stabilized additionally to oxidation particularly by this point mutation.

Another subject matter of the present invention are methods of increasing the stability of an α-amylase to a dimerization and/or multimerization brought about by electrostatic interactions, whereby at least one amino acid residue on the surface of the starting molecule, which makes a neutral or positively polar or charged contribution to the electrostatic potential of said molecule, is replaced with a more negatively polar or negatively charged amino acid residue, with the following amino acid substitutions being possible:

```
Starting
amino
acid     to give

Arg (R)  K, Y, C, H, G, A, V, L, I, M, F, W, P, S, T, N, Q, E or D

Lys (K)  Y, C, H, G, A, V, L, I, M, F, W, P, S, T, N, Q, E or D

Tyr (Y)  C, H, G, A, V, L, I, M, F, W, P, S, T, N, Q, E or D

Cys (C)  H, G, A, V, L, I, M, F, W, P, S, T, N, Q, E or D

His (H)  G, A, V, L, I, M, F, W, P, S, T, N, Q, E or D

Gly (G)  A, V, L, I, M, F, W, P, S, T, N, Q, E or D

Ala (A)  V, L, I, M, F, W, P, S, T, N, Q, E or D

Val (V)  L, I, M, F, W, P, S, T, N, Q, E or D

Leu (L)  I, M, F, W, P, S, T, N, Q, E or D

Ile (I)  M, F, W, P, S, T, N, Q, E or D

Met (M)  F, W, P, S, T, N, Q, E or D

Phe (F)  W, P, S, T, N, Q, E or D

Trp (W)  P, S, T, N, Q, E or D

Pro (P)  S, T, N, Q, E or D

Ser (S)  T, N, Q, E or D
```

| Starting amino acid | to give |
|---|---|
| Thr (T) | N, Q, E or D |
| Asn (N) | Q, E or D |
| Gln (Q) | E or D |
| Glu (E) | D |

According to the invention, the tendency to form amorphous α-amylase aggregates is understood as meaning the formation of dimers, trimers or aggregates from more individual α-amylase molecules. This is understood as being a stability aspect, since this causes the enzyme preparation in question from a macroscopic point of view, as illustrated at the outset, to lose a considerable proportion of activity. Any method that counteracts aggregation is therefore one that increases the stability of the enzyme preparation in question with respect to its overall activity.

The approach according to the invention in order to solve said problem consists of, as likewise illustrated above, restricting the multimerization brought about by electrostatic interactions. This is carried out by altering the charges and polarity carriers on the α-amylase surface in the direction of less neutral or less positive polarities, i.e. to rather negative polarities and charges. Preference is given here, as illustrated above and reiterated hereinbelow, to substitutions in particular regions and particular positions.

Methods of preparing enzyme variants are known per se to a biotechnologist. He will use in particular the nucleic acids coding for the starting enzymes in question, which is mutated in the corresponding codon according to the amino acid to be introduced.

The principle of this is also illustrated in Example 3: primers which cover the region to be mutated and contain the mutation to be introduced (mismatch primers) are synthesized, for example, with the aid of the QuikChange kit (Stratagene, cat. No. 200518) according to the corresponding protocol. The primer sequences are designed on the basis of the corresponding nucleotide sequence, taking into account the universal genetic code. In order to generate a less neutral or positive polarity or charge as already discussed above, the correspondingly graded amino acid substitutions are possible in this context. According to this principle, an expression vector containing the α-amylase sequence is suitably mutagenized accordingly and transformed into an expression strain suitable for expressing said amylase, using generally known methods. Since the variant usually has only a few substitutions compared to the starting molecule, the systems established for said starting molecule can be used for information when choosing the expression system, culturing and work-up methods. The fact that the electrostatic properties of α-amylases are altered according to the invention must be taken into account here. A corresponding change in the IEP may be checked, for example, with the aid of isoelectric focusing.

Other than that, the comments made above regarding the particular enzymes apply accordingly. This also applies accordingly to the preferred embodiments, i.e. to those methods of the invention which are used to obtain the above-described variants according to the invention.

According to the above, preferred methods of the invention are those, wherein said amino acid residue has an accessibility of at least 10%, preferably at least 20%, particularly preferably at least 30%, prior to amino acid substitution, wherein said accessibility of the amino acid residue in question is calculated on a scale from 0% (not accessible to the solvent) to 100% (present in a hypothetical pentapeptide, GGXGG).

According to the above, further preferred methods of the invention are those, wherein said amino acid residue is located in a neutral or positively polarized or charged region consisting of at least two directly adjacent amino acids residues on the surface.

In this context and according to the above, preference is given to methods, wherein said amino acid residue is in a position belonging to either of the following two groups:

(A) 5, 6, 7, 19, 22, 25, 26, 28, 29, 32, 33, 35, 37, 53, 72, 75, 76, 81, 82, 83, 84, 86, 87, 90, 91, 93, 94, 95, 96, 98, 118, 136, 142, 149, 150, 151, 152, 154, 156, 158, 160, 171, 172, 181, 227, 229, 247, 251, 254, 259, 260, 281, 283, 394, 395, 399, 400, 417, 418, 419, 420, 421 and 422; or (B) 435, 436, 439, 444, 445, 449, 450, 452, 458, 459, 460, 461, 463, 465, 466, 471, 473, 475, 476 and 484, in each case indicated in the numbering of the mature protein according to SEQ ID NO. 2.

According to the above, further preferred methods of the invention are those, wherein a plurality of said amino acid substitutions are carried out, preferably at least 2, 3, 4, 5, 6, 7, 8, 9, 10, 11, 12, 13, 14, 15, 16, 17, 18, 19, 20, 21, 22, 23, 24, 25, 26, 27, 28, 29 or 30, particularly preferably between 10 and 30 and very particularly preferably between 15 and 25.

According to the above, further preferred methods of the invention are those, according to which in from at least one to no more than exactly as many other positions one or more other amino acid residues on the surface of the starting molecule have been replaced with less negatively polar or negatively charged amino acid residues, with in each case the following amino acid substitutions being possible:

| Starting amino acid | to give |
|---|---|
| K, Y, C, H, G, A, V, L, I, M, F, W, P, S, T, N, Q, E or D | Arg (R) |
| Y, C, H, G, A, V, L, I, M, F, W, P, S, T, N, Q, E or D | Lys (K) |

-continued

| Starting amino acid | to give |
|---|---|
| C, H, G, A, V, L, I, M, F, W, P, S, T, N, Q, E or D | Tyr (Y) |
| H, G, A, V, L, I, M, F, W, P, S, T, N, Q, E or D | Cys (C) |
| G, A, V, L, I, M, F, W, P, S, T, N, Q, E or D | His (H) |
| A, V, L, I, M, F, W, P, S, T, N, Q, E or D | Gly (G) |
| V, L, I, M, F, W, P, S, T, N, Q, E or D | Ala (A) |
| L, I, M, F, W, P, S, T, N, Q, E or D | Val (V) |
| I, M, F, W, P, S, T, N, Q, E or D | Leu (L) |
| M, F, W, P, S, T, N, Q, E or D | Ile (I) |
| F, W, P, S, T, N, Q, E or D | Met (M) |
| W, P, S, T, N, Q, E or D | Phe (F) |
| P, S, T, N, Q, E or D | Trp (W) |
| S, T, N, Q, E or D | Pro (P) |
| T, N, Q, E or D | Ser (S) |
| N, Q, E or D | Thr (T) |
| Q, E or D | Asn (N) |
| E or D | Gln (Q) |
| D | Glu (E) |

It is in principle unimportant here, whether the substitution according to the invention or this charge-leveling substitution is carried out first.

In this context and according to the above, preference is given to methods, wherein the substitution(s) carried out in order to reduce the change in the overall charge have been carried out at amino acid position(s) which does/do not belong to the following:

(A) 5, 6, 7, 19, 22, 25, 26, 28, 29, 32, 33, 35, 37, 53, 72, 75, 76, 81, 82, 83, 84, 86, 87, 90, 91, 93, 94, 95, 96, 98, 118, 136, 142, 149, 150, 151, 152, 154, 156, 158, 160, 171, 172, 181, 227, 229, 247, 251, 254, 259, 260, 281, 283, 394, 395, 399, 400, 417, 418, 419, 420, 421 and 422 or
(B) 435, 436, 439, 444, 445, 449, 450, 452, 458, 459, 460, 461, 463, 465, 466, 471, 473, 475, 476 and 484 or
(C) 176, 218, 242, 302, 310, 320, 323, 359, 368, 372, 376, 383, 385 and 404, in each case indicated in the numbering of the mature protein according to SEQ ID NO. 2.

According to the above, further preferred methods of the invention are those wherein the starting molecule is any of the following α-amylases: α-amylase from *Bacillus* sp. A 7-7 (DSM 12368) (SEQ ID NO. 2), α-amylase from *Bacillus* sp. #707 (SEQ ID NO. 3), α-amylase from *Bacillus* sp. KSM-AP1378 (SEQ ID NO. 4), α-amylase from *Bacillus* sp. KSM-K38 (SEQ ID NO. 10), α-amylase from *B. amyloliquefaciens* (SEQ ID NO. 5), α-amylase from *B. licheniformis* (SEQ ID NO. 6), α-amylase from *Bacillus* sp. MK716 (SEQ ID NO. 8), α-amylase from *Bacillus* sp. TS-23 (SEQ ID NO. 9), α-amylase from *B. stearothermophilus* (SEQ ID NO. 7), α-amylase from *B. agaradherens*, a cyclodestrin glucanotransferase (CGTase) from *B. agaradherens*, in particular, from *B. agaradherens* (DSM 9948), or a hybrid amylase therefrom and/or an α-amylase derived therefrom by mutagenesis of single or multiple amino acids.

Among these, preference is given according to the above two methods wherein the starting molecule is any of the following α-amylases: α-amylase from *Bacillus* sp. A 7-7 (DSM 12368) (SEQ ID NO. 2), cyclodestrin glucanotransferase from *B. agaradherens* (DSM 9948) or a hybrid amylase of the α-amylases from *B. amyloliquefaciens* (SEQ ID NO. 5) and from *B. licheniformis* (SEQ ID NO. 6), preferably a hybrid amylase AL34, AL76, AL112, AL256, ALA34-84, LAL19-153 or LAL19-433.

According to the above, further preferred methods of the invention are those, wherein the starting molecule is an α-amylase whose amino acid sequence is at least 96% identical, preferably 98%, particularly preferably 100%, identical to the amino acid sequence indicated in SEQ ID NO. 2 in positions +1 to 485.

Among these, preference is given according to the above to methods, wherein the starting molecule is an α-amylase variant containing, with increasing preference, 1, 2, 3, 4, 5, 6, 7, 8, 9, 10 or 11 additional point mutations.

According to the above, further preferred methods of the invention are those, wherein the introduced α-amylase is an α-amylase variant having the additional point mutations in one or more of the following positions: 5, 167, 170, 177, 202, 204, 271, 330, 377, 385 and 445, according to the numbering of the mature protein according to SEQ ID NO. 2.

At this point, it should be noted once again that it does not matter in principle for mutants which can be used as starting molecules according to the invention, as to whether the amino acid substitution according to the invention takes place after or before introducing the other substitutions disclosed in the prior art.

Among said methods, preference is given according to the above to methods, wherein the point mutations are as follows: 5A, 167R, 170P, 177L, 202L, 204V, 271D, 330D, 377R, 385S and/or 445Q.

The present invention further relates to nucleic acids coding for any of the above-described α-amylase variants according to the invention.

Said nucleic acids are understood as meaning both RNA and DNA molecules and also DNA analogs, both the coding and the codogenic strand, that is in every reading frame, because it is possible, for example, to utilize the teaching associated with the invention, in order to regulate corresponding α-amylases via an interfering corresponding RNA or to increase the lifetime of said genetic information by converting it to a DNA analog which is more slowly degradable in vivo. To a certain extent, said nucleic acids present the molecular-biological dimension to the present invention, as is discernible from the subject matters of the invention set forth hereinbelow. According to the above, they are preferred accordingly.

Said nucleic acids are understood as meaning preferably DNA molecules because they can be used for preparing and/or, where appropriate, further modifying the α-amylase variants of the invention by molecular-biological methods known per se. The nucleotide sequences of the abovementioned α-amylases established in the prior art are deposited in well-known databases (for example Genbank or Swissport; see above) or are revealed in said publications. These sequences are accordingly preferred starting points for introducing point mutations according to the invention.

Starting points for said nucleic acid may also be the sequence information indicated in the sequences, in particular for derivatives of Bacillus sp. A 7-7 (DSM 12368) α-amylase. Another alternative consists of preparing total DNA of particular microorganisms considered for this and isolating the endogenous α-*amylase* genes by PCR. Primers which may be employed in principle are the 5' and 3' sequence sections which can likewise be read from SEQ ID NO. 1.

The pure protein-encoding sections may, for example, also be mutagenized by a PCR, i.e. their sequence may be modified according to the invention. To this end, a PCR with a corresponding statistical error rate is carried out, the PCR product is cloned and the introduced mutations are verified by subsequent sequencing.

Preference is given here to a nucleic acid which derives from a nucleic acid according to SEQ ID NO. 1 or from a variant thereof having increasingly preferred 1, 2, 3, 4, 5, 6, 7, 8, 9, 10 and 11 additional point mutations to give those mutations resulting in any of the amino acid substitutions according to the invention as defined above, by which are meant those mutations by which at least one amino acid residue on the surface of the starting molecule, which makes a neutral or positively polar or charged contribution to the electrostatic potential of said molecule has been replaced to give a more negatively polar or negatively charged amino acid residue, meaning the stated ranking of the allowed amino acid substitutions or the leveling substitutions described at from at least one to no more than exactly as many other positions of one or more other amino acid residues on the surface of the starting molecule to give less negatively polar or negatively charged amino acid residues, meaning the correspondingly opposite ranking of the allowed amino acid substitutions.

This is because, as explained above, various point mutations can be introduced into α-amylase molecules, which can exert advantageous actions in principle independently of one another. Thus it is possible to carry out substitutions according to the invention on those molecules which have been improved in particular with respect to special performance aspects, stability or, for example, allergenicity. They include in particular also non-inventive point mutations. This approach of generating in the end amino acid substitutions according to the invention is based on the corresponding nucleic acids, and the order in which these various mutations are carried out is in principle technically irrelevant here.

The present invention further relates to vectors which comprise a previously specified nucleic acid of the invention.

This is because, in order to handle the nucleic acids relevant to the invention and to carry out in particular the methods of the invention therewith and to prepare the production of proteins of the invention, they are suitably ligated into vectors. Such vectors and the corresponding methods are described in detail in the prior art. A large number and variety of vectors are commercially available, both for cloning and for expression. These include, for example, vectors derived from bacterial plasmids, from bacteriophages or from viruses, or mainly synthetic vectors. They are further distinguished by the nature of the cell types in which they are able to establish themselves, for example according to vectors for Gram-negative, Gram-positive bacteria, for yeasts or for higher eukaryotes. They are suitable starting points, for example for molecular-biological and biochemical studies, for mutagenesis of the nucleic acid sections present therein and for expression of the gene in question or the corresponding protein. They are virtually indispensable, in particular for preparing constructs for deleting or enhancing expression, as is revealed by the relevant prior art.

Vectors are particularly suitable for making sequence variations according to the invention, for example via site-directed mutagenesis, as illustrated in Example 3.

In one embodiment, vectors according to the invention are cloning vectors.

This is because cloning vectors are suitable for molecular-biological characterization of *the* gene of interest, in addition to its storage, biological amplification or selection. At the same time, they are transportable and storable forms of the claimed nucleic acids and are also starting points for molecular-biological techniques not associated with cells, such as, for example, PCR or in vitro mutagenesis methods.

It is possible, for example, to convert a cloning vector carrying *the* gene for an α-amylase described in the prior art to a cloning vector of the invention by carrying out a mutation according to the invention.

Vectors according to the invention are preferably expression vectors.

This is because such expression vectors are the basis of establishing the corresponding nucleic acids in biological production systems and thereby producing the corresponding proteins, since they enable the gene product in question to be transcribed and translated, i.e. synthesized, in vivo. Preferred embodiments of this subject matter of the invention are expression vectors that carry the genetic elements required for expression, for example the natural promoter originally located upstream of said gene or a promoter from a different organism. These elements may be arranged, for example, in the form of an "expression cassette". Alternatively, individual or all regulatory elements may also be provided by the particular host cell. Particular preference is given to expression vectors tuned to the chosen expression system, in particular the host cell (see below), with respect to further properties, such as, for example, optimal copy number.

Providing an expression vector is usually the best option for amplifying a protein according to the invention, preferably in combination with coacting proteins according to the invention, and thus increasing the activity in question or making it available to quantitative preparation.

A separate subject matter of the invention are cells which, after genetic modification, comprise any of the previously specified nucleic acids of the invention.

This is because said cells contain genetic information for the synthesis of a protein according to the invention and are used in the method of the invention, if the α-amylases in question are obtained biotechnologically. Said cells are understood as meaning in particular those cells which have been provided with the nucleic acids of the invention by methods known per se or which derived from such cells. This involves selecting suitably those host cells which can be cultured in a comparatively simple manner and/or deliver high yields of product.

They enable, for example, the corresponding genes to be amplified, or else mutagenesis thereof, if an in vivo metagenesis method is carried out, or transcription and translation, and ultimately biotechnological production of the proteins in question. Said genetic information may be present either extrachromosomally as a separate genetic element, i.e. located on a plasmid in the case of bacteria, or integrated in a chromosome. The choice of a suitable system depends on problems such as, for example, type and duration of storage of said gene, or of the organism or the type of mutagenesis or selection. Such possible implementations are known to the molecular biologist.

This also explains the preferred embodiment, according to which said nucleic acid in such a cell is part of a vector, in particular part of an above-described vector of the invention.

This is because the above-described advantages in handling, storage, expression etc., of the nucleic acid in question are associated therewith.

Among these cells, preference is in each case given to a host cell that is a bacterium, in particular one that secretes the α-amylase variant formed into the surrounding medium.

This is because bacteria are characterized by short generation times and low demands on culturing conditions. This enables inexpensive methods to be established. Moreover, there is plenty of variable experience regarding bacteria in fermentation technology. Gram-negative or Gram-positive bacteria may be suitable for a special production for very different reasons which may be determined experimentally in the individual case, such as nutrient sources, rate of product formation, time required, etc.

An additional advantageous embodiment relates to the fact that most industrially important α-amylases have originally been found as enzymes secreted by the relevant microorganisms, in particular bacteria, into the surrounding medium. This is because they are usually digestive enzymes in vivo. Accordingly, it is advantageous if the industrially produced enzymes of the invention are likewise secreted into the surrounding medium, since they can be worked up therefrom without cell disruption and therefore comparatively easily. This may be achieved, for example, by adding appropriate sequences to *the* genes in question—if these are not present anyway—that code for a leader peptide which causes the cell in question to export them. An alternative in Gram-negative bacteria, for example, consists of partially opening the outer membrane to release proteins, as described, for example, in the application WO 01/81597 A1.

In a preferred embodiment, the bacterium is a Gram-negative bacterium, in particular one of the genera *Escherichia coli, Klebsiella, Pseudomonas* or *Xanthomonas*, in particular *E. coli* K12, *E. coli* B or *Klebsiella planticola* strains, and very particular derivatives of the strains *Escherichia coli* BL21 (DE3), *E. coli* RV308, *E. coli* DH5α, *E. coli* JM109, *E. coli* XL-1 or *Klebsiella planticola* (Rf).

This is because these species and strains are established in the prior art for molecular-biological procedures and biotechnological production processes. They are moreover available via generally accessible strain collections such as the Deutsche Sammlung von Mikroorganismen and Zellkulturen GmbH, Mascheroder Web 1b, 38124 Braunschweig, Germany or from commercial sources. In addition, they can be optimized for specific production conditions in combination with other components such as, for example, vectors, which are likewise available in large numbers.

Gram-negative bacteria such as, for example, *E. coli* secrete a multiplicity of proteins into the periplasmic space. This may be advantageous for special applications. There are, as mentioned, also processes known, by which Gram-negative bacteria too export the expressed proteins.

In an alternative embodiment which is no less preferred, the bacterium is a Gram-positive bacterium, in particular one of the genera *Bacillus, Staphylococcus* or *Corynebacterium*, very particularly of the species *Bacillus lentus, B. licheniformis, B. amyloliquefaciens, B. subtilis, B. globigii* or *B. alcalophilus, Staphylococcus carnosus* or *Corynebacterium glutamicum*, and among these in turn, very particularly preferably a *B. licheniformis* DSM 13 derivative.

This is because Gram-positive bacteria are fundamentally different from Gram-negative ones in that secreted proteins are immediately released into the nutrient medium surrounding the cells, from which medium the expressed proteins according to the invention can be purified directly, if desired. Moreover, they are related to most source organisms for industrially important enzymes or are identical thereto and usually produce themselves comparable enzymes so that they have a similar codon usage and their protein synthesis apparatus is by nature geared thereto accordingly. *B. licheniformis* DSM 13 which characterizes a very particularly preferred embodiment is likewise a very common biotechnological producer strain in the prior art.

Another embodiment of the present invention consists of methods of producing an above-described α-amylase variant.

The, in a narrower sense inventive, methods of increasing the stability of an α-amylase to multimerization brought about by electrostatic interactions have already been described above. They refer primarily to molecular-biological steps in order to generate such variants in the first place. The methods defined at this point, which are in a wider sense likewise inventive, are those which are industrially required in order to produce quantitative amounts of the α-amylase variants of the invention. Thus they primarily refer to biotechnological methods of producing variants according to the invention—apart from the rather only theoretically relevant chemical synthesis of said enzymes. Said methods usually involve microorganism strains which, by applying molecular-biological techniques known per se, have been enabled to produce α-amylase variants which in the course of the present invention have been acknowledged as being advantageous according to the invention.

The method of the invention, which has been illustrated and which is based in particular on mutagenesis, may thus be introduced as a characterizing section into an established biotechnological method of producing α-amylases, i.e. may be combined with such a method.

The formation of a protein in question in a strain employed for production is detected by way of enzymic detection of the enzyme activities in question by detection reactions known per se for α-amylase activity. For detection at the molecular-biological level, the proteins depicted in the present sequence listing can be synthesized by customary methods and antibodies can be raised thereto. These proteins can then be detected, for example, via appropriate Western blots. Said antibodies react particularly preferably to those surface regions which have been modified according to the invention, since the latter can be distinguished from the non-inventive variants.

The aim of these methods is to deliver the α-amylases in question to their particular applications. To this end, any work-up, purification and formulation steps established in biotechnology can be used. These include, for example, the method of refining concentrated enzyme solutions, described in the application WO 2004/067557 A1, which is chromatography-based and which consequently can also be applied successfully to amylase preparations. Said method is the basis of the application DE 10360841.9 which has not been prepublished and according to which the solutions in question which have been obtained inter alia by a chromatographic step can be processed further to give enzyme granules. Further method aspects which may likewise be combined advantageously with the present invention are revealed in the applications DE 102004021384.4 and DE 192004019528 which have likewise not been prepublished and according to which the storage stability and abrasion resistance of such granules can be increased by incorporating glycerol or 1,2-propanediol or by a special coating.

Said methods, in particular their component steps, in which the enzyme preparation is still in a liquid form, are improved according to the invention by the fact that the present α-amylase variant according to the invention is less prone to aggregation via electrostatic interactions, resulting in a smaller loss of total activity. This enables, for example, α-amylase granules to be produced which contain a higher proportion of active substances.

The production methods are preferably methods which are carried out using an above-specified nucleic acid of the invention, preferably using a previously specified vector of the invention and particularly preferably using a previously specified cell of the invention.

This is because said nucleic acids, in particular the nucleic acids specified in the sequence listing, make available the correspondingly preferred genetic information in a microbiologically usable form, i.e. genetic engineering production processes. Increasing preference is given to providing said nucleic acids on a vector which can be utilized particularly successfully by the host cell, or such cells themselves. The production processes in question are known per se to the skilled worker.

Embodiments of the present invention may also be, on the basis of the corresponding nucleic acid sequences, cell-free expression systems which carry out protein biosynthesis in vitro. All elements already illustrated above may also be combined to give new methods for producing proteins according to the invention. In this connection, a multiplicity of possible combinations of method steps is conceivable for each protein according to the invention and, as a result, optimal methods must be determined experimentally for each specific individual case.

Further preference is given to those methods in which one, preferably two or more and particularly preferably all codons of the nucleotide sequence have been adapted to the codon usage of the host strain. This is because the transfer of any of said genes to a less related species may be utilized particularly successfully for the synthesis of the protein in question, if their codon usage has been optimized accordingly.

Agents containing an above-described α-amylase variant of the invention constitute a separate subject-matter of the invention.

This means any agent in which the α-amylase in question is applied in any form, i.e. brought into the desired hydrolytic contact with its substrate, starch or starch-like polysaccharide, or is prepared therefor. The desired contact usually takes place in an aqueous environment which is advantageously buffered to an appropriate pH and, where appropriate, contains further beneficial factors. These include, for example, further enzymes which further convert the immediate reaction products, for example with regard to starch liquefaction for the production of food or animal feed or for ethanol production. Also included here are low-molecular weight compounds which are included, for example, in nascent oligosaccharides, such as cyclodextrins, or low-molecular compounds which further solubilize the cleavage products or have a beneficial effect on the overall process, such as, for example, surfactants within the framework of a detergent formulation. They may also be agents in which the desired analytical activity is to be induced only with a large time delay, such as, for example, in temporary bonding processes, according to which the α-amylase variant is added early to the adhesive in question but becomes actually active only after a long time, due to an increase in the water content. This applies, for example, also to detergents and cleansers which are intended to act on the substrate at the moment of dilution in the wash liquor, only after a storage phase.

One embodiment of this subject matter of the invention are those agents which are a detergent or cleanser.

The properties and important ingredients according to the invention of such detergents and cleansers are illustrated in more detail hereinbelow. At this point, there will be first an overview of the most important embodiments, which are therefore particularly preferred according to the invention, of such detergents and cleansers:

A detergent or cleanser according to the invention, comprising from 0.000001 percent by weight to 5% by weight, in particular from 0.00001 to 3% by weight, of the α-amylase variant;

a detergent or cleanser according to the invention, which additionally includes other enzymes, in particular hydrolytic enzymes or oxidoreductases, particularly preferably further amylases, proteases, lipases, cutinases, hemicellulases, cellulases, β-glucanases, oxidases, peroxidases, perhydrolases and/or laccases;

a detergent or cleanser according to the invention, wherein the α-amylase variant is stabilized and/or its contribution to the washing or cleaning performance of the agent is increased by any of the other components of said agent;

a detergent or cleanser according to the invention, which is overall solid, preferably after a compacting step for at least one of the included components, particularly preferably that it is overall compacted;

a detergent or cleanser according to the invention, which is overall liquid, gel-like or paste-like, preferably with encapsulation of at least one of the included components, particularly preferably with encapsulation of at least one of the included enzymes, very particularly preferably with encapsulation of the α-amylase variant.

One important field of use of amylases is that as active components in detergents or cleansers for cleaning textiles or solid surfaces, such as, for example, crockery, floors or utensils. In these applications, the amylolytic activity serves to break down by hydrolysis, or detach from the substrate, carbohydrate-containing contaminations and in particular those based on starch. In this connection, they may be used alone, in suitable media or else in detergents or cleansers. The conditions to be chosen for this, such as, for example, temperature, pH, ionic strength, redox conditions or mechanical effects, should be optimized for the particular cleaning problem, i.e. in relation to the soiling and the substrate. Thus, usual temperatures for detergents and cleansers are in ranges from 10°

C. for manual compositions via 40° C. and 60° C. up to 95° C. for machine compositions or for industrial applications. Since the temperature can usually be adjusted continuously in modern washing and dishwashing machines, all intermediate temperatures are also included. The ingredients of the relevant agents are preferably also matched to one another. The other conditions can likewise be designed very specifically for the particular cleaning purpose via the other components of said agents, illustrated below.

Preferred detergents and cleansers of the invention are distinguished by the washing or cleaning performance of the agent in question being improved by adding an α-amylase variant of the invention, compared with the formulation without this variant, under any of the conditions definable in this way. Preference is given to synergies with respect to cleaning performance.

An α-amylase variant of the invention can be used both in compositions for large-scale consumers or industrial users and in products for the private consumer, and all presentations which are expedient and/or established in the art also represent embodiments of the present invention. The detergents or cleansers of the invention thus mean any conceivable types of cleaning compositions, both concentrates and compositions to be applied in an undiluted form; for use on a commercial scale, in the washing machine or for washing or cleaning by hand. They include, for example, detergents for textiles, carpets or natural fibers, for which agents the term detergent is used according to the present invention. They include also, for example, dishwashing agents for dishwashers or manual washing-up liquids or cleaners for hard surfaces such as metal, glass, porcelain, ceramics, tiles, stone, painted surfaces, plastics, wood or leather; for these, the term cleanser is used according to the present invention. Any type of detergent or cleanser is an embodiment of the present invention, if an amylase of the invention has been added to it.

Embodiments of the present invention comprise any presentations established in the art and/or any expedient presentations of the compositions of the invention. These include, for example, solids, pulverulent, liquid, gel-like or paste-like compositions, where appropriate also composed of two or more phases, compressed or uncompressed; they also include for example: extrudates, granules, tablets or pouches, packaged both in large containers and in portions.

α-Amylases are combined in agents of the invention, for example, with one or more of the following ingredients: nonionic, anionic and/or cationic surfactants, bleaches, bleach activators, bleach catalysts, builders and/or cobuilders, solvents, thickeners, sequestering agents, electrolytes, optical brighteners, antiredeposition agents, corrosion inhibitors, in particular silver protectants, soil release agents, color transfer inhibitors, foam inhibitors, abrasives, dyes, fragrances, antimicrobial agents, UV stabilizers, enzymes such as, for example, proteases, (where appropriate other) amylases, lipases, cellulases, hemicellulases or oxidases, stabilizers, in particular enzyme stabilizers, and other components known in the art.

The nonionic surfactants used are preferably alkoxylated, advantageously ethoxylated, in particular primary alcohols having preferably from 8 to 18 carbon atoms and, on average, from 1 to 12 mol of ethylene oxide (EO) per mole of alcohol, in which the alcohol radical can be linear or, preferably, methyl-branched in the 2-position or can comprise linear and methyl-branched radicals in a mixture as are customarily present in oxo alcohol radicals. Particular preference is, however, given to alcohol ethoxylates containing linear radicals of alcohols of native origin having from 12 to 18 carbon atoms, for example from coconut, palm, tallow fatty or oleyl alcohol, and, on average, from 2 to 8 EO per mole of alcohol. Preferred ethoxylated alcohols include, for example, $C_{12\text{-}14}$-alcohols having 3 EO or 4 EO, $C_{9\text{-}11}$-alcohol having 7 EO, $C_{13\text{-}15}$-alcohols having 3 EO, 5 EO, 7 EO or 8 EO, $C_{12\text{-}18}$-alcohols having 3 EO, 5 EO or 7 EO, and mixtures of these, such as mixtures of $C_{12\text{-}14}$-alcohol having 3 EO and $C_{12\text{-}18}$-alcohol having 5 EO. The degrees of ethoxylation given are statistical averages which may be an integer or a fraction for a specific product. Preferred alcohol ethoxylates have a narrowed homolog distribution (narrow range ethoxylates, NRE). In addition to these nonionic surfactants, fatty alcohols having more than 12 EO can also be used. Examples thereof are tallow fatty alcohol having 14 EO, 25 EO, 30 EO or 40 EO.

A further class of preferably used nonionic surfactants which are used either as the sole nonionic surfactant or in combination with other nonionic surfactants are alkoxylated preferably ethoxylated or ethoxylated and propoxylated fatty acid alkyl esters, preferably having from 1 to 4 carbon atoms in the alkyl chain, in particular fatty acid methyl esters.

The application DE 1020040430.6 which has not been published previously reveals cleansers, in particular machine dishwashing agents, which (a) comprise one or more nonionic surfactants having the following general formula:

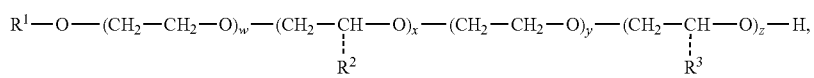

where $R^1$ is a $C_{6\text{-}24}$-alkyl or -alkenyl radical, the groups $R^2$ and $R^3$ are in each case particular hydrocarbon radicals and the indices w, x, y, z are in each case integers up to 6, or a surfactant system of at least one nonionic surfactant F of the general formula:

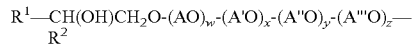

and at least one nonionic surfactant G of the general formula:

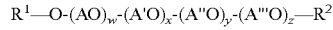

where in each case $R^1$ is a $C_{6\text{-}24}$-alkyl or -alkenyl radical, $R^2$ is a hydrocarbon radical having from 2 to 26 carbon atoms, A, A', A" and A'" are in each case particular hydrocarbon radicals, and w, x, y and z are in each case values of up to 25, said surfactant system having the surfactants F and G in a weight ratio of between 1:4 and 100:1, and a special α-amylase variant as component (b).

These surfactants can be combined, in particular in machine dishwashing agents, also with α-amylases which correspond to the present invention, in particular if they have, besides the substitutions according to the invention, those which can be found in one or more of the applications WO 96/23873 A1, WO 00/60060 A2 and WO 01/66712 A2. This applies in particular to the case in which the commercial product Stainzyme® from Novozymes, which falls under these applications, is improved in further positions and is additionally provided with at least one substitution of the invention, since in principle an additive effect of the various modifications must be assumed.

A further class of nonionic surfactants which can advantageously be used are the alkyl polyglycosides (APG). Alkyl polyglycosides which may be used satisfy the general formula RO(G)$_z$, in which R is a linear or branched, in particular methyl-branched in the 2-position, saturated or unsaturated, aliphatic radical having from 8 to 22, preferably from 12 to 18 carbon atoms, and G is the symbol which stands for a glycose unit having 5 or 6 carbon atoms, preferably for glucose. The degree of glycosylation z is here between 1.0 and 4.0, preferably between 1.0 and 2.0 and in particular between 1.1 and 1.4. Preference is given to using linear alkyl polyglucosides, i.e. alkyl polyglycosides in which the polyglycosyl radical is a glucose radical, and the alkyl radical is an n-alkyl radical.

Nonionic surfactants of the amine oxide type, for example N-cocoalkyl-N,N-dimethylamine oxide and N-tallow alkyl-N,N-dihydroxyethylamine oxide, and of the fatty acid alkanolamides may also be suitable. The proportion of these nonionic surfactants is preferably no more than that of the ethoxylated fatty alcohols, in particular no more than half thereof.

Further suitable surfactants are polyhydroxy fatty acid amides of the formula (II)

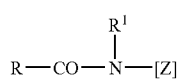
(II)

in which RCO is an aliphatic acyl radical having from 6 to 22 carbon atoms, $R^1$ is hydrogen, an alkyl or hydroxyalkyl radical having from 1 to 4 carbon atoms and [Z] is a linear or branched polyhydroxyalkyl radical having from 3 to 10 carbon atoms and from 3 to 10 hydroxyl groups. The polyhydroxy fatty acid amides are known substances which can usually be obtained by reductive amination of a reducing sugar with ammonia, an alkylamine or an alkanolamine and subsequent acylation with a fatty acid, a fatty acid alkyl ester or a fatty acid chloride.

The group of polyhydroxy fatty acid amides also includes compounds of the formula (III)

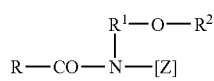
(III)

in which R is a linear or branched alkyl or alkenyl radical having from 7 to 12 carbon atoms, $R^1$ is a linear, branched or cyclic alkyl radical or an aryl radical having from 2 to 8 carbon atoms, and $R^2$ is a linear, branched or cyclic alkyl radical or an aryl radical or an oxy-alkyl radical having from 1 to 8 carbon atoms, where $C_{1-4}$-alkyl or phenyl radicals are preferred, and [Z] is a linear polyhydroxyalkyl radical whose alkyl chain is substituted with at least two hydroxyl groups, or alkoxylated, preferably ethoxylated or propoxylated, derivatives of this radical.

[Z] is preferably obtained by reductive amination of a reducing sugar, for example glucose, fructose, maltose, lactose, galactose, mannose or xylose. The N-alkoxy- or N-aryloxy-substituted compounds may be converted, for example by reaction with fatty acid methyl esters in the presence of an alkoxide as catalyst, into the desired polyhydroxy fatty acid amides.

The anionic surfactants used are, for example, those of the sulfonate and sulfate type. Suitable surfactants of the sulfonate type are preferably $C_{9-13}$-alkylbenzene sulfonates, olefin sulfonates, i.e. mixtures of alkene and hydroxyalkane sulfonates, and disulfonates, as obtained, for example, from $C_{12-18}$-monoolefins having a terminal or internal double bond by sulfonation with gaseous sulfur trioxide and subsequent alkaline or acidic hydrolysis of the sulfonation products. Also suitable are alkane sulfonates which are obtained from $C_{12-18}$-alkanes, for example, by sulfochlorination or sulfoxidation with subsequent hydrolysis or neutralization. Likewise suitable are also the esters of α-sulfo fatty acids (estersulfonates), for example the α-sulfonated methyl esters of hydrogenated coconut, palm kernel or tallow fatty acids.

Further suitable anionic surfactants are sulfated fatty acid glycerol esters. Fatty acid glycerol esters mean the mono-, di- and triesters, and mixtures thereof, as are obtained during the preparation by esterification of a monoglycerol with from 1 to 3 mol of fatty acid or during the transesterification of triglycerides with from 0.3 to 2 mol of glycerol. Preferred sulfated fatty acid glycerol esters are here the sulfation products of saturated fatty acids having from 6 to 22 carbon atoms, for example of caproic acid, caprylic acid, capric acid, myristic acid, lauric acid, palmitic acid, stearic acid or behenic acid.

Preferred alk(en)yl sulfates are the alkali metal, and in particular the sodium, salts of sulfuric half-esters of $C_{12}$-$C_{18}$-fatty alcohols, for example of coconut fatty alcohol, tallow fatty alcohol, lauryl, myristyl, cetyl or stearyl alcohol or of $C_{10}$-$C_{20}$-oxo alcohols and those half-esters of secondary alcohols of these chain lengths. Further preferred are alk(en)yl sulfates of the said chain length which comprise a synthetic, petrochemical-based straight-chain alkyl radical which have analogous degradation behaviour to the equivalent compounds based on fatty chemical raw materials. From a washing performance viewpoint, preference is given to $C_{12}$-$C_{16}$-alkyl sulfates and $C_{12}$-$C_{15}$-alkyl sulfates, and $C_{14}$-$C_{15}$-alkyl sulfates. 2,3-Alkyl sulfates are also suitable anionic surfactants.

The sulfuric monoesters of straight-chain or branched $C_{7-21}$-alcohols ethoxylated with from 1 to 6 mol of ethylene oxide, such as 2-methyl-branched $C_{9-11}$-alcohols having, on average, 3.5 mol of ethylene oxide (EO) or $C_{12-18}$-fatty alcohols having from 1 to 4 EO, are also suitable. Owing to their high foaming behaviour, they are used in cleaning agents only in relatively small amounts, for example in amounts up to 5% by weight, usually from 1 to 5% by weight.

Further suitable anionic surfactants are also the salts of alkylsulfosuccinic acid, which are also referred to as sulfosuccinates or as sulfosuccinic esters and which are monoesters and/or diesters of sulfosuccinic acid with alcohols, preferably fatty alcohols and, in particular, ethoxylated fatty alcohols. Preferred sulfosuccinates contain $C_{8-18}$-fatty alcohol radicals or mixtures thereof. Particularly preferred sulfosuccinates contain a fatty alcohol radical derived from ethoxylated fatty alcohols, which are themselves nonionic surfactants (see below for description). In this connection, sulfosuccinates whose fatty alcohol radicals are derived from ethoxylated fatty alcohols having a narrowed homologue distribution are, in turn, particularly preferred. Likewise, it is also possible to use alk(en)ylsuccinic acid having preferably from 8 to 18 carbon atoms in the alk(en)yl chain or salts thereof.

Further suitable anionic surfactants are, in particular, soaps. Saturated fatty acid soaps such as the salts of lauric acid, myristic acid, palmitic acid, stearic acid, hydrogenated erucic acid and behenic acid, and, in particular, soap mixtures derived from natural fatty acids, for example coconut, palm kernel or tallow fatty acids, are suitable.

The anionic surfactants including soaps may be present in the form of their sodium, potassium or ammonium salts, and as soluble salts of organic bases such as mono-, di- or triethanolamine. The anionic surfactants are preferably in the form of their sodium or potassium salts, in particular in the form of the sodium salts.

The surfactants may be present in the cleaning agents or washing agents according to the invention in an overall amount of from preferably 5% by weight to 50% by weight, in particular from 8% by weight to 30% by weight, based on the finished agent.

Agents according to the invention may contain bleaches. Of the compounds which serve as bleaches and produce $H_2O_2$ in water, sodium percarbonate, sodium perborate tetrahydrate and sodium perborate monohydrate are of particular importance. Other bleaches which can be used are, for example, peroxopyrophosphates, citrate perhydrates and $H_2O_2$-producing peracidic salts or peracids, such as persulfates or persulfuric acid. Also useful is the urea peroxohydrate percarbamide which can be described by the formula $H_2N-CO-NH_2.H_2O_2$. In particular when used for cleaning hard surfaces, for example for machine dishwashing, the agents, if desired, may also contain bleaches from the group of organic bleaches, although the use thereof is possible in principle also in agents for washing textiles. Typical organic bleaches are diacyl peroxides such as, for example, dibenzoyl peroxide. Further typical organic bleaches are the peroxy acids, specific examples being alkyl peroxy acids and aryl peroxy acids. Preferred representatives are peroxy benzoic acid and its ring-substituted derivatives, such as alkylperoxybenzoic acids, but also peroxy-α-naphthoic acid and magnesium monoperphthalate, the aliphatic or substituted aliphatic peroxy acids such as peroxylauric acid, peroxystearic acid, ∈-phthalimidoperoxycaproic acid (phthalimidoperoxyhexanoic acid, PAP), o-carboxybenzamidoperoxycaproic acid, N-nonenylamidoperadipic acid and N-nonenylamidopersuccinate, and aliphatic and araliphatic peroxydicarboxylic acids such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid) may be used.

The bleach content of the agents may be from 1 to 40% by weight and, in particular, from 10 to 20% by weight, using advantageously perborate monohydrate or percarbonate. The applications WO 99/63036 and WO 99/63037, respectively, disclose a synergistic use of amylase with percarbonate and of amylase with percarboxylic acid.

In order to achieve improved bleaching action in cases of washing at temperatures of 60° C. and below, and in particular in the case of laundry pretreatment, the agents may also include bleach activators. Bleach activators which can be used are compounds which, under perhydrolysis conditions, give aliphatic peroxocarboxylic acids having preferably from 1 to 10 carbon atoms, in particular from 2 to 4 carbon atoms, and/or substituted or unsubstituted perbenzoic acid. Substances which carry O- and/or N-acyl groups of the said number of carbon atoms and/or substituted or unsubstituted benzoyl groups are suitable. Preference is given to plurally acylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular 1,3,4,6-tetraacetylglycolurile (TAGU), N-acylimides, in particular N-nonanoylsuccinimide (NOSI), acylated phenol sulfonates, in particular n-nonanoyl- or isononanoyloxybenzene sulfonate (n- or iso-NOBS), acylated hydroxycarboxylic acids such as triethyl-O-acetyl citrate (TEOC), carboxylic anhydrides, in particular phthalic anhydride, isatoic anhydride and/or succinic anhydride, carboxamides such as N-methyldiacetamide, gly-colide, acylated polyhydric alcohols, in particular triacetin, ethylene glycol diacetate, isopropenyl acetate, 2,5-diacetoxy-2,5-dihydrofuran and the enol esters disclosed in German patent applications DE 196 16 693 and DE 196 16 767, and acetylated sorbitol and mannitol, or mixtures thereof described in European patent application EP 0 525 239 (SORMAN), acylated sugar derivatives, in particular pentaacetylglucose (PAG), pentaacetylfructose, tetraacetylxylose and octaacetyllactose, and acetylated, optionally N-alkylated glucamine or gluconolactone, triazole or triazole derivatives and/or particulate caprolactams and/or caprolactam derivatives, preferably N-acylated lactams, for example N-benzoylcaprolactam and N-acetylcaprolactam. Hydrophilically substituted acyl acetals and acyl lactams are likewise used with preference. It is also possible to use combinations of conventional bleach activators. Nitrile derivatives such as cyanopyridines, nitrile quats, e.g. N-alkylammoniumacetonitriles, and/or cyanamide derivatives may also be used. Preferred bleach activators are sodium 4-(octanoyloxy)benzenesulfonate, n-nonanoyl- or isononanoyloxybenzenesulfonate (n- or iso-NOBS), undecenoyloxybenzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12), and N-methylmorpholinium acetonitrile (MMA). Such bleach activators may be present in the customary quantitative range from 0.01 to 20% by weight, preferably in amounts from 0.1 to 15% by weight, in particular 1% by weight to 10% by weight, based on the total composition.

In addition to the conventional bleach activators or instead of them, it is also possible for "bleach catalysts" to be present. These substances are bleach-enhancing transition metal salts or transition metal complexes such as, for example, Mn, Fe, Co, Ru or Mo saline complexes or carbonyl complexes. Mn, Fe, Co, Ru, Mo, Ti, V and Cu complexes containing N-containing tripod ligands, and Co, Fe, Cu and Ru amine complexes are also suitable as bleach catalysts. Acetonitrile derivatives, according to WO 99/63038, and bleach-activating transition metal complex compounds, according to WO 99/63041 are capable of developing a bleach-activating action in combination with amylases.

Agents according to the invention usually contain one or more builders, in particular zeolites, silicates, carbonates, organic cobuilders and, where no ecological reasons oppose their use, also phosphates. The latter are the preferred builders for use in particular in cleaning agents for machine dishwashing.

Compounds which may be mentioned here are crystalline, layered sodium silicates of the general formula $NaMSi_xO_{2x+1}.yH_2O$, where M is sodium or hydrogen, x is a number from 1.6 to 4, preferably from 1.9 to 4.0, and y is a number from 0 to 20, and preferred values for x are 2, 3 or 4. Preferred crystalline phyllosilicates of the formula indicated are those where M is sodium and x adopts the values 2 or 3. In particular, both β- and δ-sodium disilicates $Na_2Si_2O_5.yH_2O$ are preferred. Compounds of this kind are sold, for example, under the name SKS® (Clariant). Thus, SKS-6® is primarily a δ-sodium disilicate having the formula $Na_2Si_2O_5.yH_2O$, and SKS-7® is primarily the β-sodium disilicate. Reacting the δ-sodium disilicate with acids (for example citric acid or carbonic acid) gives kanemite $NaHSi_2O_5.yH_2O$, sold under the names SKS-9® and, respectively, SKS-10® (Clariant). It may also be advantageous to use chemical modifications of the said phyllosilicates. The alkalinity of the phyllosilicates, for example, can thus be suitably influenced. Phyllosilicates doped with phosphate or with carbonate have, compared to the δ-sodium disilicate, altered crystal morphologies, dissolve more rapidly and display an increased calcium binding ability, compared to δ-sodium disilicate. Phyllosilicates of the general empirical formula $xNa_2O.ySiO_2.zP_2O_5$ where the x-to-y ratio corresponds to a number from 0.35 to 0.6, the x-to-z ratio to a number from 1.75 to 1200 and the y-to-z ratio to a number from 4 to 2800 are to be mentioned in particular. The solubility of the phyllosilicates may also be increased by using particularly finely granulated phyllosilicates. It is also possible to use compounds of the crystalline phyllosilicates with other ingredients. Compounds which may be mentioned here are in particular those with cellulose derivatives which have advantageous disintegrating action and are used in particular in washing agent tablets, and those with polycarboxylates, for example citric acid, or polymeric polycarboxylates, for example copolymers of acrylic acid.

It is also possible to use amorphous sodium silicates having an $Na_2O:SiO_2$ modulus of from 1:2 to 1:3.3, preferably from 1:2 to 1:2.8, and in particular from 1:2 to 1:2.6, which have delayed dissolution and secondary washing properties. The dissolution delay relative to conventional amorphous sodium silicates can have been induced by various means, for example by surface treatment, compounding, compaction/compression or by overdrying. Within the scope of this invention, the term "amorphous" also means "X-ray amorphous". This means that in X-ray diffraction experiments the silicates do not give the sharp X-ray refractions typical of crystalline substances, but instead, at best, one or more maxima of these scattered X-rays, which have a width of several degree units of the diffraction angle. However, particularly good builder properties will very likely result if, in electron diffraction experiments, the silicate particles give poorly defined or even sharp diffraction maxima. This is to be interpreted to the effect that the products have microcrystalline regions with a size from 10 to a few hundred nm, preference being given to values up to at most 50 nm and in particular up to at most 20 nm. Particular preference is given to compressed/compacted amorphous silicates, compounded amorphous silicates and overdried X-ray amorphous silicates.

A finely crystalline, synthetic zeolite containing bonded water, which may be used where appropriate, is preferably zeolite A and/or P. As zeolite P, zeolite MAP® (commercial product from Crosfield) is particularly preferred. However, zeolite X and mixtures of A, X and/or P are also suitable. A product which is commercially available and can be used with preference within the scope of the present invention is, for example, also a co-crystallizate of zeolite X and zeolite A (approx. 80% by weight zeolite X), which is sold by CONDEA Augusta S.p.A. under the trade name VEGOBOND AX® and can be described by the formula

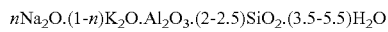

$nNa_2O.(1-n)K_2O.Al_2O_3.(2-2.5)SiO_2.(3.5-5.5)H_2O$

Suitable zeolites have an average particle size of less than 10 μm (volume distribution; measurement method: Coulter counter) and preferably contain from 18 to 22% by weight, in particular from 20 to 22% by weight, of bonded water.

Use of the generally known phosphates as builder substances is of course also possible, provided such a use should not be avoided for ecological reasons. Among the multiplicity of commercially available phosphates, the alkali metal phosphates are the most important in the washing and cleaning agents industry, with pentasodium or pentapotassium triphosphate (sodium or potassium tripolyphosphate) being particularly preferred.

In this connection, alkali metal phosphates is the collective term for the alkali metal (in particular sodium and potassium) salts of the various phosphoric acids, it being possible to differentiate between metaphosphoric acids $(HPO_3)_n$ and orthophosphoric acid $H_3PO_4$ as well as higher molecular weight representatives. The phosphates combine several advantages: they act as alkali carriers, prevent lime deposits on machine parts and lime incrustations in fabrics and, moreover, contribute to the cleaning performance.

Sodium dihydrogenphosphate, $NaH_2PO_4$, exists as dihydrate (density 1.91 $gcm^{-3}$, melting point 60° C.) and as monohydrate (density 2.04 $gcm^{-3}$). Both salts are white powders which are very readily soluble in water and which lose their water of crystallization upon heating and at 200° C. convert to the weakly acidic diphosphate (disodium hydrogendiphosphate, $Na_2H_2P_2O_7$), at a higher temperature to sodium trimetaphosphate ($Na_3P_3O_9$) and Maddrell's salt (see below). $NaH_2PO_4$ is acidic; it forms when phosphoric acid is adjusted to a pH of 4.5 using sodium hydroxide solution and the suspension is sprayed. Potassium dihydrogenphosphate (primary or monobasic potassium phosphate, potassium biphosphate, KDP), $KH_2PO_4$, is a white salt of density 2.33 $gcm^{-3}$, has a melting point of 253° [decomposition with the formation of potassium polyphosphate $(KPO_3)_x$] and is readily soluble in water.

Disodium hydrogenphosphate (secondary sodium phosphate), $Na_2HPO_4$, is a colorless crystalline salt which is very readily soluble in water. It exists in anhydrous form and with 2 mol (density 2.066 $gcm^{-3}$, loss of water at 95° C.), 7 mol (density 1.68 $gcm^{-3}$, melting point 48° C. with loss of $5H_2O$) and 12 mol (density 1.52 $gcm^{-3}$, melting point 35° C. with loss of $5H_2O$) of water, becomes anhydrous at 100° C. and upon more vigorous heating converts to the diphosphate $Na_4P_2O_7$. Disodium hydrogenphosphate is prepared by neutralizing phosphoric acid with soda solution using phenolphthalein as indicator. Dipotassium hydrogenphosphate (secondary or dibasic potassium phosphate), $K_2HPO_4$, is an amorphous, white salt which is readily soluble in water.

Trisodium phosphate, tertiary sodium phosphate, $Na_3PO_4$, are colorless crystals which, in the form of the dodecahydrate, have a density of 1.62 $gcm^{-3}$ and a melting point of 73-76° C. (decomposition), in the form of the decahydrate (corresponding to 19-20% $P_2O_5$) have a melting point of 100° C. and in anhydrous form (corresponding to 39-40% $P_2O_5$) have a density of 2.536 $gcm^{-3}$. Trisodium phosphate is readily soluble in water with an alkaline reaction and is prepared by evaporating a solution of exactly 1 mol of disodium phosphate and 1 mol of NaOH. Tripotassium phosphate (tertiary or tribasic potassium phosphate), $K_3PO_4$, is a white, deliquescent granular powder of density 2.56 $gcm^{-3}$, has a melting point of 1340° C. and is readily soluble in water with an alkaline reaction. It is produced, for example, during the heating of Thomas slag with carbon and potassium sulfate. Despite the higher price, the more readily soluble, and therefore highly effective, potassium phosphates are often preferred over corresponding sodium compounds in the cleaning agents industry.

Tetrasodium diphosphate (sodium pyrophosphate), $Na_4P_2O_7$, exists in anhydrous form (density 2.534 $gcm^{-3}$, melting point 988° C., also 880° C. given) and as decahydrate (density 1.815-1.836 $gcm^{-3}$, melting point 94° C. with loss of water). Both substances are colorless crystals which dissolve in water with an alkaline reaction. $Na_4P_2O_7$ is formed during the heating of disodium phosphate to >200° C. or by reacting phosphoric acid with soda in a stoichiometric ratio and dewatering the solution by spraying. The decahydrate complexes heavy metal salts and hardness constituents and thus reduces the water hardness. Potassium diphosphate (potassium pyrophosphate), $K_4P_2O_7$, exists in the form of the trihydrate and is a colorless, hygroscopic powder of density 2.33 $gcm^{-3}$, which is soluble in water, the pH of the 1% strength solution at 25° C. being 10.4.

Condensation of $NaH_2PO_4$ and $KH_2PO_4$ results in higher molecular weight sodium phosphates and potassium phosphates, respectively, amongst which cyclic representatives, the sodium and potassium metaphosphates, respectively, and chain-shaped types, the sodium and potassium polyphosphates, respectively, can be differentiated. Particularly for the latter, a multiplicity of names are in use: melt or thermal phosphates, Graham's salt, Kurrol's and Maddrell's salt. All higher sodium and potassium phosphates are together referred to as condensed phosphates.

The industrially important pentasodium triphosphate, $Na_5P_3O_{10}$ (sodium tripolyphosphate), is a nonhygroscopic, white, water-soluble salt which is anhydrous or crystallizes with $6H_2O$ and is of the general formula NaO—[P(O)(ONa)—O]$_n$—Na where n=3. In 100 g of water, about 17 g of the salt which is free of water of crystallization dissolve at room temperature, approx. 20 g dissolve at 60° C., and about 32 g dissolve at 10° C.; if the solution is heated at 100° C. for two hours, about 8% of orthophosphate and 15% of diphosphate form due to hydrolysis. In the preparation of pentasodium triphosphate, phosphoric acid is reacted with soda solution or sodium hydroxide solution in a stoichiometric ratio, and the solution is dewatered by spraying. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is available commercially, for example, in the form of a 50% strength by weight solution (>23% $P_2O_5$, 25% $K_2O$). The potassium polyphosphates are used widely in the washing and cleaning agents industry. In addition, sodium potassium tripolyphosphates also exist which can likewise be used within the scope of the present invention. These form, for example, when sodium trimetaphosphate is hydrolysed with KOH:

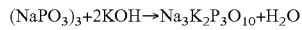
$(NaPO_3)_3 + 2KOH \rightarrow Na_3K_2P_3O_{10} + H_2O$

According to the invention, these can be used exactly as sodium tripolyphosphate, potassium tripolyphosphate or mixtures of these two; mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate can also be used according to the invention.

Organic cobuilders which can be used in the washing and cleaning agents according to the invention are, in particular, polycarboxylates or polycarboxylic acids, polymeric polycarboxylates, polyaspartic acid, polyacetals, optionally oxidized dextrins, further organic cobuilders (see below), and phosphonates. These classes of substance are described below.

Usable organic builder substances are, for example, the polycarboxylic acids usable in the form of their sodium salts, the term polycarboxylic acids meaning those carboxylic acids which carry more than one acid function. Examples of these are citric acid, adipic acid, succinic acid, glutaric acid, malic acid, tartaric acid, maleic acid, fumaric acid, sugar acids, aminocarboxylic acids, nitrilotriacetic acid (NTA), as long as such a use should not be avoided for ecological reasons, and mixtures thereof. Preferred salts are the salts of the polycarboxylic acids such as citric acid, adipic acid, succinic acid, glutaric acid, tartaric acid, sugar acids, and mixtures thereof.

It is also possible to use the acids per se. In addition to their builder action, the acids typically also have the property of an acidifying component and thus also serve to establish a lower and milder pH of washing or cleaning agents, as long as the pH resulting from the mixture of the remaining components is not desired. Particular mention should be made here of system-compatible and environmentally safe acids such as citric acid, acetic acid, tartaric acid, malic acid, lactic acid, glycolic acid, succinic acid, glutaric acid, adipic acid, gluconic acid and any mixtures thereof. However, mineral acids, in particular sulfuric acid, or bases, in particular ammonium or alkali metal hydroxides, may also serve as pH regulators. The agents according to the invention contain such regulators in amounts of preferably not more than 20% by weight, in particular from 1.2% by weight to 17% by weight.

Suitable builders are also polymeric polycarboxylates; these are, for example, the alkali metal salts of polyacrylic acid or of polymethacrylic acid, for example those having a relative molecular mass of from 500 to 70 000 g/mol.

The molar masses given for polymeric polycarboxylates are, for the purposes of this specification, weight-average molar masses, $M_w$, of the respective acid form, determined in principle by means of gel permeation chromatography (GPC), using a UV detector. The measurement was made against an external polyacrylic acid standard which, owing to its structural similarity towards the polymers studied, provides realistic molecular weight values. These figures differ considerably from the molecular weight values obtained using polystyrenesulfonic acids as the standard. The molar masses measured against polystyrenesulfonic acids are usually considerably higher than the molar masses given in this specification.

Suitable polymers are, in particular, polyacrylates which preferably have a molecular mass of from 2000 to 20 000 g/mol. Owing to their superior solubility, preference in this group may be given in turn to the short-chain polyacrylates which have molar masses of from 2000 to 10 000 g/mol, and particularly preferably from 3000 to 5000 g/mol.

Also suitable are copolymeric polycarboxylates, in particular those of acrylic acid with methacrylic acid and of acrylic acid or methacrylic acid with maleic acid. Copolymers which have proven to be particularly suitable are those of acrylic acid with maleic acid which contain from 50 to 90% by weight of acrylic acid and from 50 to 10% by weight of maleic acid. Their relative molecular mass, based on free acids, is generally from 2000 to 70 000 g/mol, preferably 20 000 to 50 000 g/mol and in particular 30 000 to 40 000 g/mol. The (co)polymeric polycarboxylates may be used either as powders or as aqueous solution. The (co)polymeric polycarboxylates may be from 0.5 to 20% by weight, in particular 1 to 10% by weight of the content of the agent.

To improve the solubility in water, the polymers may also contain allylsulfonic acids such as, for example, allyloxybenzenesulfonic acid and methallylsulfonic acid as monomers.

Particular preference is also given to biodegradable polymers of more than two different monomer units, for example those which contain, as monomers, salts of acrylic acid and of maleic acid, and vinyl alcohol or vinyl alcohol derivatives, or those which contain, as monomers, salts of acrylic acid and of 2-alkylallylsulfonic acid, and sugar derivatives.

Further preferred copolymers are those which preferably have, as monomers, acrolein and acrylic acid/acrylic acid salts or acrolein and vinyl acetate.

Further preferred builder substances which may be mentioned are also polymeric aminodicarboxylic acids, their salts or their precursor substances. Particular preference is given to polyaspartic acids or salts and derivatives thereof.

Further suitable builder substances are polyacetals which can be obtained by reacting dialdehydes with polyolcarboxylic acids having from 5 to 7 carbon atoms and at least 3 hydroxyl groups. Preferred polyacetals are obtained from dialdehydes such as glyoxal, glutaraldehyde, terephthalaldehyde and mixtures thereof and from polyolcarboxylic acids such as gluconic acid and/or glucoheptonic acid.

Further suitable organic builder substances are dextrins, for example oligomers or polymers of carbohydrates, which can be obtained by partial hydrolysis of starches. The hydrolysis can be carried out by customary processes, for example acid-catalyzed or enzyme-catalyzed processes. The hydrolysis products preferably have average molar masses in the range from 400 to 500 000 g/mol. Preference is given here to a polysaccharide having a dextrose equivalent (DE) in the range from 0.5 to 40, in particular from 2 to 30, where DE is a common measure of the reducing action of a polysaccharide compared with dextrose which has a DE of 100. It is possible to use both maltodextrins having a DE between 3 and 20 and dried glucose syrups having a DE between 20 and 37, and also "yellow dextrins" and "white dextrins" with higher molar masses in the range from 2000 to 30 000 g/mol.

The oxidized derivatives of such dextrins are their reaction products with oxidation agents which are able to oxidize at least one alcohol function of the saccharide ring to the carboxylic acid function. Particularly preferred organic builders for agents according to the invention are oxidized starches and derivatives thereof.

Oxydisuccinates and other derivatives of disuccinates, preferably ethylenediamine disuccinate, are also further suitable cobuilders. Here, ethylenediamine N,N'-disuccinate (EDDS) is preferably used in the form of its sodium or magnesium salts. In this connection, further preference is also given to glycerol disuccinates and glycerol trisuccinates. Suitable use amounts in zeolite-containing and/or silicate-containing formulations are between 3 and 15% by weight.

Further organic cobuilders which may be used are, for example, acetylated hydroxycarboxylic acids or salts thereof, which may also be present, where appropriate, in lactone form and which contain at least 4 carbon atoms and at least one hydroxy group and at most two acid groups.

A further class of substance having cobuilder properties is the phosphonates. These are, in particular, hydroxyalkane and aminoalkane phosphonates. Among the hydroxyalkane phosphonates, 1-hydroxyethane 1,1-diphosphonate (HEDP) is of particular importance as a cobuilder. It is preferably used as sodium salt, the disodium salt being neutral and the tetrasodium salt being alkaline (pH 9). Suitable aminoalkane phosphonates are preferably ethylenediaminetetramethylene phosphonate (EDTMP), diethylenetriaminepentamethylene phosphonate (DTPMP) and higher homologues thereof. They are preferably used in the form of the neutral sodium salts, for example as the hexasodium salt of EDTMP or as the hepta- and octasodium salt of DTPMP. Here, preference is given to using HEDP as builder from the class of phosphonates. In addition, the aminoalkane phosphonates have a marked heavy metal-binding capacity. Accordingly, particularly if the agents also contain bleaches, it may be preferable to use aminoalkane phosphonates, in particular DTPMP, or mixtures of the said phosphonates.

In addition, all compounds which are able to form complexes with alkaline earth metal ions can be used as cobuilders.

The agents according to the invention may contain builder substances, where appropriate, in amounts of up to 90% by weight, and preferably contain them in amounts of up to 75% by weight. Washing agents according to the invention have builder contents of, in particular, from 5% by weight to 50% by weight. In inventive agents for cleaning hard surfaces, in particular for machine cleaning of dishes, the builder substance content is in particular from 5% by weight to 88% by weight, with preferably no water-insoluble builder materials being used in such agents. A preferred embodiment of inventive agents for, in particular, machine cleaning of dishes contains from 20% by weight to 40% by weight water-soluble organic builders, in particular alkali metal citrate, from 5% by weight to 15% by weight alkali metal carbonate and from 20% by weight to 40% by weight alkali metal disilicate.

Solvents which may be used in the liquid to gelatinous compositions of washing and cleaning agents are, for example, from the group of monohydric or polyhydric alcohols, alkanolamines or glycol ethers, as long as they are miscible with water in the given concentration range. Preferably, the solvents are selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether, and mixtures of these solvents.

Solvents may be used in the liquid to gelatinous washing and cleaning agents according to the invention in amounts of between 0.1 and 20% by weight, but preferably below 15% by weight, and in particular below 10% by weight.

To adjust the viscosity, one or more thickeners or thickening systems may be added to compositions according to the invention. These high molecular weight substances which are also called swell(ing) agents usually soak up the liquids and swell in the process, converting ultimately into viscous true or colloidal solutions.

Suitable thickeners are inorganic or polymeric organic compounds. Inorganic thickeners include, for example, polysilicic acids, clay minerals, such as montmorillonites, zeolites, silicas and bentonites. The organic thickeners are from the groups of natural polymers, modified natural polymers and completely synthetic polymers. Such natural polymers are, for example, agar-agar, carrageen, tragacanth, gum arabic, alginates, pectins, polyoses, guar flour, carob seed flour, starch, dextrins, gelatins and casein. Modified natural substances which are used as thickeners are primarily from the group of modified starches and celluloses. Examples which may be mentioned here are carboxymethylcellulose and other cellulose ethers, hydroxyethylcellulose and hydroxypropylcellulose, and carob flour ether. Completely synthetic thickeners are polymers such as polyacrylic and polymethacrylic compounds, vinyl polymers, polycarboxylic acids, polyethers, polyimines, polyamides and polyurethanes.

The thickeners may be present in an amount up to 5% by weight, preferably from 0.05 to 2% by weight, and particularly preferably from 0.1 to 1.5% by weight, based on the finished composition.

The washing and cleaning agent according to the invention may, where appropriate, comprise, as further customary ingredients, sequestering agents, electrolytes and further excipients.

The textile washing agents according to the invention may contain, as optical brighteners, derivatives of diaminostilbenedisulfonic acid or alkali metal salts thereof. Suitable are, for example, salts of 4,4'-bis(2-anilino-4-morpholino-1,3,5-triazinyl-6-amino)stilbene-2,2'-disulfonic acid or similarly constructed compounds which carry a diethanolamino group, a methylamino group, an anilino group or a 2-methoxyethylamino group instead of the morpholino group. In addition, brighteners of the substituted diphenylstyryl type may be present, for example the alkali metal salts of 4,4'-bis(2-sulfostyryl)diphenyl, 4,4'-bis(4-chloro-3-sulfostyryl)diphenyl, or 4-(4-chlorostyryl)-4'-(2-sulfostyryl)diphenyl. Mixtures of the abovementioned optical brighteners may also be used.

Graying inhibitors have the function of keeping the soil detached from the textile fibre in suspension in the liquor. Suitable for this purpose are water-soluble colloids, usually organic in nature, for example starch, glue, gelatin, salts of ethercarboxylic acids or ethersulfonic acids of starch or of cellulose, or salts of acidic sulfuric esters of cellulose or of starch. Water-soluble polyamides containing acidic groups are also suitable for this purpose. Furthermore, starch derivatives other than those mentioned above may be used, for example aldehyde starches. Preference is given to using cellulose ethers such as carboxymethylcellulose (Na salt), methylcellulose, hydroxyalkylcellulose and mixed ethers such as methylhydroxyethylcellulose, methylhydroxypropylcellulose, methylcarboxymethylcellulose, and mixtures thereof, for example in amounts of from 0.1 to 5% by weight, based on the agents.

In order to protect against silver corrosion, silver corrosion inhibitors may be used in dishwashing cleaning agents according to the invention. Such inhibitors are known in the prior art, for example benzotriazoles, iron(III) chloride or $CoSO_4$. As disclosed, silver corrosion inhibitors which are particularly suitable for being used together with enzymes are manganese, titanium, zirconium, hafnium, vanadium, cobalt, or cerium salts and/or complexes in which the specified metals are present in any of the oxidation stages II, III, IV, V or VI. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

Soil-release active ingredients or soil repellents are usually polymers which, when used in a washing agent, impart soil-repellent properties to the laundry fiber and/or assist the ability of the other washing agent ingredients to detach soil. A comparable effect can also be observed with their use in cleaning agents for hard surfaces.

Soil-release active ingredients which are particularly effective and have been known for a long time are copolyesters having dicarboxylic acid, alkylene glycol and polyalkylene glycol units. Examples thereof are copolymers or mixed polymers of polyethylene terephthalate and polyoxyethylene glycol and acidic agents containing, inter alia, a copolymer of a dibasic carboxylic acid and an alkylene or cycloalkylene polyglycol. Polymers of ethylene terephthalate and polyethylene oxide terephthalate and also copolyesters of ethylene glycol, polyethylene glycol, aromatic dicarboxylic acid and sulfonated aromatic dicarboxylic acid in particular molar ratios may also be used advantageously. Also known are methyl or ethyl group end-group-capped polyesters having ethylene and/or propylene terephthalate and polyethylene oxide terephthalate units, and washing agents containing such a soil-release polymer, and also polyesters which contain, in addition to oxyethylene groups and terephthalic acid units, also substituted ethylene units and glycerol units. Also known are polyesters which contain, in addition to oxyethylene groups and terephthalic acid units, 1,2-propylene, 1,2-butylene and/or 3-methoxy-1,2-propylene groups, and glycerol units and which are end-group-capped with $C_1$- to $C_4$-alkyl groups, and also polyesters having polypropylene terephthalate and polyoxyethylene terephthalate units, which are at least partially end-group-capped by $C_{1-4}$-alkyl or acyl radicals. Also known are sulfoethyl end-group-capped terephthalate-containing soil-release polyesters, and soil-release polyesters having terephthalate, alkylene glycol and poly-$C_{2-4}$-glycol units, produced by sulfonation of unsaturated end groups. Other substances which have been disclosed are acidic, aromatic polyesters capable of detaching soil, and nonpolymeric soil-repellent active ingredients for materials made of cotton, which have a plurality of functional units: a first unit which may be cationic, for example, is able to adsorb to the cotton surface by means of electrostatic interaction, and a second unit which is hydrophobic is responsible for the active ingredient remaining at the water/cotton interface.

The color transfer inhibitors suitable for use in textile washing agents according to the invention include, in particular, polyvinylpyrrolidones, polyvinylimidazoles, polymeric N-oxides such as poly(vinylpyridine N-oxide) and copolymers of vinylpyrrolidone with vinylimidazole.

For use in machine cleaning processes, it may be of advantage to add foam inhibitors to the agents. Examples of suitable foam inhibitors are soaps of natural or synthetic origin having a high proportion of $C_{18}$-$C_{24}$ fatty acids. Examples of suitable nonsurfactant-type foam inhibitors are organopolysiloxanes and their mixtures with microfine, optionally silanized silica and also paraffins, waxes, microcrystalline waxes, and mixtures thereof with silanized silica or bis-stearyl-ethylenediamide. With advantages, use is also made of mixtures of different foam inhibitors, for example mixtures of silicones, paraffins or waxes. The foam inhibitors, in particular those containing silicone and/or paraffin, are preferably bound to a granular, water-soluble or dispersible support substance. Particular preference is given here to mixtures of paraffins and bis-stearylethylenediamides.

The application DE 102004020430.6 which has not been published previously reveals cleansers, in particular machine dishwashing agents, which contain a copolymer of (i) unsaturated carboxylic acids, (ii) monomers containing sulfonic acid groups and (iii) optionally further ionic or nonionogenic monomers and a special α-amylase variant. Said copolymers can also be combined with α-amylases according to the invention, in particular if the latter, in addition to the substitutions according to the invention, have substitutions of the kind that can be found in one or more of the applications WO 96/23873 A1, WO 00/60060 A2 and WO 01/66712 A2. This applies in particular if the commercial product Stainzyme® from Novozymes, which falls under these applications, is improved in further positions and is additionally provided with at least one substitution of the invention. This is because an additive effect of the various modifications must be assumed in principle.

A cleaning agent according to the invention for hard surfaces may, in addition, contain ingredients with abrasive action, in particular from the group comprising quartz flours, wood flours, polymer flours, chalks and glass microbeads, and mixtures thereof. Abrasives are present in the cleaning agents according to the invention preferably at not more than 20% by weight, in particular from 5% by weight to 15% by weight.

Dyes and fragrances are added to washing and cleaning agents in order to improve the aesthetic appeal of the products and to provide the consumer, in addition to washing and cleaning performance, with a visually and sensorially "typical and unmistakable" product. As perfume oils and/or fragrances it is possible to use individual odorant compounds, for example the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenyl glycinate, allylcyclohexyl propionate, styrallyl propionate and benzyl salicylate. The ethers include, for example, benzyl ethyl ether; the aldehydes include, for example, the linear alkanals having 8-18 carbon atoms, citral, citronellal, citronellyloxyacetaldehyde, cyclamenaldehyde, hydroxycitronellal, lilial and bourgeonal; the ketones include, for example, the ionones, α-isomethylionone and methyl cedryl ketone; the alcohols include anethol, citronellol, eugenol, geraniol, linalool, phenylethyl alcohol, and terpineol; the hydrocarbons include primarily the terpenes such as limonene and pinene. Preference, however, is given to the use of mixtures of different odorants which together produce an appealing fragrance note. Such perfume oils may also contain natural odorant mixtures, as obtainable from plant sources, for example pine oil, citrus oil, jasmine oil, patchouli oil, rose oil or ylang-ylang oil. Likewise suitable are muscatel, sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orangepeel oil and sandalwood oil. The dye content of washing and cleaning agents is usually less than 0.01% by weight, while fragrances may make up up to 2% by weight of the overall formulation.

The fragrances may be incorporated directly into the washing and cleaning agents; however, it may also be advantageous to apply the fragrances to carriers which intensify the adhesion of the perfume to the material to be cleaned and, by means of slower fragrance release, ensure long-lasting fragrance, in particular of treated textiles. Materials which have become established as such carriers are, for example, cyclodextrins, it being possible, in addition, for the cyclodextrin-perfume complexes to be additionally coated with further auxiliaries. Another preferred carrier for fragances is the described zeolite X which can also absorb fragrances instead of or in a mixture with surfactants. Preference is therefore given to washing and cleaning agents which contain the described zeolite X and fragrances which, preferably, are at least partially absorbed on the zeolite.

Preferred dyes whose selection is by no means difficult for the skilled worker have high storage stability and insensitivity to the other ingredients of the agents and to light, and also have no pronounced affinity for textile fibres, so as not to stain them.

To control microorganisms, washing or cleaning agents may contain antimicrobial active ingredients. Depending on antimicrobial spectrum and mechanism of action, a distinction is made here between bacteriostatics and bactericides, fungistatics and fungicides, etc. Examples of important substances from these groups are benzalkonium chlorides, alkylaryl sulfonates, halogen phenols and phenol mercury acetate. The terms antimicrobial action and antimicrobial active ingredient have, within the teaching according to the invention, the meaning common in the art. Suitable antimicrobial active ingredients are preferably selected from the groups of alcohols, amines, aldehydes, antimicrobial acids or their salts, carboxylic esters, acid amides, phenols, phenol derivatives, diphenyls, diphenylalkanes, urea derivatives, oxygen acetals, nitrogen acetals and also oxygen and nitrogen formals, benzamidines, isothiazolines, phthalimide derivatives, pyridine derivatives, antimicrobial surfactant compounds, guanidines, antimicrobial amphoteric compounds, quinolines, 1,2-dibromo-2,4-dicyanobutane, iodo-2-propylbutyl carbamate, iodine, iodophors, peroxo compounds, halogen compounds, and any mixtures of the above.

The antimicrobial active ingredient may be selected from ethanol, n-propanol, isopropanol, 1,3-butanediol, phenoxyethanol, 1,2-propylene glycol, glycerol, undecylenic acid, benzoic acid, salicylic acid, dihydracetic acid, o-phenylphenol, N-methylmorpholinoacetonitrile (MMA), 2-benzyl-4-chlorophenol, 2,2'-methylenebis(6-bromo-4-chlorophenol), 4,4'-dichloro-2'-hydroxydiphenyl ether (dichlosan), 2,4,4'-trichloro-2'-hydroxydiphenyl ether (trichlosan), chlorohexidine, N-(4-chlorophenyl)-N-(3,4-dichlorophenyl)urea, N,N'-(1,10-decanediyldi-1-pyridinyl-4-ylidene)-bis(1-octanamine)dihydrochloride, N,N'-bis(4-chlorophenyl)-3,12-diimino-2,4,11,13-tetra-azatetradecanediimidamide, glucoprotamines, antimicrobial surface-active quaternary compounds, guanidines including the bi- and polyguanidines, such as, for example, 1,6-bis(2-ethylhexyl-biguamidohexane)dihydrochloride, 1,6-di-($N_1$,$N_1$'-phenyl-diguanido-$N_5$,$N_5$')hexane tetrahydrochloride, 1,6-di-($N_1$, $N_1$'-phenyl-$N_1$,$N_1$-methyldiguanido-$N_5$,$N_5$')hexane dihydrochloride, 1,6-di-($N_1$,$N_1$'-o-chlorophenyldiguanido-$N_5$,$N_5$')hexane dihydrochloride, 1,6-di-($N_1$,$N_1$'-2,6-dichlorophenyldiguanido-$N_5$,$N_5$')hexane dihydrochloride, 1,6-di-[$N_1$,$N_1$'-beta-(p-methoxyphenyl)diguanido-$N_5$,$N_5$']hexane dihydrochloride, 1,6-di-($N_1$,$N_1$'-alpha-methyl-beta-phenyl-diguanido-$N_5$,$N_5$')hexane dihydrochloride, 1,6-di-($N_1$,$N_1$'-p-nitrophenyldiguanido-$N_5$,$N_5$')hexane dihydrochloride, omega:omega-di-($N_1$,$N_1$'-phenyldiguanido-$N_5$,$N_5$')-di-n-propyl ether dihydrochloride, omega:omega'-di-($N_1$, $N_1$'-p-chlorophenyldiguanido-$N_5$,$N_5$')-di-n-propyl ether tetrahydrochloride, 1,6-di-($N_1$,$N_1$'-2,4-dichlorophenyldiguanido-$N_5$,$N_5$')hexane tetrahydrochloride, 1,6-di-($N_1$,$N_1$'-p-methylphenyldiguanido-$N_5$,$N_5$')hexane dihydrochloride, 1,6-di-($N_1$,$N_1$'-2,4,5-trichlorophenyldiguanido-$N_5$,$N_5$')hexane tetrahydrochloride, 1,6-di-[$N_1$,$N_1$'-alpha-(p-chlorophenyl)ethyldiguanido-$N_5$,$N_5$']hexane dihydrochloride, omega:omega-di-($N_1$,$N_1$'-p-chlorophenyldiguanido-$N_5$,$N_5$')m-xylene dihydrochloride, 1,12-di-($N_1$,$N_1$'-p-chlorophenyldiguanido-$N_5$,$N_5$')dodecane dihydrochloride, 1,10-di-($N_1$,$N_1$'-phenyldiguanido-$N_5$,$N_5$')decane tetrahydrochloride, 1,12-di-($N_1$,$N_1$'-phenyldiguanido-$N_5$,$N_5$')dodecane tetrahydrochloride, 1,6-di-($N_1$,$N_1$'-o-chlorophenyl-diguanido-$N_5$,$N_5$')hexane dihydrochloride, 1,6-di-($N_1$,$N_1$'-o-chlorophenyldiguanido-$N_5$, $N_5$')hexane tetrahydrochloride, ethylene-bis(1-tolylbiguanide), ethylene-bis(p-tolylbiguanide), ethylene-bis(3,5-dimethylphenylbiguanide), ethylene-bis(p-tert-amylphenylbiguanide), ethylene-bis(nonylphenylbiguanide), ethylene-bis(phenylbiguanide), ethylene-bis(N-butylphenylbiguanide), ethylene-bis(2,5-diethoxyphenylbiguanide), ethylene-bis(2,4-dimethylphenylbiguanide), ethylene-bis(o-diphenylbiguanide), ethylene-bis(mixed amyl naphthylbiguanide), N-butylethylene-bis(phenylbiguanide), trimethylenebis(o-tolylbiguanide), N-butyl-trimethyl-bis(phenylbiguanide) and the corresponding salts such as acetates, gluconates, hydrochlorides, hydrobromides, citrates, bisulfites, fluorides, polymaleates, N-cocoalkyl sarcosinates, phosphites, hypophosphites, perfluorooctanoates, silicates, sorbates, salicylates, maleates, tartrates, fumarates, ethylenediaminetetraacetates, iminodiacetates, cinnamates, thiocyanates, arginates, pyromellitates, tetracarboxybutyrates, benzoates, glutarates, monofluorophosphates, perfluoropropionates, and any mixtures thereof. Also suitable are halogenated xylene and cresol derivatives, such as p-chlorometacresol or p-chlorometaxylene, and natural antimicrobial active ingredients of plant origin (for example from spices or herbs), animal origin and microbial origin. Preference may be given to using antimicrobial surface-active quaternary compounds, a natural antimicrobial active ingredient of plant origin and/or a natural antimicrobial active ingredient of animal origin, most preferably at least one natural antimicrobial active ingredient of plant origin from the group comprising caffeine, theobromine and theophylline and essential oils such as eugenol, thymol and geraniol, and/or at least one natural antimicrobial active ingredient of animal origin from the group comprising enzymes such as milk protein, lysozyme and lactoperoxidase, and/or at least one antimicrobial surface-active quaternary compound having an ammonium, sulfonium, phosphonium, iodonium or arsonium group, peroxo compounds and chlorine compounds. It is also possible to use substances of microbial origin, the "bacteriocines".

The quaternary ammonium compounds (QACs) which are suitable as antimicrobial active ingredients have the general formula $(R^1)(R^2)(R^3)(R^4)N^+X^-$ where $R^1$ to $R^4$ are identical or different $C_1$-$C_{22}$-alkyl radicals, $C_7$-$C_{28}$-aralkyl radicals or heterocyclic radicals, where two, or in the case of an aromatic incorporation as in pyridine, even three radicals, together with the nitrogen atom, form the heterocycle, for example a pyridinium or imidazolinium compound, and $X^-$ are halide ions, sulfate ions, hydroxide ions or similar anions. For optimal antimicrobial action, at least one of the radicals preferably has a chain length of from 8 to 18, in particular 12 to 16, carbon atoms.

QACs can be prepared by reacting tertiary amines with alkylating agents such as, for example, methyl chloride, benzyl chloride, dimethyl sulfate, dodecyl bromide, or else ethylene oxide. The alkylation of tertiary amines having one long alkyl radical and two methyl groups proceeds particularly readily, and the quaternization of tertiary amines having two long radicals and one methyl group can also be carried out with the aid of methyl chloride under mild conditions. Amines which have three long alkyl radicals or hydroxy-substituted alkyl radicals have low reactivity and are preferably quaternized using dimethyl sulfate.

Examples of suitable QACs are benzalkonium chloride (N-alkyl-N,N-dimethylbenzylammonium chloride, CAS No. 8001-54-5), benzalkone B (m,p-dichlorobenzyldimethyl-C12-alkylammonium chloride, CAS No. 58390-78-6), benzoxonium chloride (benzyldodecyl-bis(2-hydroxyethyl)ammonium chloride), cetrimonium bromide (N-hexadecyl-N,N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5) and thiazoline iodide (CAS No. 15764-48-1), and mixtures thereof. Particularly preferred QACs are the benzalkonium chlorides having $C_8$-$C_{18}$-alkyl radicals, in particular $C_{12}$-$C_{14}$-alkylbenzyldimethylammonium chloride.

Benzalkonium halides and/or substituted benzalkonium halides are commercially available, for example, as Barquat® ex Lonza, Marquat® ex Mason, Variquat® ex Witco/Sherex and Hyamine® ex Lonza, and Bardac® ex Lonza. Further commercially available antimicrobial active ingredients are N-(3-chloroallyl)hexaminium chloride such as Dowicide® and Dowicil® ex Dow, benzethonium chloride such as Hyamine® 1622 ex Rohm & Haas, methylbenzethonium chloride such as Hyamine® 10× ex Rohm & Haas, cetylpyridinium chloride such as cepacol chloride ex Merrell Labs.

The antimicrobial active ingredients are used in amounts of from 0.0001% by weight to 1% by weight, preferably from 0.001% by weight to 0.8% by weight, particularly preferably from 0.005% by weight to 0.3% by weight, and in particular from 0.01 to 0.2% by weight.

The agents may contain UV absorbers which attach to the treated textiles and improve the light stability of the fibres and/or the light stability of other formulation constituents. UV absorbers mean organic substances (light protection filters) which are able to absorb ultraviolet radiation and to emit the absorbed energy again in the form of radiation of longer wavelength, for example heat.

Compounds which have these desired properties are, for example, the compounds which are active via radiationless deactivation and derivatives of benzophenone having substituents in position(s) 2 and/or 4. Furthermore, also suitable are substituted benzotriazoles, acrylates which are phenyl-substituted in position 3 (cinnamic acid derivatives, with or without cyano groups in position 2), salicylates, organic Ni complexes and natural substances such as umbelliferone and the endogenous urocanic acid. Of particular importance are biphenyl and especially stilbene derivatives, for example those commercially available as Tinosorb® FD or Tinosorb® FR ex Ciba. UV-B absorbers which may be mentioned are: 3-benzylidenecamphor or 3-benzylidenenorcamphor and derivatives thereof, for example 3-(4-methylbenzylidene) camphor; 4-aminobenzoic acid derivatives, preferably 2-ethylhexyl 4-(dimethylamino)benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylenes); esters of salicylic acid, preferably 2-ethylhexyl salicylate, 4-isopropylbenzyl salicylate, homomethyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives such as, for example, 2,4,6-trianilino-(p-carbo-2'-ethyl-1'-hexyloxy)-1,3,5-triazine and octyltriazone, or dioctylbutamidotriazones (Uvasorb® HEB); propane-1,3-diones such as, for example, 1-(4-tert-butylphenyl)-3-(4'-methoxyphenyl) propane-1,3-dione; ketotricyclo(5.2.1.0)decane derivatives. Further suitable are 2-phenylbenzimidazole-5-sulfonic acid and its alkali metal, alkaline earth metal, ammonium, alkylammonium, alkanolammonium and glucammonium salts; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds (BASF). The UV-A and UV-B filters may of course also be used in mixtures. In addition to the said soluble substances, insoluble light protection pigments, namely finely dispersed, preferably nanoized, metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulfate or zinc stearate. The oxides and salts are already used in the form of the pigments for skin-care and skin-protective emulsions and decorative cosmetics. The particles here should have an average diameter of less than 100 nm, preferably between 5 and 50 nm, and in particular between 15 and 30 nm. They can have a spherical shape, but it is also possible to use particles which have an ellipsoidal shape or a shape deviating in some other way from the spherical form. The pigments may also be surface-treated, i.e. hydrophilicized or hydrophobicized. Typical examples are coated titanium dioxides such as, for example, titanium dioxide T 805 (Degussa) or Eusolex® T2000 (Merck); suitable hydrophobic coating agents are here preferably silicones and, particularly preferably, trialkoxyoctylsilanes or simethicones. Preference is given to using micronized zinc oxide.

The UV absorbers are usually used in amounts of from 0.01% by weight to 5% by weight, preferably from 0.03% by weight to 1% by weight.

To increase the washing or cleaning performance, agents according to the invention may contain further enzymes in addition to the α-amylase variants of the invention, wherein it is possible in principle to use any enzymes established for these purposes in the prior art. These include in particular proteases, further amylases, lipases, hemicellulases, cellulases or oxidoreductases, and preferably mixtures thereof. These enzymes are in principle of natural origin; starting from the natural molecules, improved variants for use in detergents and cleansers are available which are used with preference accordingly. Agents according to the invention preferably contain enzymes in total amounts of from $1 \times 10^{-8}$ to 5 percent by weight, based on active protein. The protein concentration may be determined with the aid of known methods, for example the BCA method (bicinchonic acid; 2,2'-biquinolyl-4,4'-dicarboxylic acid) or the biuret method (A. G. Gornall, C. S. Bardawill and M. M. David, J. Biol. Chem., 177 (1948), pp. 751-766).

Among the proteases, preference is given to those of the subtilisin type. Examples thereof include the subtilisins BPN' and Carlsberg, protease PB92, subtilisins 147 and 309, *Bacillus lentus* alkaline protease, subtilisin DY and the enzymes thermitase, proteinase K and the proteases TW3 and TW7, all of which can be classified to the subtilases but no longer to the subtilisins in the narrower sense. Subtilisin Carlsberg is available in a developed form under the trade name Alcalase® from Novozymes A/S, Bagsvaerd, Denmark. Subtilisins 147 and 309 are sold under the trade names Esperase®, and Savinase®, respectively, from Novozymes. The variants listed under the name BLAP® are derived from the protease of *Bacillus lentus* DSM 5483 (WO 91/02792 A1) and are described in particular in WO 92/21760 A1, WO 95/23221 A1, WO 02/088340 A2 and WO 03/038082 A2. The applications WO 03/054185 A1, WO 03/056017 A2, WO 03/055974 A2 and WO 03/054184 A1 reveal further usable proteases from various *Bacillus* sp. and *B. gibsonii*.

Further examples of useful proteases are the enzymes available under the trade names Durazym®, Relase®, Everlase®, Nafizym®, Natalase®, Kannase® and Ovozymes® from Novozymes, those under the trade names Purafect®, Purafect® OxP and Properase® from Genencor, that under the trade name Protosol® from Advanced Biochemicals Ltd, Thane, India, that under the trade name Wuxi® from Wuxi Snyder Bioproducts Ltd., China, those under the trade names Proleather® and Protease P® from Amano Pharmaceuticals Ltd., Nagoya, Japan, and known as proteinase K-16 from Kao Corp., Tokyo, Japan.

Examples of amylases which may be employed additionally according to the invention are the α-amylases of *Bacillus licheniformis*, of *B. amyloliquefaciens* or of *B. stearothermophilus*, and developments thereof which have been improved for use in detergents and cleansers. The *B. licheniformis* enzyme is available from Novozymes under the name Termamyl® and from Genencor under the name Purastar® ST. Development products of this α-amylase are available from Novozymes, under the names Duramyl® and Termamyl® ultra, from Genencor, under the name Purastar® OxAm, and from Daiwa Seiko Ink., Tokyo Japan, as Keistase®. The *B. amyloliquefaciens* α-amylase is sold by Novozymes under the name BAN®, and variants derived from the *B. stearothermophilus* α-amylase are sold under the names BSG® and Novamyl®, likewise from Novozymes.

Enzymes which should additionally be emphasized for this purpose are the α-amylase from *Bacillus* sp. A 7-7 (DSM 12368) disclosed in the application WO 02/10356 A2 and the cyclodextrin glucanotransferase (CGTase) from *B. agaradherens* (DSM 9948), described in the application WO 02/44350. It is further possible to use the amylolytic enzymes which belong to the sequence space of α-amylases, which is defined in the application WO 03/002711 A2, and those described in the application WO 03/054177 A2. It is also possible to use fusion products of the molecules mentioned, for example those of the application DE 10138753 A1, or point mutations thereof.

Also suitable are the developments of α-amylase from *Aspergillus niger* and *A. oryzae*, which are available under the trade name Fungamyl® from Novozymes. Other examples of commercial products which may be used are Amylase-LT® and Stainzyme®, the latter of which likewise from Novozymes.

Agents of the invention may comprise lipases or cutinases, in particular due to their triglyceride-cleaving activities, but also in order to generate peracids in situ from suitable precursors. Examples thereof include the lipases which were originally derived from *Humicola lanuginosa* (*Thermomyces lanufinosus*) or have been developed, in particular those having the D96L amino acid substitution. They are sold, for example, under the trade names Lipolase®, Lipolase® Ultra, LipoPrime®, Lipozyme® and Lipex® by Novozymes. It is furthermore possible to use, for example, the cutinases which have originally been isolated from *Fusarium solani pisi* and *Humicola insolens*. Lipases which are also useful can be obtained under the names Lipase CE®, Lipase P®, Lipase B®, or Lipase CES®, Lipase AKG®, *Bacillus* sp. Lipase®, Lipasae AP®, Lipase M-AP® and Lipase AML® from Amano. Examples of lipases and cutinases from Genencor, which can be used, are those whose starting enzymes have originally been isolated from *Pseudomonas mendocina* and *Fusarium solanii*. Other important commercial products which may be mentioned are the M1 Lipase® and Lipomax® preparations originally sold by Gist-Brocades and the enzymes sold under the names Lipase MY-30®, Lipase OF® and Lipase PL® by Meito Sangyo KK, Japan, and also the product Lumafast® from Genencor.

Agents according to the invention may, in particular when intended for the treatment of textiles, comprise cellulases, depending on the purpose either as pure enzymes, as enzyme preparations or in the form of mixtures in which the individual components advantageously complement one another with respect to their different performance aspects. These performance aspects include in particular contributions to the primary washing performance, to the secondary washing performance of the agent (antiredeposition action or graying inhibition) and finishing (fabric action), up to exerting a "stonewashed" effect.

A useful fungal, endoglucanase (EG)-rich cellulase preparation and developments thereof are supplied under the tradename Celluzyme® by Novozymes. The products Endolase® and Carezyme®, likewise available from Novozymes, are based on the *H. insolens* DSM 1800 50 kD EG and 43 kD EG respectively. Further commercial products of this company, which may be used, are Cellusoft® and Renozyme®. The latter is based on the application WO 96/29397 A1. Performance enhanced cellulase variants can be found, for example, in the application WO 98/12307 A1. It is also possible to use the cellulases disclosed in the application WO 97/14804 A1; for example the *Melanocarpus* 20 kD EG disclosed therein, which is available from AB Enzymes, Finland, under the trade names Ecostone® and Biotouch®. Further commercial products from AB Enzymes are Econase® and Ecopulp®. WO 96/34092 A2 discloses further suitable cellulases from *Bacillus* sp. CBS 670.93 and CBS 669.93, with that of *Bacillus* sp. CBS 670.93 being available under the trade name Puradax® from Genencor. Other commercial products from Genencor are "Genencor detergent cellulase L" and Indi-Age® Neutra.

Agents according to the invention may comprise further enzymes, in particular for removing particular problematic soilings, which are combined under the term hemicellulases. These include, for example, mannanases, xanthane lyases, pectin lyases (=pectinases), pectin esterases, pectate lyases, xyloglucanases (=xylanases), pullulanases and β-glucanases. Examples of suitable mannanases are available under the names Gamanase® and Pektinex AR® from Novozymes, under the name Rohapec® B1L from AB Enzymes, under the name Pyrolase® from Diversa Corp., San Diego, Calif., USA, and under the name Purabrite® from Genencor Int., Inc., Palo Alto, Calif., USA. An example of a suitable β-glucanase from a *B. alcalophilus* is revealed by the application WO 99/06573 A1. The β-glucanase obtained from *B. subtilis* is available under the name Cereflo® from Novozymes.

To enhance the bleaching action, detergents and cleansers according to the invention may comprise oxidoreductases, for example oxidases, oxygenases, katalases, peroxidases such as haloperoxidases, chloroperoxidases, bromoperoxidases, lignin peroxidases, glucose peroxidases or manganese peroxidases, dioxygenases or laccases (phenol oxidases, polyphenol oxidases). Suitable commercial products which may be mentioned are Denilite® 1 and 2 from Novozymes. Reference may be made to the application WO 98/45398 A1 with respect to examples of systems for an enzymic perhydrolysis, which may be used advantageously. WO 2004/058955 A2, for example, discloses choline oxidases useful in particular for such a system. The application WO 2004/058961 A1 reveals modified proteases having a pronounced perhydrolase activity which may likewise be used advantageously here, in particular for achieving mild bleaching in detergents for textiles. The application DE 102004029475.5 describes a combined enzymic bleaching system comprising an oxidase and a perhydrolase. WO 2005/056782 A2 also discloses further perhydrolases which may be used according to the invention. Advantageously, preferably organic, more preferably aromatic, compounds which interact with the enzymes are additionally added in order to enhance the activity of the oxidoreductases in question (enhancers), or to ensure the electron flux in the event of large differences in the redox potentials of the oxidizing enzymes and the soilings (mediators).

The enzymes used in agents according to the invention either originate from microorganisms, for example of the genera *Bacillus, Streptomyces, Humicola,* or *Pseudomonas*, and/or are produced in biotechnology processes known per se by suitable microorganisms, for example by transgenic expression hosts of the *Bacillus* genera or by filamentous fungi.

The enzymes in question are favorably purified via processes which are established per se, for example via precipitation, sedimentation, concentration, filtration of the liquid phases, microfiltration, ultrafiltration, the action of chemicals, deodorization or suitable combinations of these steps.

The enzymes may be added to the agents according to the invention in any form established in the prior art, including, for example, the solid preparations obtained by granulation, extrusion or lyophilization, or, in particular in the case of liquid or gel-like agents, solutions of the enzymes, advantageously highly concentrated, low in water and/or admixed with stabilizers.

Alternatively, the enzymes may be encapsulated both for solid and liquid forms of presentation, for example by spray-drying or extrusion of the enzyme solution together with a, preferably natural, polymer, or in the form of capsules, for example those in which the enzymes are enclosed as in a solidified gel, or in those of the core-shell type, in which an enzyme-containing core is coated with a water-, air- and/or chemical-impermeable protective layer. It is possible to additionally apply further active ingredients, for example stabilizers, emulsifiers, pigments, bleaches or dyes, in the form of layers applied thereupon. Such capsules are applied by methods known per se, for example by agitated or roll granulation or in fluidized bed processes. Advantageously, such granules are low-dusting, for example due to application of polymeric film formers, and storage-stable as a result of said coating.

It is furthermore possible to formulate two or more enzymes together, so that a single granule has a plurality of enzyme activities.

A protein and/or enzyme present in an agent of the invention may be protected, particularly during storage, from damage such as, for example, inactivation, denaturation or decay, for instance due to physical influences, oxidation or proteolytic cleavage. When said proteins and/or enzymes are produced microbially, particular preference is given to inhibiting proteolysis, in particular when the agents also comprise proteases. For this purpose, preferred agents according to the invention comprise stabilizers.

One group of stabilizers are reversible protease inhibitors. Frequently, benzamidine hydrochloride, borax, boric acids, boronic acids or salts or esters thereof are used, and of these especially derivatives having aromatic groups, for example ortho-, meta- or para-substituted phenylboronic acids, in particular 4-formylphenylboronic acid, or the salts or esters of said compounds. Peptide aldehydes, i.e. oligopeptides with reduced C terminus, in particular those composed of from 2 to 50 monomers, are also used for this purpose. Peptidic reversible protease inhibitors include inter alia ovomucoid and leupeptin. Specific, reversible peptide inhibitors of the protease subtilisin and also fusion proteins of proteases and specific peptide inhibitors are also suitable for this.

Further enzyme stabilizers are amino alcohols such as mono-, di-, triethanol- and -propanolamine and mixtures thereof, aliphatic carboxylic acids up to $C_{12}$, such as succinic acid for example, other dicarboxylic acids or salts of said acids. End group-capped fatty acid amide alkoxylates are also suitable for this purpose. Particular organic acids used as builders are capable of additionally stabilizing an enzyme present, as disclosed in WO 97/18287.

Lower aliphatic alcohols, but especially polyols such as, for example, glycerol, ethylene glycol, propylene glycol or sorbitol, are other frequently used enzyme stabilizers. Diglycerol phosphate also protects against denaturation due to physical influences. Calcium salts and/or magnesium salts are also used, for example calcium acetate or calcium formate.

Polyamide oligomers or polymeric compounds such as lignin, water-soluble vinyl copolymers or cellulose ethers, acrylic polymers and/or polyamides, stabilize the enzyme preparation inter alia to physical influences or pH fluctuations. Polyamine N-oxide-containing polymers act simultaneously as enzyme stabilizers and as color transfer inhibitors. Other polymeric stabilizers are the linear $C_8$-$C_{18}$ polyoxyalkylenes. Alkylpolyglycosides can likewise stabilize the enzymic components of the agent of the invention and are preferably able to increase in addition the performance of said components. Crosslinked N-containing compounds fulfill a double function as soil release agents and as enzyme stabilizers. Hydrophobic, nonionic polymer stabilizes in particular an optionally present cellulase.

Reducing agents and antioxidants increase the stability of the enzymes to oxidative decay; familiar examples thereof are sulfur-containing reducing agents. Other examples are sodium sulfite and reducing sugars.

Particular preference is given to using combinations of stabilizers, for example of polyols, boric acid and/or borax, the combination of boric acid or borate, reducing salts and succinic acid or other dicarboxylic acids, or the combination of boric acid or borate with polyols or polyamino compounds and with reducing salts. The action of peptide-aldehyde stabilizers can be increased advantageously by combination with boric acid and/or boric acid derivatives and polyols, and furthermore by the additional action of divalent cations, for example calcium ions.

In a preferred embodiment, agents according to the invention are characterized in that they are composed of more than one phase, for example in order to release the active ingredients separately from one another with regard to time or space. Said phases may be in various states of aggregation but in particular in the same state of aggregation.

Agents according to the invention which are composed of more than one solid component may be prepared in a simple manner by mixing various solid components, in particular powder, granules or extrudates, having various ingredients and/or different release behavior with one another in an overall loose mixture. Solid agents according to the invention which consist of one or more phases may be prepared in the known manner, for example by spray-drying or granulation, adding the enzymes and possible further thermosensitive ingredients such as, for example, bleaches, separately later, where appropriate. To prepare agents according to the invention having an increased bulk density, in particular in the range from 650 g/l to 950 g/l, preference is given to a method which has an extrusion step and has been disclosed in European patent EP 0 486 592. European patent EP 0 642 576 describes another preferred preparation with the aid of a granulation process.

Proteins may be used in dried, granulated, encapsulated, or encapsulated and additionally dried form, for example, for solid agents. They may be added separately, i.e. as a separate phase, or together with other components in the same phase, with or without compaction. If microencapsulated enzymes are to be processed in solid form, it is possible to remove the water from the aqueous solutions resulting from the workup by using methods known in the prior art, such as spray-drying, removing by centrifugation or resolubilizing. The particles obtained in this way are usually between 50 and 200 µm in size.

The encapsulated form is a way of protecting the enzymes from other components such as, for example, bleaches, or of making a controlled release possible. Depending on their size, the capsules are divided into milli-, micro- and nanocapsules, microcapsules being particularly preferred for enzymes. Another possible encapsulation method is to encapsulate the enzymes suitable for use in detergents or cleansers, starting from a mixture of the enzyme solution with a solution or suspension of starch or a starch derivative, into starch or said starch derivative.

It is also possible for least two phases to be associated with one another. Thus, compression or compacting to give tablets is another possibility of providing a solid agent according to the invention. Such tablets may have one or more phases. Consequently, this presentation form also offers the possibility of providing a two-phase solid agent according to the invention. To produce agents according to the invention in tablet form, which may have one or more phases, may have one or more colors and/or consist of one or more layers, preference is given to mixing all of the components—per one layer, where appropriate—with one another in a mixer and compressing said mixture by means of conventional tabletting presses, for example eccentric presses or rotary presses, at pressing forces in the range of from about 50 to 100 $kN/cm^2$, preferably at from 60 to 70 $kN/cm^2$. Particularly in the case of multilayer tablets, it may be of advantage if at least one layer is compressed beforehand. This is preferably accomplished at pressing forces of between 5 and 20 $kN/cm^2$, in particular at from 10 to 15 $kN/cm^2$. A tablet produced in this way preferably has a weight of from 10 g to 50 g, in particular from 15 g to 40 g. The three dimensional form of the tablets is arbitrary and may circular, oval or angular, with intermediate forms also being possible.

At least one of the phases in multi-phase agents, that contains an amylase-sensitive material, in particular starch, or is at least partially surrounded or coated by said material, is particularly advantageous. Said phase is mechanically stabilized and/or protected from influences from the outside in this way and is, at the same time, attacked via an amylase active in the wash liquor, so as to facilitate release of the ingredients.

Agents according to the invention that are likewise preferred are characterized in that they are overall in a liquid, gel-like or paste-like form. The proteins contained therein, preferably a protein of the invention, are added to such agents, preferably starting from protein isolation and preparation carried out according to the prior art, in a concentrated aqueous or nonaqueous solution, for example in liquid form, for example as solution, suspension or emulsion, but also in gel form or encapsulated or as dried powder. Such detergents or cleansers according to the invention in the form of solutions in customary solvents are usually prepared by simply mixing the ingredients which can be introduced as solids or as a solution into an automated mixer.

One embodiment of the present invention are those agents in liquid, gel or paste form, to which a protein essential to the invention and/or any of the other contained proteins and/or any of the other contained ingredients has been added in encapsulated form, preferably in the form of microcapsules. Among these, particular preference is given to those with capsules made of amylase-sensitive material. Such a combined use of amylase-sensitive materials and the amylolytic enzyme essential to the invention in a detergent or cleanser may exhibit synergistic effects, for example such that the starch-cleaving enzyme assists cleavage of the microcapsules and thus controls the process of releasing the encapsulated ingredients so that the latter are released not during storage and/or not at the beginning of the purification process but only at a particular time. This mechanism may be the basis of complex detergent and cleanser systems with a large variety of ingredients and capsule types, which are particularly preferred embodiments of the present invention.

A comparable effect arises when the ingredients of the detergent or cleanser are distributed over at least two different phases, for example two or more solid phases, connected to one another, of a tablet-like detergent or cleanser, or different granules within the same pulverulent agent. Two- or multiphase cleaners are state of the art for application both in machine dishwashers and in detergents. The activity of an amylolytic enzyme in a previously activated phase is a precondition for activation of a later phase, if the latter is surrounded by an amylase-sensitive envelope or coating or if the amylase-sensitive material is an integral component of the solid phase, which, when partially or completely hydrolyzed, leads to disintegration of the phase in question. The use of the enzyme essential to the invention for this purpose is thus a preferred embodiment of the present invention.

The ingredients of detergents and cleansers are suitably able to support each other's performance. The application WO 99/63035, for example, discloses the synergistic use of amylase and color transfer inhibitors in order to increase cleaning performance. It has also been disclosed, for example in the application WO 98/45396, that polymers which may be used simultaneously as cobuilders, such as, for example, alkyl polyglycosides, can stabilize and increase the activity and stability of enzymes present. Preference is therefore given to an α-amylase variant according to the invention being modified, in particular stabilized, and/or its contribution to the washing or cleaning performance of the agent being increased by any of the other components mentioned above. Appropriately adjusted formulations for agents according to the invention are thus particularly preferred embodiments of the present invention.

Within appropriate agents, α-amylase variants according to the invention may serve to activate their own or other phases, if they are provided alone or together with at least one other cleaning-active or cleaning action-supporting substance in a detergent or cleanser consisting of more than one phase. Accordingly, they may also serve to release ingredients from capsules, if they or another active substance are provided in encapsulated form in a detergent or cleanser.

The invention also relates to methods of cleaning textiles or hard surfaces, which are characterized in that an above-described α-amylase variant according to the invention becomes active in at least one of the process steps.

This is because this embodiment implements the invention in that the improved enzymic properties according to the invention, in particular the increased stability to multimerization, are beneficial in principle to any cleaning process, for example in that less enzyme is lost due to aggregation, even during application. Each cleaning process is enriched by the activity in question, if the latter is added in at least one process step. Processes of this kind are carried out, for example, using machines such as familiar domestic dishwashers or domestic washing machines. Preference is accordingly given to preferred processes according to the above statements.

Further preference is given to those methods which are characterized in that the α-amylase variant is employed by way of an above-described agent according to the invention.

Particular preference is given to any method characterized in that the α-amylase is employed in the step in question in an amount of from 0.01 mg to 400 mg per corresponding step, preferably from 0.02 mg to 300 mg, particularly preferably from 0.03 mg to 100 mg.

Advantageously, this results in concentrations of from 0.0005 to 20 mg per l, preferably 0.005 to 10 mg per l, particularly preferably 0.005 to 8 mg of the amylolytic protein per l of wash liquor. The protein concentration may be determined with the aid of known methods, for example the abovementioned BCA or biuret methods.

According to the above specification, the present invention is also implemented by the use of α-amylase variants of the invention because here too, the advantageous properties of the enzymes in question are effective. This applies in particular to cleaning purposes.

A separate subject matter of the invention is therefore the use of any of the above-described α-amylase variants according to the invention for cleaning textiles or hard surfaces.

It is possible here to use said variant as the sole active component, preferentially together with at least other cleaning-active or cleaning action-supporting substance.

Preference is therefore given to such a use that is characterized in that the α-amylase variant is employed by way of an above-described agent according to the invention.

Advantageously, such a use is characterized in that from 0.01 mg to 400 mg of the α-amylase variant, preferably from 0.02 mg to 300 mg, particularly preferably from 0.03 mg to 100 mg, are employed per application, preferably per application in a dishwasher or a washing machine.

This is because this produces advantageously the concentrations listed above in the wash liquor. This metering may be carried out by the manufacturer of said agent or by the end user, depending on the cleaning problem.

Another embodiment is the use of an α-amylase variant according to the invention for the treatment of raw materials or intermediate products in textile manufacture, in particular for desizing cotton.

Raw materials and intermediates in the manufacture of textiles, for example those based on cotton, are provided with starch during their production and further processing, in order to improve processing. This method which is applied to yarns, to intermediates and to textiles is called sizing. Amylolytic proteins according to the invention are suitable for removing the starch-containing protective layer (desizing), in particular because they are stabilized to multimerization during the action in a liquid medium.

The following examples further illustrate the present invention.

EXAMPLES

All molecular-biological steps are carried out following standard methods as described, for example, in the manual by Fritsch, Sambrook and Maniatis "Molecular cloning: a laboratory manual", Cold Spring Harbour Laboratory Press, New York, 1989, or comparable specialist literature. Enzymes, kits and apparatus are used according to the instructions by the respective manufacturers.

Example 1

Culturing of *Bacillus* sp. A 7-7 (DSM 12368)

The microorganism *Bacillus* sp. A 7-7 has been deposited under the deposit number DSM 12368 with the Deutsche Sammlung von Mikroorganismen und Zellkulturen GmbH, Mascheroder Weg 1b, 38124 Braunschweig, Germany (http://www.dsmz.de). It is described in the application WO 02/10356 A2. The DNA and amino acid sequences of the α-amylase produced by this (deposited) species differ from the sequences depicted in the sequence listing of WO 02/10356 A2 in the following two positions: the corresponding DNA has, in nucleic acid positions 805-807 according to SEQ ID NO. 1 of the present application, the triplet gat which codes for the amino acid D (in amino acid position 236), and, in positions 1156-1158, the triplet tat which codes for the amino acid Y (in position 353). (SEQ ID NO. 1 and 2 of WO 02/10356 A2 indicate the triplets ggt for G and tgt for C, respectively, at the corresponding positions.)

Using well-known methods of point mutagenesis, for example with the aid of the QuickChange kit from Stratagene®, La Jolla, USA (see below), and on the basis of primers derived from SEQ ID NO. 1, it is possible to convert this α-amylase to a different one.

WO 02/10356 A2 describes culturing of *Bacillus* sp. A 7-7 (DSM 12368). A suitable medium is YPSS medium containing 15 g/l soluble starch, 4 g/l yeast extract, 1 g/l $K_2HPO_4$ and 0.5 g/l $MgSO_4 \times 7H_2O$, with the pH being adjusted to 10.3 with 20% strength sodium carbonate solution after autoclaving. From this the α-amylase in question can be obtained, as likewise illustrated in WO 02/10356 A2. Thus it is possible for said α-amylase and the variants derived therefrom to be prepared by well-known methods, at least on the laboratory scale.

Example 2

Homology Modeling and Selection of the Amino Acids Replaceable According to the Invention Homology Modeling Homology modeling for *Bacillus* sp. A 7-7 (DSM 12368) α-amylase was carried out via the RSCB protein database (accessible via Max-Delbrück-Zentrum in Berlin, Germany), as illustrated in the description. In this connection, the search using the protein sequence detected the following structures: *B. licheniformis* α-amylase (RCSB-PDB database entry: 1BLI), a chimeric α-amylase of those of *B. amyloliquefaciens* and *B. licheniformis*, in its native structure (1E3X, 1E43), an acarbose complex of the same chimeric α-amylase (1E3Z), a Tris/maltotriose complex of the same chimeric α-amylase (1E40) and a kinetically stabilized variant of *B. licheniformis* α-amylase (1OB0).

By superimposing these structures in the SwissPDB viewer, a leader structure was generated onto which the protein sequence of ALBA was then modeled. The orientation of the side chains in the ALBA structure was then corrected and energy minimization was carried out. The individual steps can be found in the user manual mentioned and were carried out according to the standard settings of the program.

Overall, the following 407 amino acids are located on the surface of the molecule which comprises 484 amino acids (they are defined as such by way of an accessibility of at least 1; regarding accessibility: see description and subsequent section):

T5, N6, G7, T8, M9, Q11, Y12, E14, W15, Y16, L17, P18, N19, D20, G21, N22, H23, W24, N25, R26, R28, S29, D30, A31, S32, N33, K35, D36, K37, G38, I39, T40, A41, W43, P46, A47, W48, K49, G50, A51, S52, Q53, N54, D55, V56, G57, Y58, G59, A60, Y61, D62, L63, Y64, L66, G67, E68, F69, N70, Q71, K72, G73, T74, V75, R76, T77, K78, Y79, G80, T81, R82, N83, Q84, L85, Q86, A87, V89, T90, A91, K93, S94, N95, G96, Q98, V99, Y100, V103, M105, N106, H107, K108, G110, A111, D112, A113, T114, E115, W116, V117, R118, V120, E121, V122, N123, P124, S125, N126, R127, N128, Q129, E130, V131, S132, G133, D134, Y135, T136, I137, E138, W140, K142, F143, D144, F145, P146, G147, R148, G149, N150, T151, H152, S153, N154, F155, K156, W157, R158, W159, Y160, H161, D166, W167, D168, Q169, S170, R171, Q172, L173, Q174, N175, R176, I177, Y178, K179, R181, G182, D183, G184, K185, G186, W187, W189, E190, V191, D192, T193, E194, N195, G196, N197, Y198, D199, Y200, L201, M202, Y203, I206, D207, M208, D209, H210, P211, E212, V214, N215, E216, L217, R218, N219, V222, W223, R225, N226, T227, L228, G229, L230, D231, F233, R234, I235, G236, A237, K239, H240, I241, K242, Y243, S244, F245, T246, R247, D248, W249, L250, T251, H252, V253, R254, N255, T256, T257, G258, K259, N260, M261, F262, A263, E266, F267, W268, K269, N270, D271, I272, G273, A274, I275, E276, N277, S280, K281, N283, W284, N285, H286, S287, V288, F289, P292, L293, Y295, N296, L297, Y298, N299, S301, R302, S303, G304, G305, N306, Y307, D308, M309, R310, Q311, I312, F313, N314, G315, V318, Q319, R320, H321, P322, T323, H324, T327, F328, V329, D330, N331, H332, D333, Q335, P336, E337, E338, A339, L340, E341, S342, F343, E345, E346, W347, F348, K349, P350, L351, C353, L355, T356, L357, R359, D360, Q361, G362, Y363, S365, V366, F367, Y368, D370, Y371, Y372, G373, I374, P375, T376, H377, G378, P380, A381, M382, K383, S384, K385, I386, D387, P388, L390, E391, R393, Q394, K395, Y396, Y398, G399, K400, Q401, N402, D403, Y404, L405, D406, H407, H408, N409, M410, R415, E416, G417, N418, T419, A420, H421, P422, N423, S424, M430, D432, G433, P434, G435, G436, N437, K438, W439, Y441, G443, R444, N445, K446, A447, G448, Q449, V450, W451, R452, D453, I454, T455, G456, N457, R458, S459, G460, T461, V462, T463, I464, N465, A466, D467, W469, N471, S473, V474, N475, G476, G477, S478, V479, V483, N484, N485

Calculation of the Surface Amino Acid Residues Contributing to the Electrostatic Potential of the Whole Molecule Determination of the three-dimensional structure is followed by a calculation of the particular contributions of the amino acids on the surface to the electrostatic potential of the whole molecule. This calculation too was carried out as specified in the description, using the corresponding function of the mentioned SwissPDB viewer with standard parameters. Such contributions are made both by neutral and negatively charged amino acid residues and by those which themselves are neutral but cover a charge further inside the molecule. This is therefore a projection of the charges onto the molecular surface.

The result thereof is depicted in FIG. 1: the three-dimensional representation of the Conolly surface of *Bacillus* sp. A 7-7 (DSM 12368) α-amylase is visible there, with the charge and polarity distribution being highlighted by color (white, gray and black). Overall, the following 118 amino acid residues of the *Bacillus* sp. A 7-7 (DSM 12368) α-amylase molecule make a positive or neutral contribution to the electrostatic potential of the surface:

T5, N6, G7, T8, N19, G21, N22, H23, N25, R26, R28, S29, A31, S32, N33, K35, K37, G38, K49, Q53, L66, K72, T74, V75, R76, K78, T81, R82, N83, Q84, L85, Q86, A87, V89, T90, A91, K93, S94, N95, G96, Q98, K108, R118, T136, K142, G149, N150, T151, H152, N154, K156, R158, Y160, H161, R171, Q172, R176, R181, R218, T227, L228, G229, K242, R247, T251, R254, K259, N260, K281, N283, R302, R310, R320, T323, R359, Y368, Y372, T376, K383, K385, R393, Q394, K395, Y398, G399, K400, Y404, M410, R415, G417, N418, T419, A420, H421, P422, G435, G436, K438, W439, R444, N445, K446, Q449, V450, R452, R458, S459, G460, T461, V462, T463, N465, A466, N471, S473, N475, G476, N484.

Calculation of Solvent Accessibility

Based on these results, the solvent accessibility of the above-described amino acid residues which are located on the surface and make a positive or neutral contribution to the charge or polarity of the whole molecule were then calculated. To this end, the above-mentioned SwissPdb viewer was used again, preserving the standard parameters of the program. As a result, the following amino acid residues were determined the solvent accessibility values being indicated in each case in % in brackets after the positions listed:

T5 (39), N6 (12), G7 (13), N19 (28), N22 (28), N25 (16), R26 (27), R28 (39), S29 (38), S32 (28), N33 (28), K35 (37), K37 (18), Q53 (12), K72 (27), V75 (30), R76 (24), T81 (16), R82 (22), N83 (44), Q84 (24), Q86 (18), A87 (18), T90 (30), A91 (11), K93 (32), S94 (50), N95 (19), G96 (25), Q98 (29), R118 (41), T136 (22), K142 (30), G149 (14), N150 (39), T151 (22), H152 (27), N154 (41), K156 (30), R158 (33), Y160 (20), R171 (32), Q172 (53), R176 (41), R181 (34), R218 (18), T227 (19), G229 (14), K242 (15), R247 (20), T251 (23), R254 (15), K259 (26), N260 (49), K281 (33), N283 (40), R302 (50), R310 (31), R320 (52), T323 (49), R359 (13), Y368 (12), Y372 (37), T376 (56), K383 (19), K385 (37), Q394 (20), K395 (38), G399 (16), K400 (44), Y404 (11), N418 (25), T419 (59), A420 (37), H421 (16), P422 (46), G435 (25), G436 (17), W439 (47), R444 (49), N445 (41), Q449 (31), V450 (24), R452 (33), R458 (24), S459 (52), G460 (32), T461 (35), T463 (40), N465 (22), A466 (37), N471 (20), S473 (10), N475 (25), G476 (31), N484 (12).

These are thus the 97 amino acid residues of the 484 amino acids in total of the *Bacillus* sp. A 7-7 (DSM 12368) α-amylase molecule, which make a positive or neutral contribution to the electrostatic potential of the surface and additionally have an accessibility of at least 10%.

The remaining 21 surface amino acids which had been determined previously as those making a neutral or positive contribution but having an accessibility of less than 10% are the following, with the corresponding value again being indicated in brackets:

T8 (2), G21 (4), H23 (2), A31 (2), G38 (6), K49 (2), L66 (2), T74 (6), K78 (6), L85 (2), V89 (1), K108 (9), H161 (1), L228 (1), R393 (5), Y398 (4), M410 (3), R415 (6), K438 (7), K446 (5), V462 (5).

Grouping of the Neutral or Positively Charged or Polarized Amino Acid Residues Particularly Accessible to the Solvent The 97 identified residues having an accessibility of at least 10% may be assigned to various groups according to their location on the surface of said α-amylase, with those of groups A and B representing in each case contiguous regions of neutral or positive polarity or charge. Group A below comprises the 63 amino acid residues among them, which form a contiguous surface with neutral or positive electrostatic potential (with the previously determined accessibility again in brackets):

(A) T5 (39), N6 (12), G7 (13), N19 (28), N22 (28), N25 (16), R26 (27), R28 (39), S29 (38), S32 (28), N33 (28), K35 (37), K37 (18), Q53 (12), K72 (27), V75 (30), R76 (24), T81 (16), R82 (22), N83 (44), Q84 (24), Q86 (18), A87 (18), T90 (30), A91 (11), K93 (32), S94 (50), N95 (19), G96 (25), Q98 (29), R118 (41), T136 (22), K142 (30), G149 (14), N150 (39), T151 (22), H152 (27), N154 (41), K156 (30), R158 (33), Y160 (20), R171 (32), Q172 (53), R181 (34), T227 (19), G229 (14), R247 (20), T251 (23), R254 (15), K259 (26), N260 (49), K281 (33), N283 (40), Q394 (20), K395 (38), G399 (16), K400 (44), G417 (11), N418 (25), T419 (59), A420 (37), H421 (16), P422 (46).

Group B below comprises the 20 amino acid residues forming a second contiguous surface with a neutral or positive electrostatic potential:

(B) G435 (25), G436 (17), W439 (47), R444 (49), N445 (41), Q449 (31), V450 (24), R452 (33), R458 (24), S459 (52), G460 (32), T461 (35), T463 (40), N465 (22), A466 (37), N471 (20), S473 (10), N475 (25), G476 (31), N484 (12).

Group C below comprises the remaining 14 amino acid residues which cannot be assigned to any of said two larger areas but occur isolated:

(C) R176 (41), R218 (18), K242 (15), R302 (50), R310 (31), R320 (52), T323 (49), R359 (13), Y368 (12), Y372 (37), T376 (56), K383 (19), K385 (37), Y404 (11).

The amino acids belonging to groups A and B, in particular, can be assumed to contribute with their contributions to a contiguous surface charge to the observed tendency of charge- and/or polarity-mediated di- and/or multimerization and therefore to aggregation.

Example 3

Site-Specific Mutagenesis

For *Bacillus* sp. A 7-7 (DSM 12368) α-amylase, the positions determined in the previous example serve as starting points for point mutations via site-directed mutagenesis, i.e. for introducing a different amino acid to the position(s) in question. Said mutagenesis is carried out, for example, with the aid of the QuikChange kit (Stratagene, cat. No. 200518) according to the corresponding protocol. The primers may be designed on the basis of the DNA and amino acid sequences indicated in SEQ ID NO. 1, the particular codon being altered according to the amino acid to be introduced. This involves the possible amino acid substitutions below for generating a less neutral or positive polarity or charge, i.e. for introducing a rather negative polarity or charge:

| Starting amino acid | to give |
|---|---|
| Arg (R) | K, Y, C, H, G, A, V, L, I, M, F, W, P, S, T, N, Q, E or D |
| Lys (K) | Y, C, H, G, A, V, L, I, M, F, W, P, S, T, N, Q, E or D |
| Tyr (Y) | C, H, G, A, V, L, I, M, F, W, P, S, T, N, Q, E or D |
| Cys (C) | H, G, A, V, L, I, M, F, W, P, S, T, N, Q, E or D |
| His (H) | G, A, V, L, I, M, F, W, P, S, T, N, Q, E or D |
| Gly (G) | A, V, L, I, M, F, W, P, S, T, N, Q, E or D |
| Ala (A) | V, L, I, M, F, W, P, S, T, N, Q, E or D |
| Val (V) | L, I, M, F, W, P, S, T, N, Q, E or D |
| Leu (L) | I, M, F, W, P, S, T, N, Q, E or D |
| Ile (I) | M, F, W, P, S, T, N, Q, E or D |

| Starting amino acid | to give |
|---|---|
| Met (M) | F, W, P, S, T, N, Q, E or D |
| Phe (F) | W, P, S, T, N, Q, E or D |
| Trp (W) | P, S, T, N, Q, E or D |
| Pro (P) | S, T, N, Q, E or D |
| Ser (S) | T, N, Q, E or D |
| Thr (T) | N, Q, E or D |
| Asn (N) | Q, E or D |
| Gln (Q) | E or D |
| Glu (E) | D |

To this end, the codon in the gene sequence of the α-amylase in question is thus replaced with a codon of the amino acid to be introduced. According to this principle, an expression vector containing the α-amylase sequence is suitably mutagenized accordingly and transformed into an expression strain in the present example into *B. subtilis*, by well-known methods.

Example 4

Production and Purification of Amylase Mutants

Amylase-positive *B. subtilis* strains are grown in the YPSS medium mentioned in Example 1. This procedure and purification of the enzyme produced by these strains are carried out according to the description in WO 02/10356 A2. The latter also reveals determination of the amylolytic activity of the purified enzyme according to the "DNS method". The activity determinable in this way serves hereinbelow as parameter for the stability of the enzyme under in each case different conditions.

Determination of Aggregate Formation

The formation of multimers and precipitate is detected by way of the turbidity of an amylase-containing solution having an amylase content of at least 5 mg/ml spectrometrically at a wavelength of 600 nm. Mutants according to the invention exhibit a reduced tendency to form precipitate after 16 hours of incubation at a concentration of at least 5 mg/ml protein in buffer or culture medium at 25° C., which tendency is expressed as a reduced increase in absorption at 600 nm.
Abbreviations:

| | |
|---|---|
| A 7-7: | α-amylase of *Bacillus* sp. A 7-7 (DSM 12368; SEQ ID NO. 2) |
| S707: | α-amylase of *Bacillus* sp. #707 (SEQ ID NO. 3) |
| LAMY: | α-amylase of *Bacillus* sp. KSM-AP1378 (SEQ ID NO. 4) |
| BAA: | α-amylase of *B. amyloliquefaciens* (SEQ ID NO. 5) |
| BLA: | α-amylase of *B. licheniformis* (SEQ ID NO. 6) |
| BStA: | α-amylase of *B. stearothermophilus* (SEQ ID NO. 7) |
| MK716: | α-amylase of *Bacillus* sp. MK716 (SEQ ID NO. 8) |
| TS-23: | α-amylase of *Bacillus* sp. TS-23 (SEQ ID NO. 9) |
| K38: | α-amylase of *Bacillus* sp. KSM-K38 (SEQ ID NO. 10) |

The invention claimed is:

1. An α-amylase variant of the α-amylase of Bacillus sp. A 7-7 (DSM 12368) according to positions +1 to 484 of SEQ ID NO. 2 and having α-amylase activity, the variant having a plurality of amino acid substitutions with respect to the α-amylase starting molecule, wherein the α-amylase variant differs from the α-amylase starting molecule by substitution of a plurality of predetermined starting amino acid residues at the surface of the molecule making a neutral or positively polar or charged contribution to the electrostatic potential of said molecule with more negatively polar or negatively charged substituted amino acid residues, thereby providing increased stability to aggregate formation, wherein the amino acid substitutions are chosen from the following substitutions:

| Starting amino acid | Substituted amino acid |
|---|---|
| Arg (R) | K, Y, C, H, G, A, V, L, I, M, F, W, P, S, T, N, Q, E or D |
| Lys (K) | Y, C, H, G, A, V, L, I, M, F, W, P, S, T, N, Q, E or D |
| Trp (W) | P, S, T, N, Q, E or D |
| Pro (P) | S, T, N, Q, E or D |
| Ser (S) | T, N, Q, E or D |
| Thr (T) | N, Q, E or D |
| Asn (N) | Q, E or D |
| Gln (Q) | E or D | wherein said starting amino acid residues are selected from the following positions:
83, 94, 118, 154, 172, 176, 260, 283, 302, 320, 323, 376, 400, 419, 422,
439, 444, 445, 459, and 463,
in each case indicated in the numbering of the mature protein according to SEQ ID NO. 2,
wherein the amino acid substitutions are limited to two or more of the listed positions, and
wherein the number of substitutions is up to 20.

2. A detergent or cleaning agent comprising an α-amylase variant according to claim 1.

3. An agent according to claim 2, comprising from 0.000001 percent by weight to 5% by weight of the α-amylase variant.

4. An agent according to claim 2, further including at least one addition enzyme selected from the group consisting of amylases, proteases, lipases, cutinases, hemicellulases, cellulases, β-glucanases, oxidases, peroxidases, perhydrolases and laccases.

5. An agent according to claim 2, wherein the α-amylase variant is stabilized and/or its contribution to the washing or cleaning performance of the agent is increased by at least one additional component.

6. An agent according to claim 2, the agent being a solid including at least one compacted component.

7. An agent according to claim 2, the agent being liquid, gel-like or paste-like, the α-amylase variant being encapsulated.

8. A method of cleaning textiles or hard surfaces, the method comprising:
   (a) applying an agent including at least one α-amylase variant according to claim 1 to a textile of hard surface substrate, and
   (b) activating the at least one α-amylase variant.

9. A method according to claim 8, wherein the agent comprises from 0.01 mg to 400 mg of the at least one α-amylase variant.

\* \* \* \* \*

SEQUENCE LISTING

```
<160> NUMBER OF SEQ ID NOS: 10

<210> SEQ ID NO 1
<211> LENGTH: 1554
<212> TYPE: DNA
<213> ORGANISM: Bacillus sp. A 7-7 (DSM 12368)
<220> FEATURE:
<221> NAME/KEY: gene
<222> LOCATION: (1)..(1554)
<223> OTHER INFORMATION: alpha-Amylase
<220> FEATURE:
<221> NAME/KEY: CDS
<222> LOCATION: (1)..(1551)
<220> FEATURE:
<221> NAME/KEY: mat_peptide
<222> LOCATION: (100)..()

<400> SEQUENCE: 1 atg acg atg aga aaa cgt aaa aat gga tta atc agt att cta ttg gca    48
  Met Thr Met Arg Lys Arg Lys Asn Gly Leu Ile Ser Ile Leu Leu Ala
          -30              -25                 -20
```

```
ttt ttg ttg gta ctt aca tca ata cct ttt act tca gca aac gta gaa        96
Phe Leu Leu Val Leu Thr Ser Ile Pro Phe Thr Ser Ala Asn Val Glu
        -15              -10                  -5 gca cac cat aat ggc aca aat gga aca atg atg caa tat ttt gaa tgg       144
Ala His His Asn Gly Thr Asn Gly Thr Met Met Gln Tyr Phe Glu Trp
 -1  1              5                   10                  15 tat ttg cca aat gac ggt aat cat tgg aat aga tta aga tca gat gca       192
Tyr Leu Pro Asn Asp Gly Asn His Trp Asn Arg Leu Arg Ser Asp Ala
                 20                  25                  30 agt aat ctt aaa gat aaa ggg att aca gcg gtt tgg att cca cct gct       240
Ser Asn Leu Lys Asp Lys Gly Ile Thr Ala Val Trp Ile Pro Pro Ala
             35                  40                  45 tgg aaa ggg gct tct caa aat gat gta ggg tat gga gcc tat gat ctg       288
Trp Lys Gly Ala Ser Gln Asn Asp Val Gly Tyr Gly Ala Tyr Asp Leu
         50                  55                  60 tat gat tta gga gaa ttc aat caa aaa gga acc gta cgt aca aag tac       336
Tyr Asp Leu Gly Glu Phe Asn Gln Lys Gly Thr Val Arg Thr Lys Tyr
     65                  70                  75 gga acc cgt aat caa tta caa gct gca gta acc gcc tta aaa agt aat       384
Gly Thr Arg Asn Gln Leu Gln Ala Ala Val Thr Ala Leu Lys Ser Asn
 80                  85                  90                  95 ggt att caa gta tac gga gat gtc gta atg aat cat aag ggt gga gcg       432
Gly Ile Gln Val Tyr Gly Asp Val Val Met Asn His Lys Gly Gly Ala
                 100                 105                 110 gat gcc act gag tgg gtt cga gcg gtt gaa gtg aac cca agt aat cgt       480
Asp Ala Thr Glu Trp Val Arg Ala Val Glu Val Asn Pro Ser Asn Arg
             115                 120                 125 aat caa gaa gtc tct ggt gat tat acg att gag gct tgg act aag ttt       528
Asn Gln Glu Val Ser Gly Asp Tyr Thr Ile Glu Ala Trp Thr Lys Phe
         130                 135                 140 gat ttt cct ggt cga ggt aat acc cac tct aac ttt aaa tgg aga tgg       576
Asp Phe Pro Gly Arg Gly Asn Thr His Ser Asn Phe Lys Trp Arg Trp
     145                 150                 155 tat cat ttc gat ggt gta gat tgg gat cag tca cgt caa ttg cag aat       624
Tyr His Phe Asp Gly Val Asp Trp Asp Gln Ser Arg Gln Leu Gln Asn
 160                 165                 170                 175 cga atc tat aaa ttc aga gga gat gga aaa ggt tgg gac tgg gaa gtt       672
Arg Ile Tyr Lys Phe Arg Gly Asp Gly Lys Gly Trp Asp Trp Glu Val
                 180                 185                 190 gat aca gag aac gga aac tat gac tat cta atg tac gcg gat att gat       720
Asp Thr Glu Asn Gly Asn Tyr Asp Tyr Leu Met Tyr Ala Asp Ile Asp
             195                 200                 205 atg gat cac cct gaa gta gtg aat gaa ctc aga aac tgg ggt gta tgg       768
Met Asp His Pro Glu Val Val Asn Glu Leu Arg Asn Trp Gly Val Trp
         210                 215                 220 tat acc aat aca ctg ggg cta gac ggg ttc aga ata gat gcg gta aaa       816
Tyr Thr Asn Thr Leu Gly Leu Asp Gly Phe Arg Ile Asp Ala Val Lys
     225                 230                 235 cat ata aaa tat agc ttt act cgt gat tgg ctt act cac gtt aga aat       864
His Ile Lys Tyr Ser Phe Thr Arg Asp Trp Leu Thr His Val Arg Asn
 240                 245                 250                 255 acg aca ggt aaa aat atg ttt gca gtt gca gag ttc tgg aag aat gac       912
Thr Thr Gly Lys Asn Met Phe Ala Val Ala Glu Phe Trp Lys Asn Asp
                 260                 265                 270 ata ggt gca att gaa aat tac tta agt aaa aca aat tgg aat cat tca       960
Ile Gly Ala Ile Glu Asn Tyr Leu Ser Lys Thr Asn Trp Asn His Ser
             275                 280                 285 gtt ttt gat gtg ccc ctg cat tat aac ctt tat aat gca tcg aga agt      1008
Val Phe Asp Val Pro Leu His Tyr Asn Leu Tyr Asn Ala Ser Arg Ser
```

```
                 290                 295                 300
ggt ggc aat tat gat atg agg caa ata ttt aat gga aca gtt gtt cag      1056
Gly Gly Asn Tyr Asp Met Arg Gln Ile Phe Asn Gly Thr Val Val Gln
305                 310                 315 aga cat cct aca cat gct gta aca ttt gtt gat aac cat gat tca cag      1104
Arg His Pro Thr His Ala Val Thr Phe Val Asp Asn His Asp Ser Gln
320                 325                 330                 335 ccg gaa gaa gcc cta gag tca ttt gtt gaa gag tgg ttc aaa ccg tta      1152
Pro Glu Glu Ala Leu Glu Ser Phe Val Glu Glu Trp Phe Lys Pro Leu
            340                 345                 350 gcg tat gct ctc aca cta aca cgt gat caa gga tat cct tcc gtt ttt      1200
Ala Tyr Ala Leu Thr Leu Thr Arg Asp Gln Gly Tyr Pro Ser Val Phe
        355                 360                 365 tat gga gat tat tat ggg att ccg acg cat ggt gta cca gca atg aaa      1248
Tyr Gly Asp Tyr Tyr Gly Ile Pro Thr His Gly Val Pro Ala Met Lys
    370                 375                 380 tct aag att gat ccg att tta gaa gca cgt caa aag tat gcg tac gga      1296
Ser Lys Ile Asp Pro Ile Leu Glu Ala Arg Gln Lys Tyr Ala Tyr Gly
385                 390                 395 aaa caa aat gat tat ttg gat cac cat aat atg att ggc tgg acg cgt      1344
Lys Gln Asn Asp Tyr Leu Asp His His Asn Met Ile Gly Trp Thr Arg
400                 405                 410                 415 gaa ggt aat aca gca cat ccc aac tca gga cta gca act att atg tcg      1392
Glu Gly Asn Thr Ala His Pro Asn Ser Gly Leu Ala Thr Ile Met Ser
            420                 425                 430 gat ggc cca gga gga aat aaa tgg atg tat gtt ggg cgt aat aag gct      1440
Asp Gly Pro Gly Gly Asn Lys Trp Met Tyr Val Gly Arg Asn Lys Ala
        435                 440                 445 gga caa gtt tgg aga gat att aca gga aat cgc tca ggt acg gtg acg      1488
Gly Gln Val Trp Arg Asp Ile Thr Gly Asn Arg Ser Gly Thr Val Thr
    450                 455                 460 att aac gca gat ggg tgg ggt aat ttt tct gta aat ggt ggg tct gta      1536
Ile Asn Ala Asp Gly Trp Gly Asn Phe Ser Val Asn Gly Gly Ser Val
465                 470                 475 tct ata tgg gta aat aat                                              1554
Ser Ile Trp Val Asn Asn
480

<210> SEQ ID NO 2
<211> LENGTH: 517
<212> TYPE: PRT
<213> ORGANISM: Bacillus sp. A 7-7 (DSM 12368)

<400> SEQUENCE: 2

Met Thr Met Arg Lys Arg Lys Asn Gly Leu Ile Ser Ile Leu Leu Ala
            -30                 -25                 -20

Phe Leu Leu Val Leu Thr Ser Ile Pro Phe Thr Ser Ala Asn Val Glu
        -15                 -10                  -5

Ala His His Asn Gly Thr Asn Gly Thr Met Met Gln Tyr Phe Glu Trp
 -1   1               5                  10                  15

Tyr Leu Pro Asn Asp Gly Asn His Trp Asn Arg Leu Arg Ser Asp Ala
                 20                  25                  30

Ser Asn Leu Lys Asp Lys Gly Ile Thr Ala Val Trp Ile Pro Pro Ala
             35                  40                  45

Trp Lys Gly Ala Ser Gln Asn Asp Val Gly Tyr Gly Ala Tyr Asp Leu
         50                  55                  60

Tyr Asp Leu Gly Glu Phe Asn Gln Lys Gly Thr Val Arg Thr Lys Tyr
     65                  70                  75
```

```
Gly Thr Arg Asn Gln Leu Gln Ala Ala Val Thr Ala Leu Lys Ser Asn
 80              85                  90                  95

Gly Ile Gln Val Tyr Gly Asp Val Val Met Asn His Lys Gly Gly Ala
            100                 105                 110

Asp Ala Thr Glu Trp Val Arg Ala Val Glu Val Asn Pro Ser Asn Arg
            115                 120                 125

Asn Gln Glu Val Ser Gly Asp Tyr Thr Ile Glu Ala Trp Thr Lys Phe
        130                 135                 140

Asp Phe Pro Gly Arg Gly Asn Thr His Ser Asn Phe Lys Trp Arg Trp
        145                 150                 155

Tyr His Phe Asp Gly Val Asp Trp Asp Gln Ser Arg Gln Leu Gln Asn
160                 165                 170                 175

Arg Ile Tyr Lys Phe Arg Gly Asp Gly Lys Gly Trp Asp Trp Glu Val
            180                 185                 190

Asp Thr Glu Asn Gly Asn Tyr Asp Tyr Leu Met Tyr Ala Asp Ile Asp
            195                 200                 205

Met Asp His Pro Glu Val Val Asn Glu Leu Arg Asn Trp Gly Val Trp
        210                 215                 220

Tyr Thr Asn Thr Leu Gly Leu Asp Gly Phe Arg Ile Asp Ala Val Lys
225                 230                 235

His Ile Lys Tyr Ser Phe Thr Arg Asp Trp Leu Thr His Val Arg Asn
240                 245                 250                 255

Thr Thr Gly Lys Asn Met Phe Ala Val Ala Glu Phe Trp Lys Asn Asp
            260                 265                 270

Ile Gly Ala Ile Glu Asn Tyr Leu Ser Lys Thr Asn Trp Asn His Ser
            275                 280                 285

Val Phe Asp Val Pro Leu His Tyr Asn Leu Tyr Asn Ala Ser Arg Ser
        290                 295                 300

Gly Gly Asn Tyr Asp Met Arg Gln Ile Phe Asn Gly Thr Val Val Gln
        305                 310                 315

Arg His Pro Thr His Ala Val Thr Phe Val Asp Asn His Asp Ser Gln
320                 325                 330                 335

Pro Glu Glu Ala Leu Glu Ser Phe Val Glu Glu Trp Phe Lys Pro Leu
            340                 345                 350

Ala Tyr Ala Leu Thr Leu Thr Arg Asp Gln Gly Tyr Pro Ser Val Phe
            355                 360                 365

Tyr Gly Asp Tyr Tyr Gly Ile Pro Thr His Gly Val Pro Ala Met Lys
        370                 375                 380

Ser Lys Ile Asp Pro Ile Leu Glu Ala Arg Gln Lys Tyr Ala Tyr Gly
        385                 390                 395

Lys Gln Asn Asp Tyr Leu Asp His His Asn Met Ile Gly Trp Thr Arg
400                 405                 410                 415

Glu Gly Asn Thr Ala His Pro Asn Ser Gly Leu Ala Thr Ile Met Ser
            420                 425                 430

Asp Gly Pro Gly Gly Asn Lys Trp Met Tyr Val Gly Arg Asn Lys Ala
            435                 440                 445

Gly Gln Val Trp Arg Asp Ile Thr Gly Asn Arg Ser Gly Thr Val Thr
            450                 455                 460

Ile Asn Ala Asp Gly Trp Gly Asn Phe Ser Val Asn Gly Gly Ser Val
        465                 470                 475

Ser Ile Trp Val Asn
480
```

```
<210> SEQ ID NO 3
<211> LENGTH: 485
<212> TYPE: PRT
<213> ORGANISM: Bacillus sp. #707

<400> SEQUENCE: 3

His His Asn Gly Thr Asn Gly Thr Met Met Gln Tyr Phe Glu Trp Tyr
 1               5                  10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Gln Ala Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Ala Thr Glu Met Val Arg Ala Val Glu Val Asn Pro Asn Asn Arg Asn
    115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380
```

```
Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 4
<211> LENGTH: 485
<212> TYPE: PRT
<213> ORGANISM: Bacillus sp. KSM-AP1378

<400> SEQUENCE: 4

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Gly Ala Val Thr Ser Leu Lys Asn Asn Gly
            85                  90                  95

Ile Gln Val Tyr Gly Asp Val Val Met Asn His Lys Gly Gly Ala Asp
        100                 105                 110

Gly Thr Glu Met Val Asn Ala Val Glu Val Asn Arg Ser Asn Arg Asn
    115                 120                 125

Gln Glu Ile Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Thr Asp Trp Asp Gln Ser Arg Gln Leu Gln Asn Lys
            165                 170                 175

Ile Tyr Lys Phe Arg Gly Thr Gly Lys Ala Trp Asp Trp Glu Val Asp
        180                 185                 190

Ile Glu Asn Gly Asn Tyr Asp Tyr Leu Met Tyr Ala Asp Ile Asp Met
    195                 200                 205

Asp His Pro Glu Val Ile Asn Glu Leu Arg Asn Trp Gly Val Trp Tyr
210                 215                 220

Thr Asn Thr Leu Asn Leu Asp Gly Phe Arg Ile Asp Ala Val Lys His
225                 230                 235                 240

Ile Lys Tyr Ser Tyr Thr Arg Asp Trp Leu Thr His Val Arg Asn Thr
            245                 250                 255

Thr Gly Lys Pro Met Phe Ala Val Ala Glu Phe Trp Lys Asn Asp Leu
        260                 265                 270
```

```
Ala Ala Ile Glu Asn Tyr Leu Asn Lys Thr Ser Trp Asn His Ser Val
        275                 280                 285

Phe Asp Val Pro Leu His Tyr Asn Leu Tyr Asn Ala Ser Asn Ser Gly
        290                 295                 300

Gly Tyr Phe Asp Met Arg Asn Ile Leu Asn Gly Ser Val Val Gln Lys
305                 310                 315                 320

His Pro Ile His Ala Val Thr Phe Val Asp Asn His Asp Ser Gln Pro
                325                 330                 335

Gly Glu Ala Leu Glu Ser Phe Val Gln Ser Trp Phe Lys Pro Leu Ala
                340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Gly Val Pro Ser Met Lys Ser
370                 375                 380

Lys Ile Asp Pro Leu Leu Gln Ala Arg Gln Thr Tyr Ala Tyr Gly Thr
385                 390                 395                 400

Gln His Asp Tyr Phe Asp His His Asp Ile Ile Gly Trp Thr Arg Glu
                405                 410                 415

Gly Asp Ser Ser His Pro Asn Ser Gly Leu Ala Thr Ile Met Ser Asp
                420                 425                 430

Gly Pro Gly Gly Asn Lys Trp Met Tyr Val Gly Lys His Lys Ala Gly
        435                 440                 445

Gln Val Trp Arg Asp Ile Thr Gly Asn Arg Ser Gly Thr Val Thr Ile
        450                 455                 460

Asn Ala Asp Gly Trp Gly Asn Phe Thr Val Asn Gly Gly Ala Val Ser
465                 470                 475                 480

Val Trp Val Lys Gln
                485

<210> SEQ ID NO 5
<211> LENGTH: 483
<212> TYPE: PRT
<213> ORGANISM: Bacillus amyloliquefaciens

<400> SEQUENCE: 5

Val Asn Gly Thr Leu Met Gln Tyr Phe Glu Trp Tyr Thr Pro Asn Asp
1               5                   10                  15

Gly Gln His Trp Lys Arg Leu Gln Asn Asp Ala Glu His Leu Ser Asp
                20                  25                  30

Ile Gly Ile Thr Ala Val Trp Ile Pro Pro Ala Tyr Lys Gly Leu Ser
        35                  40                  45

Gln Ser Asp Asn Gly Tyr Gly Pro Tyr Asp Leu Tyr Asp Leu Gly Glu
    50                  55                  60

Phe Gln Gln Lys Gly Thr Val Arg Thr Lys Tyr Gly Thr Lys Ser Glu
65                  70                  75                  80

Leu Gln Asp Ala Ile Gly Ser Leu His Ser Arg Asn Val Gln Val Tyr
                85                  90                  95

Gly Asp Val Val Leu Asn His Lys Ala Gly Ala Asp Ala Thr Glu Asp
            100                 105                 110

Val Thr Ala Val Glu Val Asn Pro Ala Asn Arg Asn Gln Glu Thr Ser
        115                 120                 125

Glu Glu Tyr Gln Ile Lys Ala Trp Thr Asp Phe Arg Phe Pro Gly Arg
    130                 135                 140

Gly Asn Thr Tyr Ser Asp Phe Lys Trp His Trp Tyr His Phe Asp Gly
```

```
            145                 150                 155                 160
Ala Asp Trp Asp Glu Ser Arg Lys Ile Ser Arg Ile Phe Lys Phe Arg
                165                 170                 175

Gly Glu Gly Lys Ala Trp Asp Trp Glu Val Ser Ser Glu Asn Gly Asn
                180                 185                 190

Tyr Asp Tyr Leu Met Tyr Ala Asp Val Asp Tyr Asp His Pro Asp Val
                195                 200                 205

Val Ala Glu Thr Lys Lys Trp Gly Ile Trp Tyr Ala Asn Glu Leu Ser
210                 215                 220

Leu Asp Gly Phe Arg Ile Asp Ala Ala Lys His Ile Lys Phe Ser Phe
225                 230                 235                 240

Leu Arg Asp Trp Val Gln Ala Val Arg Gln Ala Thr Gly Lys Glu Met
                245                 250                 255

Phe Thr Val Ala Glu Tyr Trp Gln Asn Asn Ala Gly Lys Leu Glu Asn
                260                 265                 270

Tyr Leu Asn Lys Thr Ser Phe Asn Gln Ser Val Phe Asp Val Pro Leu
                275                 280                 285

His Phe Asn Leu Gln Ala Ala Ser Ser Gln Gly Gly Gly Tyr Asp Met
                290                 295                 300

Arg Arg Leu Leu Asp Gly Thr Val Val Ser Arg His Pro Glu Lys Ala
305                 310                 315                 320

Val Thr Phe Val Glu Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Thr Ser Pro Lys Glu Ile Pro Ser Leu Lys Asp Asn Ile
                370                 375                 380

Glu Pro Ile Leu Lys Ala Arg Lys Glu Tyr Ala Tyr Gly Pro Gln His
385                 390                 395                 400

Asp Tyr Ile Asp His Pro Asp Val Ile Gly Trp Thr Arg Glu Gly Asp
                405                 410                 415

Ser Ser Ala Ala Lys Ser Gly Leu Ala Ala Leu Ile Thr Asp Gly Pro
                420                 425                 430

Gly Gly Ser Lys Arg Met Tyr Ala Gly Leu Lys Asn Ala Gly Glu Thr
                435                 440                 445

Trp Tyr Asp Ile Thr Gly Asn Arg Ser Asp Thr Val Lys Ile Gly Ser
                450                 455                 460

Asp Gly Trp Gly Glu Phe His Val Asn Asp Gly Ser Val Ser Ile Tyr
465                 470                 475                 480

Val Gln Lys

<210> SEQ ID NO 6
<211> LENGTH: 483
<212> TYPE: PRT
<213> ORGANISM: Bacillus licheniformis

<400> SEQUENCE: 6

Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
```

-continued

```
                35                  40                  45
Thr Ser Gln Ala Asp Val Gly Tyr Gly Ala Tyr Asp Leu Tyr Asp Leu
 50                  55                  60
Gly Glu Phe His Gln Lys Gly Thr Val Arg Thr Lys Tyr Gly Thr Lys
 65                  70                  75                  80
Gly Glu Leu Gln Ser Ala Ile Lys Ser Leu His Ser Arg Asp Ile Asn
                 85                  90                  95
Val Tyr Gly Asp Val Val Ile Asn His Lys Gly Gly Ala Asp Ala Thr
                100                 105                 110
Glu Asp Val Thr Ala Val Glu Val Asp Pro Ala Asp Arg Asn Arg Val
                115                 120                 125
Ile Ser Gly Glu His Arg Ile Lys Ala Trp Thr His Phe His Phe Pro
130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Asn Glu Asn Gly Asn
                180                 185                 190
Tyr Asp Tyr Leu Met Tyr Ala Asp Ile Asp Tyr Asp His Pro Asp Val
                195                 200                 205
Ala Ala Glu Ile Lys Arg Trp Gly Thr Trp Tyr Ala Asn Glu Leu Gln
210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
                260                 265                 270
Tyr Leu Asn Lys Thr Asn Phe Asn His Ser Val Phe Asp Val Pro Leu
                275                 280                 285
His Tyr Gln Phe His Ala Ala Ser Thr Gln Gly Gly Gly Tyr Asp Met
290                 295                 300
Arg Lys Leu Leu Asn Ser Thr Val Val Ser Lys His Pro Leu Lys Ala
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
                340                 345                 350
Thr Arg Glu Ser Gly Tyr Pro Gln Val Phe Tyr Gly Asp Met Tyr Gly
                355                 360                 365
Thr Lys Gly Asp Ser Gln Arg Glu Ile Pro Ala Leu Lys His Lys Ile
370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
                420                 425                 430
Gly Gly Ala Lys Arg Met Tyr Val Gly Arg Gln Asn Ala Gly Glu Thr
                435                 440                 445
Trp His Asp Ile Thr Gly Asn Arg Ser Glu Pro Val Val Ile Asn Ser
450                 455                 460
```

```
Glu Gly Trp Gly Glu Phe His Val Asn Gly Gly Ser Val Ser Ile Tyr
465                 470                 475                 480

Val Gln Arg
```

<210> SEQ ID NO 7
<211> LENGTH: 515
<212> TYPE: PRT
<213> ORGANISM: Bacillus stearothermophilus

<400> SEQUENCE: 7

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
                20                  25                  30

Leu Ser Ser Leu Gly Ile Thr Ala Leu Trp Leu Pro Pro Ala Tyr Lys
            35                  40                  45

Gly Thr Ser Arg Ser Asp Val Gly Tyr Gly Val Tyr Asp Leu Tyr Asp
50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Ser Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Asp Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Met Lys Thr Asn Gly Thr Met Ser Leu Phe Asp
        275                 280                 285

Ala Pro Leu His Asn Lys Phe Tyr Thr Ala Ser Lys Ser Gly Gly Thr
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350
```

```
Phe Ile Leu Thr Arg Gln Glu Gly Tyr Pro Cys Val Phe Tyr Gly Asp
            355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
                435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Trp Ser Ile Thr Thr
                485                 490                 495

Arg Pro Trp Thr Asp Glu Phe Val Arg Trp Thr Glu Pro Arg Leu Val
            500                 505                 510

Ala Trp Pro
        515

<210> SEQ ID NO 8
<211> LENGTH: 487
<212> TYPE: PRT
<213> ORGANISM: Bacillus sp. MK716

<400> SEQUENCE: 8

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Ala Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
```

```
            195                 200                 205
Pro Glu Val Val Thr Glu Leu Lys Asn Trp Gly Lys Trp Tyr Val Asn
210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
450                 455                 460

Asp Gly Trp Gly Glu Phe Lys Val Asn Gly Gly Ser Val Ser Val Trp
465                 470                 475                 480

Val Pro Arg Arg Pro Val Asn
                485

<210> SEQ ID NO 9
<211> LENGTH: 584
<212> TYPE: PRT
<213> ORGANISM: Bacillus sp. TS-23

<400> SEQUENCE: 9

Ala Asn Thr Ala Pro Ile Asn Glu Thr Met Met Gln Tyr Phe Glu Trp
1               5                   10                  15

Asp Leu Pro Asn Asp Gly Thr Leu Trp Thr Lys Val Lys Asn Glu Ala
            20                  25                  30

Ala Asn Leu Ser Ser Leu Gly Ile Thr Ala Leu Trp Leu Pro Pro Ala
        35                  40                  45

Tyr Lys Gly Thr Ser Gln Ser Asp Val Gly Tyr Gly Val Tyr Asp Leu
    50                  55                  60

Tyr Asp Leu Gly Glu Phe Asn Gln Lys Gly Thr Ile Arg Thr Lys Tyr
65                  70                  75                  80
```

```
Gly Thr Lys Thr Gln Tyr Ile Gln Ala Ile Gln Ala Ala Lys Ala Ala
                85                  90                  95

Gly Met Gln Val Tyr Ala Asp Val Val Phe Asn His Lys Ala Gly Ala
            100                 105                 110

Asp Gly Thr Glu Phe Val Asp Ala Val Glu Val Asp Pro Ser Asn Arg
        115                 120                 125

Asn Gln Glu Thr Ser Gly Thr Tyr Gln Ile Gln Ala Trp Thr Lys Phe
    130                 135                 140

Asp Phe Pro Gly Arg Gly Asn Thr Tyr Ser Ser Phe Lys Trp Arg Trp
145                 150                 155                 160

Tyr His Phe Asp Gly Thr Asp Trp Asp Glu Ser Arg Lys Leu Asn Arg
                165                 170                 175

Ile Tyr Lys Phe Arg Ser Thr Gly Lys Ala Trp Asp Trp Glu Val Asp
            180                 185                 190

Thr Glu Asn Gly Asn Tyr Asp Tyr Leu Met Phe Ala Asp Leu Asp Met
        195                 200                 205

Asp His Pro Glu Val Val Thr Glu Leu Lys Asn Trp Gly Thr Trp Tyr
    210                 215                 220

Val Asn Thr Thr Asn Ile Asp Gly Phe Arg Leu Asp Ala Val Lys His
225                 230                 235                 240

Ile Lys Tyr Ser Phe Phe Pro Asp Trp Leu Thr Tyr Val Arg Asn Gln
                245                 250                 255

Thr Gly Lys Asn Leu Phe Ala Val Gly Glu Phe Trp Ser Tyr Asp Val
            260                 265                 270

Asn Lys Leu His Asn Tyr Ile Thr Lys Thr Asn Gly Ser Met Ser Leu
        275                 280                 285

Phe Asp Ala Pro Leu His Asn Asn Phe Tyr Thr Ala Ser Lys Ser Ser
    290                 295                 300

Gly Tyr Phe Asp Met Arg Tyr Leu Leu Asn Asn Thr Leu Met Lys Asp
305                 310                 315                 320

Gln Pro Ser Leu Ala Val Thr Leu Val Asp Asn His Asp Thr Gln Pro
                325                 330                 335

Gly Gln Ser Leu Gln Ser Trp Val Glu Pro Trp Phe Lys Pro Leu Ala
            340                 345                 350

Tyr Ala Phe Ile Leu Thr Arg Gln Glu Gly Tyr Pro Cys Val Phe Tyr
        355                 360                 365

Gly Asp Tyr Tyr Gly Ile Pro Lys Tyr Asn Ile Pro Gly Leu Lys Ser
    370                 375                 380

Lys Ile Asp Pro Leu Leu Ile Ala Arg Arg Asp Tyr Ala Tyr Gly Thr
385                 390                 395                 400

Gln Arg Asp Tyr Ile Asp His Gln Asp Ile Ile Gly Trp Thr Arg Glu
                405                 410                 415

Gly Ile Asp Thr Lys Pro Asn Ser Gly Leu Ala Ala Leu Ile Thr Asp
            420                 425                 430

Gly Pro Gly Gly Ser Lys Trp Met Tyr Val Gly Lys Lys His Ala Gly
        435                 440                 445

Lys Val Phe Tyr Asp Leu Thr Gly Asn Arg Ser Asp Thr Val Thr Ile
    450                 455                 460

Asn Ala Asp Gly Trp Gly Glu Phe Lys Val Asn Gly Gly Ser Val Ser
465                 470                 475                 480

Ile Trp Val Ala Lys Thr Ser Asn Val Thr Phe Thr Val Asn Asn Ala
                485                 490                 495

Thr Thr Thr Ser Gly Gln Asn Val Tyr Val Val Ala Asn Ile Pro Glu
```

```
                500                 505                 510
Leu Gly Asn Trp Asn Thr Ala Asn Ala Ile Lys Met Asn Pro Ser Ser
            515                 520                 525

Tyr Pro Thr Trp Lys Ala Thr Ile Ala Leu Pro Gln Gly Lys Ala Ile
        530                 535                 540

Glu Phe Lys Phe Ile Lys Lys Asp Gln Ala Gly Asn Val Ile Trp Glu
545                 550                 555                 560

Ser Thr Ser Asn Arg Thr Tyr Thr Val Pro Phe Ser Ser Thr Gly Ser
            565                 570                 575

Tyr Thr Ala Ser Trp Asn Val Pro
            580

<210> SEQ ID NO 10
<211> LENGTH: 481
<212> TYPE: PRT
<213> ORGANISM: Bacillus KSM-K38

<400> SEQUENCE: 10

Ala Asp Gly Leu Asn Gly Thr Met Met Gln Tyr Tyr Glu Trp His Leu
1               5                   10                  15

Glu Asn Asp Gly Gln His Trp Asn Arg Leu His Asp Asp Ala Ala Ala
            20                  25                  30

Leu Ser Asp Ala Gly Ile Thr Ala Ile Trp Ile Pro Pro Ala Tyr Lys
        35                  40                  45

Gly Asn Ser Gln Ala Asp Val Gly Tyr Gly Ala Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Leu Glu Arg Ala Ile Gly Ser Leu Lys Ser Asn Asp Ile
                85                  90                  95

Asn Val Tyr Gly Asp Val Val Met Asn His Lys Met Gly Ala Asp Phe
            100                 105                 110

Thr Glu Ala Val Gln Ala Val Gln Val Asn Pro Thr Asn Arg Trp Gln
        115                 120                 125

Asp Ile Ser Gly Ala Tyr Thr Ile Asp Ala Trp Thr Gly Phe Asp Phe
    130                 135                 140

Ser Gly Arg Asn Asn Ala Tyr Ser Asp Phe Lys Trp Arg Trp Phe His
145                 150                 155                 160

Phe Asn Gly Val Asp Trp Asp Gln Arg Tyr Gln Glu Asn His Ile Phe
                165                 170                 175

Arg Phe Ala Asn Thr Asn Trp Asn Trp Arg Val Asp Glu Glu Asn Gly
            180                 185                 190

Asn Tyr Asp Tyr Leu Leu Gly Ser Asn Ile Asp Phe Ser His Pro Glu
        195                 200                 205

Val Gln Asp Glu Leu Lys Asp Trp Gly Ser Trp Phe Thr Asp Glu Leu
    210                 215                 220

Asp Leu Asp Gly Tyr Arg Leu Asp Ala Ile Lys His Ile Pro Phe Trp
225                 230                 235                 240

Tyr Thr Ser Asp Trp Val Arg His Gln Arg Asn Glu Ala Asp Gln Asp
                245                 250                 255

Leu Phe Val Val Gly Glu Tyr Trp Lys Asp Asp Val Gly Ala Leu Glu
            260                 265                 270

Phe Tyr Leu Asp Glu Met Asn Trp Glu Met Ser Leu Phe Asp Val Pro
        275                 280                 285
```

-continued

```
Leu Asn Tyr Asn Phe Tyr Arg Ala Ser Gln Gln Gly Ser Tyr Asp
    290                 295                 300

Met Arg Asn Ile Leu Arg Gly Ser Leu Val Glu Ala His Pro Met His
305                 310                 315                 320

Ala Val Thr Phe Val Asp Asn His Asp Thr Gln Pro Gly Glu Ser Leu
                325                 330                 335

Glu Ser Trp Val Ala Asp Trp Phe Lys Pro Leu Ala Tyr Ala Thr Ile
                340                 345                 350

Leu Thr Arg Glu Gly Tyr Pro Asn Val Phe Tyr Gly Asp Tyr Tyr
        355                 360                 365

Gly Ile Pro Asn Asp Asn Ile Ser Ala Lys Lys Asp Met Ile Asp Glu
    370                 375                 380

Leu Leu Asp Ala Arg Gln Asn Tyr Ala Tyr Gly Thr Gln His Asp Tyr
385                 390                 395                 400

Phe Asp His Trp Asp Val Val Gly Trp Thr Arg Glu Gly Ser Ser Ser
                405                 410                 415

Arg Pro Asn Ser Gly Leu Ala Thr Ile Met Ser Asn Gly Pro Gly Gly
                420                 425                 430

Ser Lys Trp Met Tyr Val Gly Arg Gln Asn Ala Gly Gln Thr Trp Thr
            435                 440                 445

Asp Leu Thr Gly Asn Asn Gly Ala Ser Val Thr Ile Asn Gly Asp Gly
    450                 455                 460

Trp Gly Glu Phe Phe Thr Asn Gly Gly Ser Val Ser Val Tyr Val Asn
465                 470                 475                 480

Gln
```